(12) United States Patent
Rosenkilde et al.

(10) Patent No.: US 11,572,399 B2
(45) Date of Patent: Feb. 7, 2023

(54) LONG-ACTING GIP PEPTIDE ANALOGUES

(71) Applicant: University of Copenhagen, Copenhagen K (DK)

(72) Inventors: Mette Marie Rosenkilde, Hellerup (DK); Jens Juul Holst, Hellerup (DK); Lærke Smidt Gasbjerg, Vanløse (DK); Alexander Hovard Sparre-Ulrich, Copenhagen N (DK); Maria Buur Nordskov Gabe, Værløse (DK)

(73) Assignee: UNIVERSITY OF COPENHAGEN, Copenhagen K (DK)

( * ) Notice: Subject to any disclaimer, the term of this patent is extended or adjusted under 35 U.S.C. 154(b) by 0 days.

(21) Appl. No.: 16/617,698

(22) PCT Filed: May 31, 2018

(86) PCT No.: PCT/EP2018/064355
§ 371 (c)(1),
(2) Date: Nov. 27, 2019

(87) PCT Pub. No.: WO2018/220123
PCT Pub. Date: Dec. 6, 2018

(65) Prior Publication Data
US 2020/0087373 A1 Mar. 19, 2020

(30) Foreign Application Priority Data
May 31, 2017 (EP) .................................... 17173628

(51) Int. Cl.
C07K 14/605 (2006.01)
A61K 38/00 (2006.01)

(52) U.S. Cl.
CPC ............ C07K 14/605 (2013.01); *A61K 38/00* (2013.01)

(58) Field of Classification Search
None
See application file for complete search history.

(56) References Cited

U.S. PATENT DOCUMENTS

| | | |
|---|---|---|
| 6,004,297 A | 12/1999 | Steenfeldt-Jensen et al. |
| 6,268,343 B1 | 7/2001 | Knudsen et al. |
| 6,384,016 B1 | 5/2002 | Kaarsholm |
| 6,410,508 B1 | 6/2002 | Isales et al. |
| 6,458,924 B2 | 10/2002 | Knudsen et al. |
| 7,326,688 B2 | 2/2008 | O'Harte et al. |
| 7,875,587 B2 | 1/2011 | Gault et al. |
| 8,450,266 B2 | 5/2013 | Dong et al. |
| 9,072,703 B2 | 7/2015 | Dong |
| 10,774,127 B2 * | 9/2020 | Hartmann .............. C07K 14/645 |
| 2001/0011071 A1 | 8/2001 | Knudsen et al. |
| 2005/0272652 A1 | 12/2005 | Gault et al. |
| 2007/0167370 A1 | 7/2007 | Gault et al. |
| 2008/0009603 A1 | 1/2008 | Gault et al. |
| 2008/0312157 A1 | 12/2008 | Levy et al. |
| 2018/0258152 A1 * | 9/2018 | Sparre-Ulrich ........ A61K 38/26 |
| 2019/0330332 A1 | 10/2019 | Okahara et al. |
| 2019/0330333 A1 | 10/2019 | Okahara et al. |
| 2019/0330334 A1 | 10/2019 | Okahara et al. |

FOREIGN PATENT DOCUMENTS

| | | |
|---|---|---|
| EP | 3560514 A1 | 10/2019 |
| EP | 3560515 A1 | 10/2019 |
| EP | 3569248 A1 | 11/2019 |
| JP | 2010-500996 A | 1/2010 |
| JP | 2013-518115 A | 5/2013 |
| JP | 2016-521253 A | 7/2016 |
| WO | 1996/29342 | 9/1996 |
| WO | 1998/08871 | 3/1998 |
| WO | 1998/24464 A1 | 6/1998 |
| WO | 1999/43708 A1 | 9/1999 |
| WO | 2000/20592 A1 | 4/2000 |
| WO | 2000/34331 A2 | 6/2000 |
| WO | 2000/58360 A2 | 10/2000 |
| WO | 200246227 A2 | 6/2002 |
| WO | 2003082898 A2 | 10/2003 |
| WO | 2004067548 A2 | 8/2004 |
| WO | WO-2005/082928 A2 | 9/2005 |
| WO | WO-2005/082928 A3 | 9/2005 |
| WO | 2006086769 A2 | 8/2006 |
| WO | 2006097537 A2 | 9/2006 |
| WO | 2007109354 A2 | 9/2007 |
| WO | 2010016935 A2 | 2/2010 |
| WO | 2010016936 A1 | 2/2010 |
| WO | 2010016938 A2 | 2/2010 |
| WO | 2010016940 A2 | 2/2010 |

(Continued)

OTHER PUBLICATIONS

Irwin et al. "GIP(Lys16PAL) and GIP(Lys37PAL): Novel Long-Acting Acylated Analogues of Glucose-Dependent Insulinotropic Polypeptide with Improved Antidiabetic Potential" J. Med. Chem. 49:1047-1054. (Year: 2006).*

Adrian et al. Pancreatic polypeptide, glucagon and insulin secretion from the isolated perfused canine pancreas. Diabetologia (1978), 14(6), 413-417.

Ahlqvist et al. Link Between GIP and Osteopontin in Adipose Tissue and Insulin Resistance.Diabetes (2013), 62(6), 2088-2094.

(Continued)

*Primary Examiner* — Sudhakar Katakam
*Assistant Examiner* — Zachary J Miknis
(74) *Attorney, Agent, or Firm* — Mintz, Levin, Cohn, Ferris, Glovsky & Popeo, P.C.

(57) ABSTRACT

Disclosed are glucose-dependent insulinotropic peptide (GIP)-derived peptide analogues GIPS-30 and GIP3-30 which are antagonists of the GIP receptor and comprises at least one fatty acid molecule to increase half-life while maintaining antagonistic properties.

23 Claims, 5 Drawing Sheets

Specification includes a Sequence Listing.

(56) References Cited

FOREIGN PATENT DOCUMENTS

| WO | 2010016944 | A2 | 2/2010 | | |
|---|---|---|---|---|---|
| WO | 2012055770 | A1 | 5/2012 | | |
| WO | 2012/088379 | | 6/2012 | | |
| WO | 2012167744 | A1 | 12/2012 | | |
| WO | 2016034186 | A1 | 3/2016 | | |
| WO | WO-2016034186 | A1 * | 3/2016 | ........... | C07K 14/605 |
| WO | 2016/066744 | | 5/2016 | | |
| WO | 2016205488 | A1 | 12/2016 | | |
| WO | 2018/220123 | | 12/2018 | | |

OTHER PUBLICATIONS

Asmar et al. Glucose-Dependent Insulinotropic Polypeptide May Enhance Fatty Acid Re-esterification in Subcutaneous Abdominal Adipose Tissue in Lean Humans. Diabetes (2010), 59(9), 2160-2163.
Baggio et al. Biology of Incretins: GLP-1 and GIP. Gastroenterology (2007), 132(6), 2131-2157.
Brunicardi et al. Selective neurohormonal interactions in islet cell secretion in the isolated perfused human pancreas. Journal of Surgical Research (1990), 48(4), 273-278.
Brons et al. Impact of short-term high-fat feeding on glucose and insulin metabolism in young healthy men. The Journal of Physiology (2009), 587(10), 2387-2397.
Calanna et al. Secretion of Glucose-Dependent Insulinotropic Polypeptide in Patients With Type 2 Diabetes: Systematic review and meta-analysis of clinical studies. Diabetes Care (2013), 36(10), 3346-3352.
Christensen et al. Glucose-Dependent Insulinotropic Polypeptide Augments Glucagon Responses to Hypoglycemia in Type 1 Diabetes. Diabetes (2014).
Christensen et al. Glucose-Dependent Insulinotropic Polypeptide: A Bifunctional Glucose-Dependent Regulator of Glucagon and Insulin Secretion in Humans. Diabetes (2011), 60(12), 3103-3109.
Christensen et al. Glucose-dependent Insulinotropic Polypeptide: Blood Glucose Stabilizing Effects in Patients with Type 2 Diabetes. The Journal of Clinical Endocrinology & Metabolism (2014), 99(3), E418-E426.
Deacon et al. GIP-(3-42) does not antagonize insulinotropic effects of GIP at physiological concentrations. American Journal of Physiology—Endocrinology and Metabolism (2006), 291(3), E468-475.
Deblasi et al. Calculating receptor number from binding experiments using same compound as radioligand and competitor. Trends in Pharmacological Sciences (1989), 10, 227-229.
Deschamps et al. Effects of diet on insulin and gastric inhibitory polypeptide levels in obese children. Pediatr Res (1980), 14(4 Pt 1), 300-303.
Ding et al. Glucagon-like peptide I and glucose-dependent insulinotropic polypeptide stimulate Ca2+-induced secretion in rat alpha-cells by a protein kinase A-mediated mechanism. Diabetes (1997), 46(5), 792-800.
Dupre J, Caussignac Y, McDonald TJ, Van Vliet S. Stimulation of Glucagon Secretion by Gastric Inhibitory Polypeptide in Patients with Hepatic Cirrhosis and Hyperglucagonemia. The Journal of Clinical Endocrinology & Metabolism 1991;72(1):125-129.
Ebert et al. Release of gastric inhibitory polypeptide (GIP) by intraduodenal acidification in rats and humans and abolishment of the incretin effect of acid by GIP-antiserum in rats. Gastroenterology (1979), 76(3), 515-523.
Fujita et al. Differential processing of pro-glucose-dependent insulinotropic polypeptide in gut. American Journal of Physiology—Gastrointestinal and Liver Physiology (2010), 298(5).
Fulurija et al. Vaccination against GIP for the Treatment of Obesity. PLoS ONE (2008), 3(9), e3163.
Gault et al. Characterization of the Cellular and Metabolic Effects of a Novel Enzyme-Resistant Antagonist of Glucose-Dependent Insulinotropic Polypeptide. Biochemical and Biophysical Research Communications (2002), 290(5), 1420-1426.

Gelling et al. GIP(6-30amide) contains the high affinity binding region of GIP and is a potent inhibitor of GIP1-42 action in vitro. Regulatory Peptides (1997), 69(3), 151-154.
Getty-Kaushik et al. Glucose-Dependent Insulinotropic Polypeptide Modulates Adipocyte Lipolysis and Reesterification. Obesity (2006), 14(7), 1124-1131.
Goetze et al. Peptide hormones and their prohormones as biomarkers. Biomarkers Med (2009), 3(4), 335-338.
Goetze et al. Processing-independent analysis of peptide hormones and prohormones in plasma.Front Biosci (2012), 17, 1804-1815.
Graham et al. A new technique for the assay of infectivity of human adenovirus 5 DNA. Virology (1973), 52(2), 456-467.
Gutniak et al. Antidiabetogenic Effect of Glucagon-like Peptide-1 (7-36)amide in Normal Subjects and Patients with Diabetes Mellitus. N Engl J Med (1992), 326(20), 1316-1322.
Hansen et al., N-terminally and C-terminally truncated forms of glucose-dependent insulinotropic polypeptide are high-affinity competitive antagonists of the human GIP receptor. British Journal of Pharmacology (2016) 173 826-838.
Hauner et al. Effects of gastric inhibitory polypeptide on glucose and lipid metabolism of isolated rat adipocytes. Ann Nutr Metab (1988), 32(5-6), 282-288.
Heer et al. Glucagon-like peptide-1, but not glucose-dependent insulinotropic peptide, inhibits glucagon secretion via somatostatin (receptor subtype 2) in the perfused rat pancreas. Diabetologia (2008), 51(12), 2263-2270.
Hinke et al. Identification of a bioactive domain in the amino-terminus of glucose-dependent insulinotropic polypeptide (GIP). Biochimica et Biophysica Acta (BBA)—Protein Structure and Molecular Enzymology (2001), 1547(1), 143-155.
Hinke et al. Structure-Activity Relationships of Glucose-Dependent Insulinotropic Polypeptide (GIP). Biological Chemistry (2003), 384(3), 403-407.
Hinke et al., In depth analysis of the N-terminal bioactive domain of gastric inhibitory polypeptide. Life Sciences 75 (2004)1857-1870.
Holst JJ. On the Physiology of GIP and GLP-1. HORM Metab Res (2004), 36(11/12), 747-754.
Holst, J. J. & Bersani, M. 1991. 1—Assays for Peptide Products of Somatostatin Gene Expression. In: CONN, P. M. (ed ) Methods in Neurosciences. Academic Press.
Hoejberg et al. Four weeks of near-normalisation of blood glucose improves the insulin response to glucagon-like peptide-1 and glucose-dependent insulinotropic polypeptide in patients with type 2 diabetes. Diabetologia (2009), 52(2), 199-207.
Irwin et al. Active immunisation against gastric inhibitory polypeptide (GIP) improves blood glucose control in an animal model of obesity-diabetes. Biological Chemistry. Bchm (2009), 390(75), Jul. 16, 2014.
Irwin et al. Biological activity and antidiabetic potential of synthetic fragment peptides of glucose-dependent insulinotropic polypeptide, GIP(1-16) and (Pro3)GIP(1-16). Regulatory Peptides (2006), 135(1GÇô2), 45-53.
Jorgensen et al. Exaggerated Glucagon-Like Peptide 1 Response is Important for Improved β-Cell Function and Glucose Tolerance After Roux-en-γ Gastric Bypass in Patients With Type 2 Diabetes. Diabetes (2013), 62(9), 3044-3052.
Kerr et al. Characterization and biological actions of N-terminal truncated forms of glucose-dependent insulinotropic polypeptide. Biochemical and Biophysical Research Communications (2011), 404(3), 870-876.
Kim et al. GIP-Overexpressing Mice Demonstrate Reduced Diet-Induced Obesity and Steatosis, and Improved Glucose Homeostasis. PLoS ONE (2012), 7(7), e40156.
Kissow et al. Glucagon-like peptide-1 (GLP-1) receptor agonism or DPP-4 inhibition does not accelerate neoplasia in carcinogen treated mice.Regulatory Peptides (2012), 179, 91-100.
Lazareno et al. Estimation of competitive antagonist affinity from functional inhibition curves using the Gaddum, Schild and Cheng-Prusoff equations. Br J Pharmacol, (1993) 109, 1110-1119.
Martin et al. A novel acylated form of (d-Ala(2))GIP with improved antidiabetic potential, lacking effect on body fat stores. Biochimica et Biophysica Acta, (2013), 1830(6), 3407-3413.

(56) References Cited

OTHER PUBLICATIONS

Meier et al. Gastric inhibitory polypeptide (GIP) dose-dependently stimulates glucagon secretion in healthy human subjects at euglycaemia. Diabetologia (2003), 46(6), 798-801.
Miyawaki et al. Glucose intolerance caused by a defect in the entero-insular axis: A study in gastric inhibitory polypeptide receptor knockout mice.Proceedings of the National Academy of Sciences (1999), 96(26), 14843-14847.
Miyawaki et al. Inhibition of gastric inhibitory polypeptide signaling prevents obesity. Nat Med (2002), 8(7), 738-742.
Nakamura et al. Biological and functional characteristics of a novel low-molecular weight antagonist of glucose-dependent insulinotropic polypeptide receptor, SKL-14959, in vitro and in vivo. Diabetes, Obesity and Metabolism (2012), 14(6), 511-517.
Nasteska et al. Chronic Reduction of GIP Secretion Alleviates Obesity and Insulin Resistance Under High-Fat Diet Conditions. Diabetes (2014), 63(7), 2332-2343.
Pathak et al. Antagonism of gastric inhibitory polypeptide (GIP) by palmitoylation of GIP analogues with N- and C-terminal modifications improves obesity and metabolic control in high faffed mice. Molecular and Cellular Endocrinology (2015), 401(5), 120-129.
Pederson et al. Interaction of Gastric Inhibitory Polypeptide, Glucose, and Arginine on Insulin and Glucagon Secretion from the Perfused Rat Pancreas Endocrinology (1978), 103(2), 610-615.
Raufman et al. Exendin-3, a novel peptide from Heloderma horridum venom, interacts with vasoactive intestinal peptide receptors and a newly described receptor on dispersed acini from guinea pig pancreas. Description of exendin-3(9-39) amide, a specific exendin receptor antagonist. Journal of Biological Chemistry (1991), 266(5), 2897-2902.
Ravn et al. Structural and Pharmacological Characterization of Novel Potent and Selective Monoclonal Antibody Antagonists of Glucose-dependent Insulinotropic Polypeptide Receptor.Journal of Biological Chemistry (2013), 288 (27), 19760-19772.
Rosenkilde et al. Mutations along transmembrane segment II of the NK-1 receptor affect substance P competition with non-peptide antagonists but not substance P binding. Journal of Biological Chemistry. J Biol Chem (1994), 269, 28160-28164.
Sauber, J., et al. Association of variants in gastric inhibitory polypeptide receptor gene with impaired glucose homeostasis in obese children and adolescents from Berlin. European Journal of Endocrinology. 2010;163(2):259-64.
Song et al. Glucose-Dependent Insulinotropic Polypeptide Enhances Adipocyte Development and Glucose Uptake in Part Through Akt Activation. Gastroenterology (2007), 133(6), 1796-1805.
Sparre-Ulrich AH, Gabe MN, Gasbjerg LS, Christiansen CB, Svendsen B, Hartmann B, et al. GIP(3-30)NH2 is a potent competitive antagonist of the GIP receptor and effectively inhibits GIP-mediated insulin, glucagon, and somatostatin release. Biochemical pharmacology. 2017;131:78-88.
Starich et al. GIP increases insulin receptor affinity and cellular sensitivity in adipocytes. Am J Physiol (1985), 249(6 Pt 1), E603-E607.
Tseng et al. Postprandial stimulation of insulin release by glucose-dependent insulinotropic polypeptide (GIP). Effect of a specific glucose-dependent insulinotropic polypeptide receptor antagonist in the rat. J Clin Invest (1996), 98(11), 2440-2445.
Widenmaier et al., A GIP Receptor Agonist Exhibits beta-Cell Anti-Apoptotic Actions in Rat Models of Diabetes Resulting in Improved beta-Cell Function and Glycemic Control.PLoS ONE (2010), 5(3), e9590.
Irwin, N. et al., GIP(Lys16PAL) and GIP(Lys 7 PAL): Novel Long-Acting Acylated Analogues of Glucose-Dependent Insulinotropic Polypeptide with Improved Antidiabetic Potential, Journal of Medicinal Chemistry, vol. 49, No. 3, pp. 1047-1054, 2006.
Pathak, V. et al., Sequential induction of beta cell rest and stimulation using stable GIP inhibitor and GLP-1 mimetic peptides improves metabolic control in C57BL/KsJdb/dbmice, Diabetologica, vol. 58, No. 9, 2015.
Gault, V. et al., Evidence that the major degradation product of glucose-dependent insulinotropic polypeptide, GIP (3-42), is a GIP receptor antagonist in vivo, Journal of Endocrinology, 175: 525-533, 2002.
Extended European Search Report for Application No. 18182456.6-1111/3530671, dated Oct. 14, 2019.
Gault, Characterisation and biological activity of Glu3 amino acid substituted GIP receptor antagonists, Archives of Biochemistry and Biophysics 461, 263-274, 2007.
Perry, R. et al., Characterisation of Glucose-Dependent Insulinotropic Polypeptide Receptor Antagonists in Rodent Pancreatic Beta Cells and Mice, Clinical Medicine Insights: Endocrinology and Diabetes, 12: 1-9, 2019.

\* cited by examiner

SEQUENCE LISTING

```
<160> NUMBER OF SEQ ID NOS: 156

<210> SEQ ID NO 1
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(26)
<223> OTHER INFORMATION: GIP analogues

<400> SEQUENCE: 1

Thr Phe Ile Ser Asp Tyr Ser Ile Ala Met Asp Lys Ile His Gln Gln
1               5                   10                  15

Asp Phe Val Asn Trp Leu Leu Ala Gln Lys
            20                  25

<210> SEQ ID NO 2
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(28)
<223> OTHER INFORMATION: GIP analogues

<400> SEQUENCE: 2

Glu Gly Thr Phe Ile Ser Asp Tyr Ser Ile Ala Met Asp Lys Ile His
1               5                   10                  15

Gln Gln Asp Phe Val Asn Trp Leu Leu Ala Gln Lys
            20                  25

<210> SEQ ID NO 3
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (7)..(7)
```

```
<223> OTHER INFORMATION: is selected from the group consisting of S, K
      and Orn,
<220> FEATURE:
<221> NAME/KEY: PEPTIDE
<222> LOCATION: (8)..(8)
<223> OTHER INFORMATION: is selected from the group consisting of I, K
      and Orn,
<220> FEATURE:
<221> NAME/KEY: PEPTIDE
<222> LOCATION: (9)..(9)
<223> OTHER INFORMATION: is selected from the group consisting of A, K
      and Orn,
<220> FEATURE:
<221> NAME/KEY: PEPTIDE
<222> LOCATION: (10)..(10)
<223> OTHER INFORMATION: is selected from the group consisting of M, K,
      L, S, Nle and Mox,
<220> FEATURE:
<221> NAME/KEY: PEPTIDE
<222> LOCATION: (11)..(11)
<223> OTHER INFORMATION: is selected from the group consisting of D, E,
      A, K and Orn,
<220> FEATURE:
<221> NAME/KEY: PEPTIDE
<222> LOCATION: (12)..(12)
<223> OTHER INFORMATION: is selected from the group consisting of K, R,
      A and E,
<220> FEATURE:
<221> NAME/KEY: PEPTIDE
<222> LOCATION: (14)..(14)
<223> OTHER INFORMATION: is selected from the group consisting of H, A,
      R, K and Orn
<220> FEATURE:
<221> NAME/KEY: PEPTIDE
<222> LOCATION: (26)..(26)
<223> OTHER INFORMATION: is selected from the group consisting of K, R,
      A and E

<400> SEQUENCE: 3

Thr Phe Ile Ser Asp Tyr Xaa Xaa Xaa Xaa Xaa Xaa Ile Xaa Gln Gln
1               5                   10                  15

Asp Phe Val Asn Trp Leu Leu Ala Gln Xaa
            20                  25

<210> SEQ ID NO 4
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (9)..(9)
<223> OTHER INFORMATION: is selected from the group consisting of S, K
      and Orn,
<220> FEATURE:
<221> NAME/KEY: PEPTIDE
<222> LOCATION: (10)..(10)
<223> OTHER INFORMATION: is selected from the group consisting of I, K
      and Orn,
<220> FEATURE:
<221> NAME/KEY: PEPTIDE
<222> LOCATION: (11)..(11)
<223> OTHER INFORMATION: is selected from the group consisting of A, K
      and Orn,
<220> FEATURE:
<221> NAME/KEY: PEPTIDE
<222> LOCATION: (12)..(12)
<223> OTHER INFORMATION: X14 is selected from the group consisting of M,
      K, L, S, Nle and Mox,
<220> FEATURE:
<221> NAME/KEY: PEPTIDE
<222> LOCATION: (13)..(13)
<223> OTHER INFORMATION: is selected from the group consisting of D, E,
      A, K and Orn,
<220> FEATURE:
```

```
<221> NAME/KEY: PEPTIDE
<222> LOCATION: (14)..(14)
<223> OTHER INFORMATION: is selected from the group consisting of K, R,
      A and E
<220> FEATURE:
<221> NAME/KEY: PEPTIDE
<222> LOCATION: (16)..(16)
<223> OTHER INFORMATION: is selected from the group consisting of H, A,
      R, K and Orn
<220> FEATURE:
<221> NAME/KEY: PEPTIDE
<222> LOCATION: (28)..(28)
<223> OTHER INFORMATION: is selected from the group consisting of K, R,
      A and E

<400> SEQUENCE: 4

Glu Gly Thr Phe Ile Ser Asp Tyr Xaa Xaa Xaa Xaa Xaa Xaa Ile Xaa
1               5                  10                  15

Gln Gln Asp Phe Val Asn Trp Leu Leu Ala Gln Xaa
            20                  25

<210> SEQ ID NO 5
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(26)
<223> OTHER INFORMATION: GIP analogues

<400> SEQUENCE: 5

Thr Phe Ile Ser Asp Tyr Ser Ile Ala Met Asp Arg Ile Lys Gln Gln
1               5                  10                  15

Asp Phe Val Asn Trp Leu Leu Ala Gln Arg
            20                  25

<210> SEQ ID NO 6
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(26)
<223> OTHER INFORMATION: GIP analogues

<400> SEQUENCE: 6

Thr Phe Ile Ser Asp Tyr Ser Ile Ala Met Asp Arg Ile His Gln Gln
1               5                  10                  15

Asp Phe Val Asn Trp Leu Leu Ala Gln Arg
            20                  25

<210> SEQ ID NO 7
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(26)
<223> OTHER INFORMATION: GIP analogues

<400> SEQUENCE: 7

Thr Phe Ile Ser Asp Tyr Ser Ile Ala Met Asp Lys Ile Ala Gln Gln
1               5                  10                  15
```

```
Asp Phe Val Asn Trp Leu Leu Ala Gln Lys
            20                  25

<210> SEQ ID NO 8
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(26)
<223> OTHER INFORMATION: GIP analogues

<400> SEQUENCE: 8

Thr Phe Ile Ser Asp Tyr Ser Ile Ala Met Asp Lys Ile Lys Gln Gln
1               5                   10                  15

Asp Phe Val Asn Trp Leu Leu Ala Gln Lys
            20                  25

<210> SEQ ID NO 9
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 9

Thr Phe Ile Ser Asp Tyr Ser Ile Ala Met Glu Lys Ile Ala Gln Gln
1               5                   10                  15

Asp Phe Val Asn Trp Leu Leu Ala Gln Lys
            20                  25

<210> SEQ ID NO 10
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 10

Thr Phe Ile Ser Asp Tyr Ser Ile Ala Met Asp Ala Ile Ala Gln Gln
1               5                   10                  15

Asp Phe Val Asn Trp Leu Leu Ala Gln Lys
            20                  25

<210> SEQ ID NO 11
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 11

Thr Phe Ile Ser Asp Tyr Ser Ile Ala Met Glu Lys Ile His Gln Gln
```

1               5                  10                  15

Asp Phe Val Asn Trp Leu Leu Ala Gln Lys
            20                  25

<210> SEQ ID NO 12
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 12

Thr Phe Ile Ser Asp Tyr Ser Ile Ala Met Asn Lys Ile His Gln Gln
1               5                  10                  15

Asp Phe Val Asn Trp Leu Leu Ala Gln Lys
            20                  25

<210> SEQ ID NO 13
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 13

Thr Phe Ile Ser Asp Tyr Ser Ile Ala Met Asp Ala Ile His Gln Gln
1               5                  10                  15

Asp Phe Val Asn Trp Leu Leu Ala Gln Lys
            20                  25

<210> SEQ ID NO 14
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 14

Thr Phe Ile Ser Asp Tyr Ser Ile Ala Met Asp His Ile His Gln Gln
1               5                  10                  15

Asp Phe Val Asn Trp Leu Leu Ala Gln Lys
            20                  25

<210> SEQ ID NO 15
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 15

```
Thr Phe Ile Ser Asp Tyr Ser Ile Ala Met Asp Arg Ile His Gln Gln
1               5                   10                  15

Asp Phe Val Asn Trp Leu Leu Ala Gln Lys
            20                  25
```

<210> SEQ ID NO 16
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 16

```
Thr Phe Ile Ser Asp Tyr Ser Ile Ala Met Asp Lys Ile Phe Gln Gln
1               5                   10                  15

Asp Phe Val Asn Trp Leu Leu Ala Gln Lys
            20                  25
```

<210> SEQ ID NO 17
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 17

```
Thr Phe Ile Ser Asp Tyr Ser Ile Ala Met Asp Lys Ile Trp Gln Gln
1               5                   10                  15

Asp Phe Val Asn Trp Leu Leu Ala Gln Lys
            20                  25
```

<210> SEQ ID NO 18
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 18

```
Thr Phe Ile Ser Asp Tyr Ser Ile Ala Met Asp Lys Ile His Gln Gln
1               5                   10                  15

Asp Phe Val Asn Trp Leu Leu Ala Gln Arg
            20                  25
```

<210> SEQ ID NO 19
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 19

```
Thr Phe Ile Ser Asp Tyr Ser Ile Ala Met Asp Lys Ile His Gln Gln
1               5                   10                  15

Asp Phe Val Asn Trp Leu Leu Ala Gln His
            20                  25
```

<210> SEQ ID NO 20
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 20

```
Lys Phe Ile Ser Asp Tyr Ser Ile Ala Met Asp Lys Ile His Gln Gln
1               5                   10                  15

Asp Phe Val Asn Trp Leu Leu Ala Gln Lys
            20                  25
```

<210> SEQ ID NO 21
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 21

```
Thr Lys Ile Ser Asp Tyr Ser Ile Ala Met Asp Lys Ile His Gln Gln
1               5                   10                  15

Asp Phe Val Asn Trp Leu Leu Ala Gln Lys
            20                  25
```

<210> SEQ ID NO 22
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 22

```
Thr Phe Lys Ser Asp Tyr Ser Ile Ala Met Asp Lys Ile His Gln Gln
1               5                   10                  15

Asp Phe Val Asn Trp Leu Leu Ala Gln Lys
            20                  25
```

<210> SEQ ID NO 23
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

```
<400> SEQUENCE: 23

Thr Phe Ile Lys Asp Tyr Ser Ile Ala Met Asp Lys Ile His Gln Gln
1               5                   10                  15

Asp Phe Val Asn Trp Leu Leu Ala Gln Lys
            20                  25

<210> SEQ ID NO 24
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 24

Thr Phe Ile Ser Lys Tyr Ser Ile Ala Met Asp Lys Ile His Gln Gln
1               5                   10                  15

Asp Phe Val Asn Trp Leu Leu Ala Gln Lys
            20                  25

<210> SEQ ID NO 25
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 25

Thr Phe Ile Ser Asp Lys Ser Ile Ala Met Asp Lys Ile His Gln Gln
1               5                   10                  15

Asp Phe Val Asn Trp Leu Leu Ala Gln Lys
            20                  25

<210> SEQ ID NO 26
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 26

Thr Phe Ile Ser Asp Tyr Lys Ile Ala Met Asp Lys Ile His Gln Gln
1               5                   10                  15

Asp Phe Val Asn Trp Leu Leu Ala Gln Lys
            20                  25

<210> SEQ ID NO 27
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues
```

<400> SEQUENCE: 27

Thr Phe Ile Ser Asp Tyr Ser Lys Ala Met Asp Lys Ile His Gln Gln
1               5                   10                  15

Asp Phe Val Asn Trp Leu Leu Ala Gln Lys
            20                  25

<210> SEQ ID NO 28
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 28

Thr Phe Ile Ser Asp Tyr Ser Ile Lys Met Asp Lys Ile His Gln Gln
1               5                   10                  15

Asp Phe Val Asn Trp Leu Leu Ala Gln Lys
            20                  25

<210> SEQ ID NO 29
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 29

Thr Phe Ile Ser Asp Tyr Ser Ile Ala Lys Asp Lys Ile His Gln Gln
1               5                   10                  15

Asp Phe Val Asn Trp Leu Leu Ala Gln Lys
            20                  25

<210> SEQ ID NO 30
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 30

Thr Phe Ile Ser Asp Tyr Ser Ile Ala Met Lys Lys Ile His Gln Gln
1               5                   10                  15

Asp Phe Val Asn Trp Leu Leu Ala Gln Lys
            20                  25

<210> SEQ ID NO 31
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)

<223> OTHER INFORMATION: GIP analogues

<400> SEQUENCE: 31

Thr Phe Ile Ser Asp Tyr Ser Ile Ala Met Asp Lys Lys His Gln Gln
1               5                   10                  15

Asp Phe Val Asn Trp Leu Leu Ala Gln Lys
            20                  25

<210> SEQ ID NO 32
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 32

Thr Phe Ile Ser Asp Tyr Ser Ile Ala Met Asp Lys Ile His Lys Gln
1               5                   10                  15

Asp Phe Val Asn Trp Leu Leu Ala Gln Lys
            20                  25

<210> SEQ ID NO 33
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 33

Thr Phe Ile Ser Asp Tyr Ser Ile Ala Met Asp Lys Ile His Gln Lys
1               5                   10                  15

Asp Phe Val Asn Trp Leu Leu Ala Gln Lys
            20                  25

<210> SEQ ID NO 34
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 34

Thr Phe Ile Ser Asp Tyr Ser Ile Ala Met Asp Lys Ile His Gln Gln
1               5                   10                  15

Lys Phe Val Asn Trp Leu Leu Ala Gln Lys
            20                  25

<210> SEQ ID NO 35
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE

```
<222> LOCATION: (1)..(1)
<223> OTHER INFORMATION: GIP analogues

<400> SEQUENCE: 35

Thr Phe Ile Ser Asp Tyr Ser Ile Ala Met Asp Lys Ile His Gln Gln
1               5                   10                  15

Asp Lys Val Asn Trp Leu Leu Ala Gln Lys
            20                  25

<210> SEQ ID NO 36
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 36

Thr Phe Ile Ser Asp Tyr Ser Ile Ala Met Asp Lys Ile His Gln Gln
1               5                   10                  15

Asp Phe Lys Asn Trp Leu Leu Ala Gln Lys
            20                  25

<210> SEQ ID NO 37
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 37

Thr Phe Ile Ser Asp Tyr Ser Ile Ala Met Asp Lys Ile His Gln Gln
1               5                   10                  15

Asp Phe Val Lys Trp Leu Leu Ala Gln Lys
            20                  25

<210> SEQ ID NO 38
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 38

Thr Phe Ile Ser Asp Tyr Ser Ile Ala Met Asp Lys Ile His Gln Gln
1               5                   10                  15

Asp Phe Val Asn Lys Leu Leu Ala Gln Lys
            20                  25

<210> SEQ ID NO 39
<211> LENGTH: 26
<212> TYPE: PRT
<213> ORGANISM: Artificial Sequence
<220> FEATURE:
<223> OTHER INFORMATION: GIP analogues
<220> FEATURE:
```

<221> NAME/KEY: PEPTIDE
<222> LOCATION: (1)..(1)
<223> OTHER INFORMATION: GIP analogues

<400> SEQUENCE: 39

Thr Phe Ile Ser Asp Tyr Ser Ile Ala Met Asp Lys Ile His Gln Gln
1               5                   10                  15

Asp Phe Val Asn Trp Lys Leu Ala Gln Lys
            20                  25

<210> SEQ ID NO 40
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 40

Thr Phe Ile Ser Asp Tyr Ser Ile Ala Met Asp Lys Ile His Gln Gln
1               5                   10                  15

Asp Phe Val Asn Trp Leu Lys Ala Gln Lys
            20                  25

<210> SEQ ID NO 41
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(11)
<223> OTHER INFORMATION: GIP analogues

<400> SEQUENCE: 41

Thr Phe Ile Ser Asp Tyr Ser Ile Ala Met Asp Lys Ile His Gln Gln
1               5                   10                  15

Asp Phe Val Asn Trp Leu Leu Lys Gln Lys
            20                  25

<210> SEQ ID NO 42
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 42

Thr Phe Ile Ser Asp Tyr Ser Ile Ala Met Asp Lys Ile His Gln Gln
1               5                   10                  15

Asp Phe Val Asn Trp Leu Leu Ala Lys Lys
            20                  25

<210> SEQ ID NO 43
<211> LENGTH: 26
<212> TYPE: PRT
<213> ORGANISM: Artificial Sequence
<220> FEATURE:
<223> OTHER INFORMATION: GIP analogues

```
<220> FEATURE:
<221> NAME/KEY: PEPTIDE
<222> LOCATION: (1)..(11)
<223> OTHER INFORMATION: GIP analogues

<400> SEQUENCE: 43

Thr Phe Ile Ser Asp Tyr Lys Ile Ala Met Asp Lys Ile Ala Gln Gln
1               5                   10                  15

Asp Phe Val Asn Trp Leu Leu Ala Gln Lys
            20                  25

<210> SEQ ID NO 44
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 44

Thr Phe Ile Ser Asp Tyr Lys Ile Ala Met Asp Lys Ile Arg Gln Gln
1               5                   10                  15

Asp Phe Val Asn Trp Leu Leu Ala Gln Lys
            20                  25

<210> SEQ ID NO 45
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 45

Thr Phe Ile Ser Asp Tyr Lys Ile Ala Met Glu Lys Ile His Gln Gln
1               5                   10                  15

Asp Phe Val Asn Trp Leu Leu Ala Gln Lys
            20                  25

<210> SEQ ID NO 46
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (10)..(10)
<223> OTHER INFORMATION: X = Nle

<400> SEQUENCE: 46

Thr Phe Ile Ser Asp Tyr Lys Ile Ala Xaa Asp Lys Ile His Gln Gln
1               5                   10                  15

Asp Phe Val Asn Trp Leu Leu Ala Gln Lys
            20                  25

<210> SEQ ID NO 47
<211> LENGTH: 26
<212> TYPE: PRT
<213> ORGANISM: Artificial Sequence
<220> FEATURE:
```

<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 47

Thr Phe Ile Ser Asp Tyr Lys Ile Ala Leu Asp Lys Ile His Gln Gln
1               5                   10                  15

Asp Phe Val Asn Trp Leu Leu Ala Gln Lys
            20                  25

<210> SEQ ID NO 48
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 48

Thr Phe Ile Ser Asp Tyr Ser Lys Ala Met Asp Lys Ile Ala Gln Gln
1               5                   10                  15

Asp Phe Val Asn Trp Leu Leu Ala Gln Lys
            20                  25

<210> SEQ ID NO 49
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 49

Thr Phe Ile Ser Asp Tyr Ser Lys Ala Met Asp Lys Ile Arg Gln Gln
1               5                   10                  15

Asp Phe Val Asn Trp Leu Leu Ala Gln Lys
            20                  25

<210> SEQ ID NO 50
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 50

Thr Phe Ile Ser Asp Tyr Ser Lys Ala Met Glu Lys Ile His Gln Gln
1               5                   10                  15

Asp Phe Val Asn Trp Leu Leu Ala Gln Lys
            20                  25

<210> SEQ ID NO 51
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (10)..(10)
<223> OTHER INFORMATION: X=Nle

<400> SEQUENCE: 51

Thr Phe Ile Ser Asp Tyr Ser Lys Ala Xaa Asp Lys Ile His Gln Gln
1               5                   10                  15

Asp Phe Val Asn Trp Leu Leu Ala Gln Lys
            20                  25

<210> SEQ ID NO 52
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 52

Thr Phe Ile Ser Asp Tyr Ser Lys Ala Leu Asp Lys Ile His Gln Gln
1               5                   10                  15

Asp Phe Val Asn Trp Leu Leu Ala Gln Lys
            20                  25

<210> SEQ ID NO 53
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 53

Thr Phe Ile Ser Asp Tyr Ser Ile Lys Met Asp Lys Ile Ala Gln Gln
1               5                   10                  15

Asp Phe Val Asn Trp Leu Leu Ala Gln Lys
            20                  25

<210> SEQ ID NO 54
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 54

Thr Phe Ile Ser Asp Tyr Ser Ile Lys Met Asp Lys Ile Arg Gln Gln
1               5                   10                  15

Asp Phe Val Asn Trp Leu Leu Ala Gln Lys
            20                  25

<210> SEQ ID NO 55
<211> LENGTH: 26
<212> TYPE: PRT

<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 55

Thr Phe Ile Ser Asp Tyr Ser Ile Lys Met Glu Lys Ile His Gln Gln
1               5                   10                  15

Asp Phe Val Asn Trp Leu Leu Ala Gln Lys
            20                  25

<210> SEQ ID NO 56
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (10)..(10)
<223> OTHER INFORMATION: X=Nle

<400> SEQUENCE: 56

Thr Phe Ile Ser Asp Tyr Ser Ile Lys Xaa Asp Lys Ile His Gln Gln
1               5                   10                  15

Asp Phe Val Asn Trp Leu Leu Ala Gln Lys
            20                  25

<210> SEQ ID NO 57
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 57

Thr Phe Ile Ser Asp Tyr Ser Ile Lys Leu Asp Lys Ile His Gln Gln
1               5                   10                  15

Asp Phe Val Asn Trp Leu Leu Ala Gln Lys
            20                  25

<210> SEQ ID NO 58
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 58

Thr Phe Ile Ser Asp Tyr Ser Ile Ala Met Glu Lys Ile Lys Gln Gln
1               5                   10                  15

Asp Phe Val Asn Trp Leu Leu Ala Gln Lys
            20                  25

<210> SEQ ID NO 59
<211> LENGTH: 26

```
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (10)..(10)
<223> OTHER INFORMATION: X=Nle

<400> SEQUENCE: 59

Thr Phe Ile Ser Asp Tyr Ser Ile Ala Xaa Asp Lys Ile Lys Gln Gln
1               5                   10                  15

Asp Phe Val Asn Trp Leu Leu Ala Gln Lys
            20                  25

<210> SEQ ID NO 60
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 60

Thr Phe Ile Ser Asp Tyr Ser Ile Ala Asn Leu Glu Asp Lys Ile Lys
1               5                   10                  15

Gln Gln Asp Phe Val Asn Trp Leu Leu Ala Gln Lys
            20                  25

<210> SEQ ID NO 61
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (11)..(11)
<223> OTHER INFORMATION: X=Orn

<400> SEQUENCE: 61

Thr Phe Ile Ser Asp Tyr Ser Ile Ala Met Xaa Lys Ile His Gln Gln
1               5                   10                  15

Asp Phe Val Asn Trp Leu Leu Ala Gln Lys
            20                  25

<210> SEQ ID NO 62
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (14)..(14)
<223> OTHER INFORMATION: X=Orn

<400> SEQUENCE: 62

Thr Phe Ile Ser Asp Tyr Ser Ile Ala Met Asp Lys Ile Xaa Gln Gln
1               5                   10                  15

Asp Phe Val Asn Trp Leu Leu Ala Gln Lys
            20                  25

<210> SEQ ID NO 63
```

```
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 63

Thr Phe Ile Ser Asp Tyr Ser Ile Ala Leu Asp Arg Ile Lys Gln Gln
1               5                   10                  15

Asp Phe Val Asn Trp Leu Leu Ala Gln Arg
            20                  25

<210> SEQ ID NO 64
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 64

Lys Phe Ile Ser Asp Tyr Ser Ile Ala Met Asp Arg Ile His Gln Gln
1               5                   10                  15

Asp Phe Val Asn Trp Leu Leu Ala Gln Arg
            20                  25

<210> SEQ ID NO 65
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 65

Lys Phe Ile Ser Asp Tyr Ser Ile Ala Met Asp Lys Ile His Gln Gln
1               5                   10                  15

Asp Phe Val Asn Trp Leu Leu Ala Gln Lys
            20                  25

<210> SEQ ID NO 66
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 66

Thr Phe Ile Ser Asp Tyr Lys Ile Ala Met Asp Arg Ile His Gln Gln
1               5                   10                  15

Asp Phe Val Asn Trp Leu Leu Ala Gln Arg
            20                  25
```

```
<210> SEQ ID NO 67
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 67

Thr Phe Ile Ser Asp Tyr Lys Ile Ala Leu Asp Arg Ile His Gln Gln
1               5                   10                  15

Asp Phe Val Asn Trp Leu Leu Ala Gln Arg
            20                  25

<210> SEQ ID NO 68
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 68

Thr Phe Ile Ser Asp Tyr Ser Lys Ala Met Asp Arg Ile His Gln Gln
1               5                   10                  15

Asp Phe Val Asn Trp Leu Leu Ala Gln Arg
            20                  25

<210> SEQ ID NO 69
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 69

Thr Phe Ile Ser Asp Tyr Ser Lys Ala Leu Asp Arg Ile His Gln Gln
1               5                   10                  15

Asp Phe Val Asn Trp Leu Leu Ala Gln Arg
            20                  25

<210> SEQ ID NO 70
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 70

Thr Phe Ile Ser Asp Tyr Ser Ile Lys Met Asp Arg Ile His Gln Gln
1               5                   10                  15

Asp Phe Val Asn Trp Leu Leu Ala Gln Arg
            20                  25
```

<210> SEQ ID NO 71
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 71

Thr Phe Ile Ser Asp Tyr Ser Ile Lys Leu Asp Arg Ile His Gln Gln
1               5                   10                  15

Asp Phe Val Asn Trp Leu Leu Ala Gln Arg
            20                  25

<210> SEQ ID NO 72
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 72

Glu Gly Thr Phe Ile Ser Asp Tyr Ser Ile Ala Met Asp Arg Ile Lys
1               5                   10                  15

Gln Gln Asp Phe Val Asn Trp Leu Leu Ala Gln Arg
            20                  25

<210> SEQ ID NO 73
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 73

Glu Gly Thr Phe Ile Ser Asp Tyr Ser Ile Ala Met Asp Arg Ile His
1               5                   10                  15

Gln Gln Asp Phe Val Asn Trp Leu Leu Ala Gln Arg
            20                  25

<210> SEQ ID NO 74
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 74

Glu Gly Thr Phe Ile Ser Asp Tyr Ser Ile Ala Met Asp Lys Ile Ala
1               5                   10                  15

Gln Gln Asp Phe Val Asn Trp Leu Leu Ala Gln Lys
            20                  25

<210> SEQ ID NO 75
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 75

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys
            20                  25

<210> SEQ ID NO 76
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 76

Glu Gly Thr Phe Ile Ser Asp Tyr Ser Ile Ala Met Glu Lys Ile Ala
1               5                   10                  15

Gln Gln Asp Phe Val Asn Trp Leu Leu Ala Gln Lys
            20                  25

<210> SEQ ID NO 77
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 77

Glu Gly Thr Phe Ile Ser Asp Tyr Ser Ile Ala Met Asp Ala Ile Ala
1               5                   10                  15

Gln Gln Asp Phe Val Asn Trp Leu Leu Ala Gln Lys
            20                  25

<210> SEQ ID NO 78
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 78

Glu Gly Thr Phe Ile Ser Asp Tyr Ser Ile Ala Met Glu Lys Ile His
1               5                   10                  15

Gln Gln Asp Phe Val Asn Trp Leu Leu Ala Gln Lys 20                  25

<210> SEQ ID NO 79
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 79

Glu Gly Thr Phe Ile Ser Asp Tyr Ser Ile Ala Met Asn Lys Ile His
1               5                   10                  15

Gln Gln Asp Phe Val Asn Trp Leu Leu Ala Gln Lys
            20                  25

<210> SEQ ID NO 80
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 80

Glu Gly Thr Phe Ile Ser Asp Tyr Ser Ile Ala Met Asp Ala Ile His
1               5                   10                  15

Gln Gln Asp Phe Val Asn Trp Leu Leu Ala Gln Lys
            20                  25

<210> SEQ ID NO 81
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 81

Glu Gly Thr Phe Ile Ser Asp Tyr Ser Ile Ala Met Asp His Ile His
1               5                   10                  15

Gln Gln Asp Phe Val Asn Trp Leu Leu Ala Gln Lys
            20                  25

<210> SEQ ID NO 82
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 82

Glu Gly Thr Phe Ile Ser Asp Tyr Ser Ile Ala Met Asp Arg Ile His
1               5                   10                  15

```
Gln Gln Asp Phe Val Asn Trp Leu Leu Ala Gln Lys
            20                  25

<210> SEQ ID NO 83
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 83

Glu Gly Thr Phe Ile Ser Asp Tyr Ser Ile Ala Met Asp Lys Ile Phe
1               5                   10                  15

Gln Gln Asp Phe Val Asn Trp Leu Leu Ala Gln Lys
            20                  25

<210> SEQ ID NO 84
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 84

Glu Gly Thr Phe Ile Ser Asp Tyr Ser Ile Ala Met Asp Lys Ile Trp
1               5                   10                  15

Gln Gln Asp Phe Val Asn Trp Leu Leu Ala Gln Lys
            20                  25

<210> SEQ ID NO 85
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 85

Glu Gly Thr Phe Ile Ser Asp Tyr Ser Ile Ala Met Asp Lys Ile His
1               5                   10                  15

Gln Gln Asp Phe Val Asn Trp Leu Leu Ala Gln Arg
            20                  25

<210> SEQ ID NO 86
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 86

Glu Gly Thr Phe Ile Ser Asp Tyr Ser Ile Ala Met Asp Lys Ile His
1               5                   10                  15
```

Gln Gln Asp Phe Val Asn Trp Leu Leu Ala Gln His
            20                  25

<210> SEQ ID NO 87
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 87

Glu Lys Thr Phe Ile Ser Asp Tyr Ser Ile Ala Met Asp Lys Ile His
1               5                   10                  15

Gln Gln Asp Phe Val Asn Trp Leu Leu Ala Gln Lys
            20                  25

<210> SEQ ID NO 88
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 88

Glu Gly Lys Phe Ile Ser Asp Tyr Ser Ile Ala Met Asp Lys Ile His
1               5                   10                  15

Gln Gln Asp Phe Val Asn Trp Leu Leu Ala Gln Lys
            20                  25

<210> SEQ ID NO 89
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 89

Glu Gly Thr Lys Ile Ser Asp Tyr Ser Ile Ala Met Asp Lys Ile His
1               5                   10                  15

Gln Gln Asp Phe Val Asn Trp Leu Leu Ala Gln Lys
            20                  25

<210> SEQ ID NO 90
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 90

Glu Gly Thr Phe Lys Ser Asp Tyr Ser Ile Ala Met Asp Lys Ile His

```
                1               5                   10                  15

Gln Gln Asp Phe Val Asn Trp Leu Leu Ala Gln Lys
            20                  25

<210> SEQ ID NO 91
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 91

Glu Gly Thr Phe Ile Lys Asp Tyr Ser Ile Ala Met Asp Lys Ile His
1               5                   10                  15

Gln Gln Asp Phe Val Asn Trp Leu Leu Ala Gln Lys
            20                  25

<210> SEQ ID NO 92
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 92

Glu Gly Thr Phe Ile Ser Lys Tyr Ser Ile Ala Met Asp Lys Ile His
1               5                   10                  15

Gln Gln Asp Phe Val Asn Trp Leu Leu Ala Gln Lys
            20                  25

<210> SEQ ID NO 93
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 93

Glu Gly Thr Phe Ile Ser Asp Lys Ser Ile Ala Met Asp Lys Ile His
1               5                   10                  15

Gln Gln Asp Phe Val Asn Trp Leu Leu Ala Gln Lys
            20                  25

<210> SEQ ID NO 94
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 94
```

```
Glu Gly Thr Phe Ile Ser Asp Tyr Lys Ile Ala Met Asp Lys Ile His
1               5                   10                  15

Gln Gln Asp Phe Val Asn Trp Leu Leu Ala Gln Lys
            20                  25
```

<210> SEQ ID NO 95
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 95

```
Glu Gly Thr Phe Ile Ser Asp Tyr Ser Lys Ala Met Asp Lys Ile His
1               5                   10                  15

Gln Gln Asp Phe Val Asn Trp Leu Leu Ala Gln Lys
            20                  25
```

<210> SEQ ID NO 96
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 96

```
Glu Gly Thr Phe Ile Ser Asp Tyr Ser Ile Lys Met Asp Lys Ile His
1               5                   10                  15

Gln Gln Asp Phe Val Asn Trp Leu Leu Ala Gln Lys
            20                  25
```

<210> SEQ ID NO 97
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 97

```
Glu Gly Thr Phe Ile Ser Asp Tyr Ser Ile Ala Lys Asp Lys Ile His
1               5                   10                  15

Gln Gln Asp Phe Val Asn Trp Leu Leu Ala Gln Lys
            20                  25
```

<210> SEQ ID NO 98
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 98

Glu Gly Thr Phe Ile Ser Asp Tyr Ser Ile Ala Met Lys Lys Ile His
1               5                   10                  15

Gln Gln Asp Phe Val Asn Trp Leu Leu Ala Gln Lys
            20                  25

<210> SEQ ID NO 99
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 99

Glu Gly Thr Phe Ile Ser Asp Tyr Ser Ile Ala Met Asp Lys Lys His
1               5                   10                  15

Gln Gln Asp Phe Val Asn Trp Leu Leu Ala Gln Lys
            20                  25

<210> SEQ ID NO 100
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 100

Glu Gly Thr Phe Ile Ser Asp Tyr Ser Ile Ala Met Asp Lys Ile His
1               5                   10                  15

Lys Gln Asp Phe Val Asn Trp Leu Leu Ala Gln Lys
            20                  25

<210> SEQ ID NO 101
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 101

Glu Gly Thr Phe Ile Ser Asp Tyr Ser Ile Ala Met Asp Lys Ile His
1               5                   10                  15

Gln Lys Asp Phe Val Asn Trp Leu Leu Ala Gln Lys
            20                  25

<210> SEQ ID NO 102
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 102

Glu Gly Thr Phe Ile Ser Asp Tyr Ser Ile Ala Met Asp Lys Ile His
1               5                   10                  15

Gln Gln Lys Phe Val Asn Trp Leu Leu Ala Gln Lys
            20                  25

<210> SEQ ID NO 103
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 103

Glu Gly Thr Phe Ile Ser Asp Tyr Ser Ile Ala Met Asp Lys Ile His
1               5                   10                  15

Gln Gln Asp Lys Val Asn Trp Leu Leu Ala Gln Lys
            20                  25

<210> SEQ ID NO 104
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 104

Glu Gly Thr Phe Ile Ser Asp Tyr Ser Ile Ala Met Asp Lys Ile His
1               5                   10                  15

Gln Gln Asp Phe Lys Asn Trp Leu Leu Ala Gln Lys
            20                  25

<210> SEQ ID NO 105
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 105

Glu Gly Thr Phe Ile Ser Asp Tyr Ser Ile Ala Met Asp Lys Ile His
1               5                   10                  15

Gln Gln Asp Phe Val Lys Trp Leu Leu Ala Gln Lys
            20                  25

<210> SEQ ID NO 106
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 106

Glu Gly Thr Phe Ile Ser Asp Tyr Ser Ile Ala Met Asp Lys Ile His
1               5                   10                  15

Gln Gln Asp Phe Val Asn Lys Leu Leu Ala Gln Lys
            20                  25

<210> SEQ ID NO 107
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 107

Glu Gly Thr Phe Ile Ser Asp Tyr Ser Ile Ala Met Asp Lys Ile His
1               5                   10                  15

Gln Gln Asp Phe Val Asn Trp Lys Leu Ala Gln Lys
            20                  25

<210> SEQ ID NO 108
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 108

Glu Gly Thr Phe Ile Ser Asp Tyr Ser Ile Ala Met Asp Lys Ile His
1               5                   10                  15

Gln Gln Asp Phe Val Asn Trp Leu Lys Ala Gln Lys
            20                  25

<210> SEQ ID NO 109
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 109

Glu Gly Thr Phe Ile Ser Asp Tyr Ser Ile Ala Met Asp Lys Ile His
1               5                   10                  15

Gln Gln Asp Phe Val Asn Trp Leu Leu Lys Gln Lys
            20                  25

<210> SEQ ID NO 110
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)

```
<223> OTHER INFORMATION: GIP analogues

<400> SEQUENCE: 110

Glu Gly Thr Phe Ile Ser Asp Tyr Ser Ile Ala Met Asp Lys Ile His
1               5                   10                  15

Gln Gln Asp Phe Val Asn Trp Leu Leu Ala Lys Lys
            20                  25

<210> SEQ ID NO 111
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 111

Glu Gly Thr Phe Ile Ser Asp Tyr Lys Ile Ala Met Asp Lys Ile Ala
1               5                   10                  15

Gln Gln Asp Phe Val Asn Trp Leu Leu Ala Gln Lys
            20                  25

<210> SEQ ID NO 112
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 112

Glu Gly Thr Phe Ile Ser Asp Tyr Lys Ile Ala Met Asp Lys Ile Arg
1               5                   10                  15

Gln Gln Asp Phe Val Asn Trp Leu Leu Ala Gln Lys
            20                  25

<210> SEQ ID NO 113
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 113

Glu Gly Thr Phe Ile Ser Asp Tyr Lys Ile Ala Met Glu Lys Ile His
1               5                   10                  15

Gln Gln Asp Phe Val Asn Trp Leu Leu Ala Gln Lys
            20                  25

<210> SEQ ID NO 114
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
```

```
<222> LOCATION: (12)..(12)
<223> OTHER INFORMATION: X=Nle

<400> SEQUENCE: 114

Glu Gly Thr Phe Ile Ser Asp Tyr Lys Ile Ala Xaa Asp Lys Ile His
1               5                   10                  15
Gln Gln Asp Phe Val Asn Trp Leu Leu Ala Gln Lys
            20                  25

<210> SEQ ID NO 115
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 115

Glu Gly Thr Phe Ile Ser Asp Tyr Lys Ile Ala Leu Asp Lys Ile His
1               5                   10                  15
Gln Gln Asp Phe Val Asn Trp Leu Leu Ala Gln Lys
            20                  25

<210> SEQ ID NO 116
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 116

Glu Gly Thr Phe Ile Ser Asp Tyr Ser Lys Ala Met Asp Lys Ile Ala
1               5                   10                  15
Gln Gln Asp Phe Val Asn Trp Leu Leu Ala Gln Lys
            20                  25

<210> SEQ ID NO 117
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 117

Glu Gly Thr Phe Ile Ser Asp Tyr Ser Lys Ala Met Asp Lys Ile Arg
1               5                   10                  15
Gln Gln Asp Phe Val Asn Trp Leu Leu Ala Gln Lys
            20                  25

<210> SEQ ID NO 118
<211> LENGTH: 28
<212> TYPE: PRT
<213> ORGANISM: Artificial Sequence
<220> FEATURE:
<223> OTHER INFORMATION: GIP analogues
<220> FEATURE:
```

```
<221> NAME/KEY: PEPTIDE
<222> LOCATION: (1)..(1)
<223> OTHER INFORMATION: GIP analogues

<400> SEQUENCE: 118

Glu Gly Thr Phe Ile Ser Asp Tyr Ser Lys Ala Met Glu Lys Ile His
1               5                   10                  15

Gln Gln Asp Phe Val Asn Trp Leu Leu Ala Gln Lys
            20                  25

<210> SEQ ID NO 119
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (12)..(12)
<223> OTHER INFORMATION: X=Nle

<400> SEQUENCE: 119

Glu Gly Thr Phe Ile Ser Asp Tyr Ser Lys Ala Xaa Asp Lys Ile His
1               5                   10                  15

Gln Gln Asp Phe Val Asn Trp Leu Leu Ala Gln Lys
            20                  25

<210> SEQ ID NO 120
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 120

Glu Gly Thr Phe Ile Ser Asp Tyr Ser Lys Ala Leu Asp Lys Ile His
1               5                   10                  15

Gln Gln Asp Phe Val Asn Trp Leu Leu Ala Gln Lys
            20                  25

<210> SEQ ID NO 121
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 121

Glu Gly Thr Phe Ile Ser Asp Tyr Ser Ile Lys Met Asp Lys Ile Ala
1               5                   10                  15

Gln Gln Asp Phe Val Asn Trp Leu Leu Ala Gln Lys
            20                  25

<210> SEQ ID NO 122
<211> LENGTH: 28
<212> TYPE: PRT
<213> ORGANISM: Artificial Sequence
<220> FEATURE:
<223> OTHER INFORMATION: GIP analogues
```

```
<220> FEATURE:
<221> NAME/KEY: PEPTIDE
<222> LOCATION: (1)..(1)
<223> OTHER INFORMATION: GIP analogues

<400> SEQUENCE: 122

Glu Gly Thr Phe Ile Ser Asp Tyr Ser Ile Lys Met Asp Lys Ile Arg
1               5                   10                  15

Gln Gln Asp Phe Val Asn Trp Leu Leu Ala Gln Lys
            20                  25

<210> SEQ ID NO 123
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 123

Glu Gly Thr Phe Ile Ser Asp Tyr Ser Ile Lys Met Glu Lys Ile His
1               5                   10                  15

Gln Gln Asp Phe Val Asn Trp Leu Leu Ala Gln Lys
            20                  25

<210> SEQ ID NO 124
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (12)..(12)
<223> OTHER INFORMATION: X=Nle

<400> SEQUENCE: 124

Glu Gly Thr Phe Ile Ser Asp Tyr Ser Ile Lys Xaa Asp Lys Ile His
1               5                   10                  15

Gln Gln Asp Phe Val Asn Trp Leu Leu Ala Gln Lys
            20                  25

<210> SEQ ID NO 125
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 125

Glu Gly Thr Phe Ile Ser Asp Tyr Ser Ile Lys Leu Asp Lys Ile His
1               5                   10                  15

Gln Gln Asp Phe Val Asn Trp Leu Leu Ala Gln Lys
            20                  25

<210> SEQ ID NO 126
<211> LENGTH: 28
<212> TYPE: PRT
<213> ORGANISM: Artificial Sequence
<220> FEATURE:
```

```
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 126

Glu Gly Thr Phe Ile Ser Asp Tyr Ser Ile Ala Met Glu Lys Ile Lys
1               5                   10                  15

Gln Gln Asp Phe Val Asn Trp Leu Leu Ala Gln Lys
            20                  25

<210> SEQ ID NO 127
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (12)..(12)
<223> OTHER INFORMATION: X=Nle

<400> SEQUENCE: 127

Glu Gly Thr Phe Ile Ser Asp Tyr Ser Ile Ala Xaa Asp Lys Ile Lys
1               5                   10                  15

Gln Gln Asp Phe Val Asn Trp Leu Leu Ala Gln Lys
            20                  25

<210> SEQ ID NO 128
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 128

Glu Gly Thr Phe Ile Ser Asp Tyr Ser Ile Ala Leu Asp Lys Ile Lys
1               5                   10                  15

Gln Gln Asp Phe Val Asn Trp Leu Leu Ala Gln Lys
            20                  25

<210> SEQ ID NO 129
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 129

Glu Gly Lys Phe Ile Ser Asp Tyr Ser Ile Ala Met Asp Arg Ile His
1               5                   10                  15

Gln Gln Asp Phe Val Asn Trp Leu Leu Ala Gln Arg
            20                  25

<210> SEQ ID NO 130
<211> LENGTH: 28
<212> TYPE: PRT
<213> ORGANISM: Artificial Sequence
```

```
<220> FEATURE:
<223> OTHER INFORMATION: GIP analogues
<220> FEATURE:
<221> NAME/KEY: PEPTIDE
<222> LOCATION: (13)..(13)
<223> OTHER INFORMATION: X=Orn

<400> SEQUENCE: 130

Glu Gly Thr Phe Ile Ser Asp Tyr Ser Ile Ala Met Xaa Lys Ile His
1               5                   10                  15

Gln Gln Asp Phe Val Asn Trp Leu Leu Ala Gln Lys
            20                  25

<210> SEQ ID NO 131
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (16)..(16)
<223> OTHER INFORMATION: X=Orn

<400> SEQUENCE: 131

Glu Gly Thr Phe Ile Ser Asp Tyr Ser Ile Ala Met Asp Lys Ile Xaa
1               5                   10                  15

Gln Gln Asp Phe Val Asn Trp Leu Leu Ala Gln Lys
            20                  25

<210> SEQ ID NO 132
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 132

Glu Gly Thr Phe Ile Ser Asp Tyr Ser Ile Ala Leu Asp Arg Ile Lys
1               5                   10                  15

Gln Gln Asp Phe Val Asn Trp Leu Leu Ala Gln Arg
            20                  25

<210> SEQ ID NO 133
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (7)..(7)
<223> OTHER INFORMATION: X=Orn

<400> SEQUENCE: 133

Thr Phe Ile Ser Asp Tyr Xaa Ile Ala Met Asp Lys Ile His Gln Gln
1               5                   10                  15

Asp Phe Val Asn Trp Leu Leu Ala Gln Lys
            20                  25

<210> SEQ ID NO 134
<211> LENGTH: 28
<212> TYPE: PRT
```

```
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (9)..(9)
<223> OTHER INFORMATION: X=Orn

<400> SEQUENCE: 134

Glu Gly Thr Phe Ile Ser Asp Tyr Xaa Ile Ala Met Asp Lys Ile His
1               5                   10                  15

Gln Gln Asp Phe Val Asn Trp Leu Leu Ala Gln Lys
            20                  25

<210> SEQ ID NO 135
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (8)..(8)
<223> OTHER INFORMATION: X=Orn

<400> SEQUENCE: 135

Thr Phe Ile Ser Asp Tyr Ser Xaa Ala Met Asp Lys Ile His Gln Gln
1               5                   10                  15

Asp Phe Val Asn Trp Leu Leu Ala Gln Lys
            20                  25

<210> SEQ ID NO 136
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (10)..(10)
<223> OTHER INFORMATION: X=Orn

<400> SEQUENCE: 136

Glu Gly Thr Phe Ile Ser Asp Tyr Ser Xaa Ala Met Asp Lys Ile His
1               5                   10                  15

Gln Gln Asp Phe Val Asn Trp Leu Leu Ala Gln Lys
            20                  25

<210> SEQ ID NO 137
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (9)..(9)
<223> OTHER INFORMATION: X=Orn

<400> SEQUENCE: 137

Thr Phe Ile Ser Asp Tyr Ser Ile Xaa Met Asp Lys Ile His Gln Gln
1               5                   10                  15

Asp Phe Val Asn Trp Leu Leu Ala Gln Lys
            20                  25

<210> SEQ ID NO 138
<211> LENGTH: 28
```

```
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (11)..(11)
<223> OTHER INFORMATION: X=Orn

<400> SEQUENCE: 138

Glu Gly Thr Phe Ile Ser Asp Tyr Ser Ile Xaa Met Asp Lys Ile His
1               5                   10                  15

Gln Gln Asp Phe Val Asn Trp Leu Leu Ala Gln Lys
            20                  25

<210> SEQ ID NO 139
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (17)..(17)
<223> OTHER INFORMATION: X=Orn

<400> SEQUENCE: 139

Thr Phe Ile Ser Asp Tyr Ser Ile Ala Met Asp Lys Ile His Gln Gln
1               5                   10                  15

Xaa Phe Val Asn Trp Leu Leu Ala Gln Lys
            20                  25

<210> SEQ ID NO 140
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (19)..(19)
<223> OTHER INFORMATION: X=Orn

<400> SEQUENCE: 140

Glu Gly Thr Phe Ile Ser Asp Tyr Ser Ile Ala Met Asp Lys Ile His
1               5                   10                  15

Gln Gln Xaa Phe Val Asn Trp Leu Leu Ala Gln Lys
            20                  25

<210> SEQ ID NO 141
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (3)..(3)
<223> OTHER INFORMATION: X=Orn

<400> SEQUENCE: 141

Glu Gly Xaa Phe Ile Ser Asp Tyr Ser Ile Ala Met Asp Lys Ile His
1               5                   10                  15

Gln Gln Lys Phe Val Asn Trp Leu Leu Ala Gln Lys
            20                  25

<210> SEQ ID NO 142
```

```
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (13)..(13)
<223> OTHER INFORMATION: X=Orn

<400> SEQUENCE: 142

Glu Gly Thr Phe Ile Ser Asp Tyr Ser Ile Ala Met Xaa Lys Ile His
1               5                   10                  15

Gln Gln Lys Phe Val Asn Trp Leu Leu Ala Gln Lys
            20                  25

<210> SEQ ID NO 143
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (18)..(18)
<223> OTHER INFORMATION: X=Orn

<400> SEQUENCE: 143

Glu Gly Thr Phe Ile Ser Asp Tyr Ser Ile Ala Met Asp Lys Ile His
1               5                   10                  15

Gln Xaa Lys Phe Val Asn Trp Leu Leu Ala Gln Lys
            20                  25

<210> SEQ ID NO 144
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 144

Glu Gly Trp Phe Ile Ser Asp Tyr Ser Ile Ala Met Glu Lys Ile Ala
1               5                   10                  15

Gln Gln Asp Phe Val Asn Trp Leu Leu Ala Gln Lys
            20                  25

<210> SEQ ID NO 145
<211> LENGTH: 26
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 145

Thr Phe Ile Ser Asp Tyr Ser Ile Ala Met Asp Arg Ile His Gln Gln
1               5                   10                  15

Lys Phe Val Asn Trp Leu Leu Ala Gln Arg
            20                  25
```

```
<210> SEQ ID NO 146
<211> LENGTH: 28
<212> TYPE: PRT
<213> ORGANISM: Artificial Sequence
<220> FEATURE:
<223> OTHER INFORMATION: GIP analogues
<220> FEATURE:
<221> NAME/KEY: PEPTIDE
<222> LOCATION: (1)..(1)
<223> OTHER INFORMATION: GIP analogues

<400> SEQUENCE: 146

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Arg
            20                  25

<210> SEQ ID NO 147
<211> LENGTH: 25
<212> TYPE: PRT
<213> ORGANISM: Artificial Sequence
<220> FEATURE:
<223> OTHER INFORMATION: hGIP6-30
<220> FEATURE:
<221> NAME/KEY: PEPTIDE
<222> LOCATION: (1)..(1)
<223> OTHER INFORMATION: hGIP6-30

<400> SEQUENCE: 147

Phe Ile Ser Asp Tyr Ser Ile Ala Met Asp Lys Ile His Gln Gln Asp
1               5                   10                  15

Phe Val Asn Trp Leu Leu Ala Gln Lys
            20                  25

<210> SEQ ID NO 148
<211> LENGTH: 27
<212> TYPE: PRT
<213> ORGANISM: Artificial Sequence
<220> FEATURE:
<223> OTHER INFORMATION: hGIP4-30
<220> FEATURE:
<221> NAME/KEY: PEPTIDE
<222> LOCATION: (1)..(1)
<223> OTHER INFORMATION: hGIP4-30

<400> SEQUENCE: 148

Gly Thr Phe Ile Ser Asp Tyr Ser Ile Ala Met Asp Lys Ile His Gln
1               5                   10                  15

Gln Asp Phe Val Asn Trp Leu Leu Ala Gln Lys
            20                  25

<210> SEQ ID NO 149
<211> LENGTH: 26
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: 1,16-Hexadecanedioic acid is attached to Thr 1

<400> SEQUENCE: 149

Thr Phe Ile Ser Asp Tyr Ser Ile Ala Met Asp Lys Ile His Gln Gln
1               5                   10                  15

Asp Phe Val Asn Trp Leu Leu Ala Gln Lys
            20                  25
```

```
<210> SEQ ID NO 150
<211> LENGTH: 28
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (16)..(16)
<223> OTHER INFORMATION: Palm is attached to Lys 16

<400> SEQUENCE: 150

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys
            20                  25

<210> SEQ ID NO 151
<211> LENGTH: 26
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (14)..(14)
<223> OTHER INFORMATION: 1,16-Hexadecanedioic acid is attached to Lys 14

<400> SEQUENCE: 151

Thr Phe Ile Ser Asp Tyr Ser Ile Ala Met Asp Lys Ile Lys Gln Gln
1               5                   10                  15

Asp Phe Val Asn Trp Leu Leu Ala Gln Lys
            20                  25

<210> SEQ ID NO 152
<211> LENGTH: 26
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (26)..(26)
<223> OTHER INFORMATION: Palm is attached to Lys 26

<400> SEQUENCE: 152

Thr Phe Ile Ser Asp Tyr Ser Ile Ala Met Asp Lys Ile His Gln Gln
1               5                   10                  15

Asp Phe Val Asn Trp Leu Leu Ala Gln Lys
            20                  25

<210> SEQ ID NO 153
<211> LENGTH: 28
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (16)..(16)
<223> OTHER INFORMATION: (gamma-Glu)-Palm is attached to Lys 16

<400> SEQUENCE: 153

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys
            20                  25
```

```
<210> SEQ ID NO 154
<211> LENGTH: 28
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (16)..(16)
<223> OTHER INFORMATION: (4-Abu)-Palm is attached to Lys 16

<400> SEQUENCE: 154

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys
            20                  25

<210> SEQ ID NO 155
<211> LENGTH: 28
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (16)..(16)
<223> OTHER INFORMATION: (Beta-Ala)-Palm is attached to Lys 16

<400> SEQUENCE: 155

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys
            20                  25

<210> SEQ ID NO 156
<211> LENGTH: 28
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (16)..(16)
<223> OTHER INFORMATION: (Gamma-Glu)-AEEAc-Palm is attached to Lys 16

<400> SEQUENCE: 156

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys
            20                  25
```

LONG-ACTING GIP PEPTIDE ANALOGUES

CROSS-REFERENCE TO RELATED APPLICATION

The present application is a U.S. National Phase Application of PCT International Application No. PCT/EP2018/064355, filed on May 31, 2018, designating the United States of America, which is an International Application of and claims the benefit of priority to European Patent Application Serial No. 17173628.3, filed on May 31, 2017. The disclosure of the above-referenced applications are herein expressly incorporated by reference it their entireties, including any drawings.

INCORPORATION OF THE SEQUENCE LISTING

This application contains a Sequence Listing which is hereby incorporated by reference in its entirety. The accompanying Sequence Listing text file, named 059433-502N01US_Sequence Listing_ST25.txt, was created on May 27, 2022 and is 64 KB.

TECHNICAL FIELD

The present invention relates to glucose-dependent insulinotropic peptide (GIP)-derived peptide analogues which are antagonists of the GIP receptor, which comprises a GIP peptide and at least one fatty acid molecule attached to increase half-life while maintaining antagonistic properties.

BACKGROUND

Glucose-dependent insulinotropic peptide (GIP) is a hormone secreted from the K cells of the gut following a meal[1]. Like its sister hormone glucagon-like peptide 1 (GLP-1), GIP is a potent insulin secretagogue[2]. In contrast to the glucagonostatic effect of GLP-1[3, 4], GIP has been shown to display glucagon-releasing properties under certain conditions ([3, 5-13]). The interest in understanding the biology of GIP was intensified by the association between rodent GIPR (GIP receptor) and adiposity[14-21]. In humans, although less clear, there is likewise evidence for a role of GIP in fat metabolism with the demonstration of the GIPR expression in adipose tissue[22], an association between high BMI and increased GIP levels[22, 23], increased adipose tissue blood flow and TAG (triacylglycerol) deposition following GIP administration in a state of high insulin and high glucose[24], decreased basal and postprandial GIP levels observed in obese children put on a diet[25], and increased fasting GIP levels observed in healthy young men put on a high fat diet[26].

Thus, in addition to the general demand from researchers who witnessed the advances in the understanding of GLP-1 following the discovery of the GLP-1 receptor antagonist, exendin(9-39)[27, 28], the potential as an anti-obesity agent has attracted additional attention for the development of potent GIPR antagonists. Many different strategies have been undertaken in order to antagonize GIP's function, e.g. a small molecule receptor antagonist[29], immunization against GIP[30-32] various truncations and mutations of the GIP molecule with antagonistic properties[33-39], and recently a potent antagonist antibody against the GIPR[40].

Under physiological conditions the 42 amino acid hormone, GIP, is degraded by the enzyme dipeptidylpeptidase 4 (DPP-4), which cleaves at the third position of the GIP molecule to yield GIP3-42. Synthetic porcine GIP3-42 displayed no antagonist properties in pigs or perfused rat pancreata in physiological concentrations while in vitro it antagonized the human GIPR[41]. Many peptide hormones are post-translationally modified resulting in various biological forms with different lengths and amino acid modifications[42, 43] Thus, it has been shown that GIP1-30 is produced as a result of post-translational processing[44] and that it is an agonist on the GIPR[33, 45]. If GIP1-30 is secreted into the circulation in humans, the cleavage catalyzed by DPP-4 would result in GIP3-30.

U.S. Pat. No. 7,875,587 discloses GIP receptor antagonists derived from GIP(1-42) having enhanced resistance to degradation by DPP-4, and their use for treatment of insulin resistance and obesity. In WO2004/067548 DPP-4 metabolites are modified by covalent coupling of a pharmacophore to achieve the longer half-life associated with the peptide metabolites and to retain the biological activity of the cleaved peptides similar to the native peptides, including GIP. WO2012/055770 discloses GIP(3-42) as an endogenous metabolite that is readily cleared and with GIPR antagonist effects, and GIP(2-30) as an example of a truncated GIP analogue with GIPR agonist activity. WO1998/24464 discloses the antagonist GIP(7-30). WO 2016/034186 and Hansen et al. 2016 discloses the antagonists GIP(3-30) and GIP(5-30). Pathak et al. 2015 discloses GIP(3-30) which is C-terminally modified with the 9-amino acid Cex from exendin(1-39) and a lysine-residue modified with palmitoyl.

A range of different approaches have been used for modifying the structure of GLP-1 compounds in order to provide a longer duration of action in vivo. These include introduction of a lipophilic substituent to an amino acid residue (WO 96/29342 and WO 98/08871) and acylated GLP-1 analogs (WO 00/34331). WO 02/46227 discloses GLP-1 and exendin-4 analogs fused to human serum albumin in order to extend in vivo half-life.

SUMMARY

The present inventors have identified GIP peptide analogues of GIP(3-30) and GIP(5-30) which are modified by fatty acylation to increase peptide half-life ($T_{1/2}$) while retaining their highly potent GIPR antagonistic properties. Surprisingly the acylation cannot occur at the C-terminal position 30 of GIP(3-30) and GIP(5-30) while retaining the GIPR antagonistic properties.

In one aspect, the invention relates to a glucose-dependent insulinotropic peptide (GIP) analogue of formula 1: TFIS-DYSIAMDKIHQQDFVNWLLAQK (hGIP5-30, SEQ ID NO:1) or formula 2: EGTFISDYSIAMD-KIHQQDFVNWLLAQK (hGIP3-30, SEQ ID NO:2),
or a functional variant having at least 75% sequence identity to any one of SEQ ID NO:1 and SEQ ID NO:2,
wherein said peptide is modified by attaching at least one fatty acid molecule at one or more amino acid residues of any one of SEQ ID NO:1 and SEQ ID NO:2, or a functional variant having at least 75% sequence identity to any one of SEQ ID NO:1 and SEQ ID NO:2,
with the proviso that said at least one fatty acid molecule is not attached to the amino acid residue at position 26 of SEQ ID NO:1 or position 28 of SEQ ID NO:2, or a functional variant having at least 75% sequence identity to any one of SEQ ID NO:1 and SEQ ID NO:2.

In another aspect, the invention relates to the use of such GIP peptide analogues as a medicament.

In yet another aspect, the invention relates to the use of such GIP peptide analogues in a method of antagonizing a GIP receptor; or treating metabolic disorders (or metabolic syndrome), such as obesity, over-weight, diabetes mellitus, insulin resistance and fatty acid metabolism disorder. In other aspects the invention relates to methods of treating cancer. In other aspects the invention relates to methods of treating a bone volume/density disorder.

cAMP accumulation in transiently transfected COS-7 cells expressing the human GIP receptor was assessed following incubation with lys-scanned GIP(5-30)$NH_2$ coupled with C16-diacid on the lysine.

Figure 2:
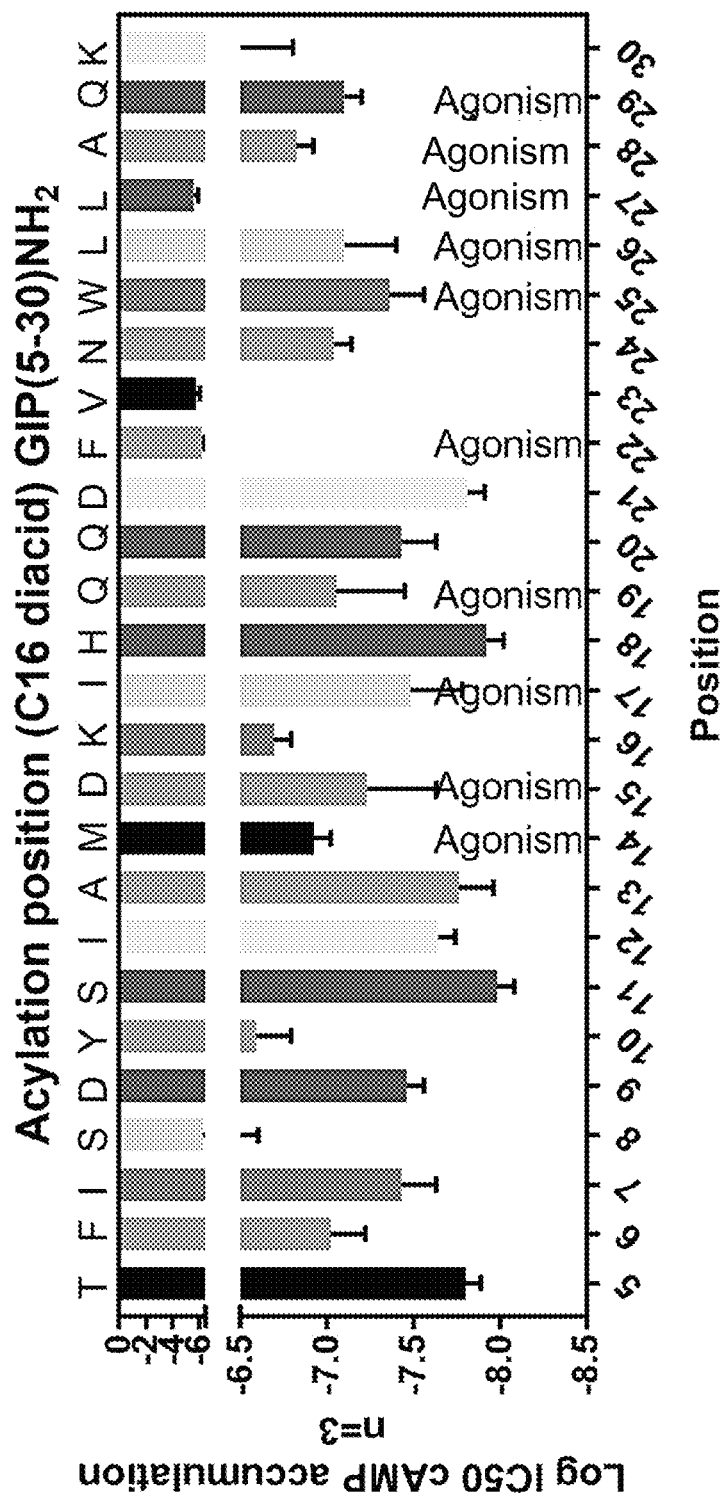

FIG. 2. Lysine (Lys) scan coupled with C16-diacid of GIP(3-30)$NH_2$ from position 5 to position 30 shows highly promising lipidation sites for the development of high potent, long-acting GIP receptor antagonists.

cAMP accumulation in transiently transfected COS-7 cells expressing the human GIP receptor was assessed following incubation with lys-scanned GIP(3-30)$NH_2$ coupled with C16-diacid on the lysine.

Figure 3:
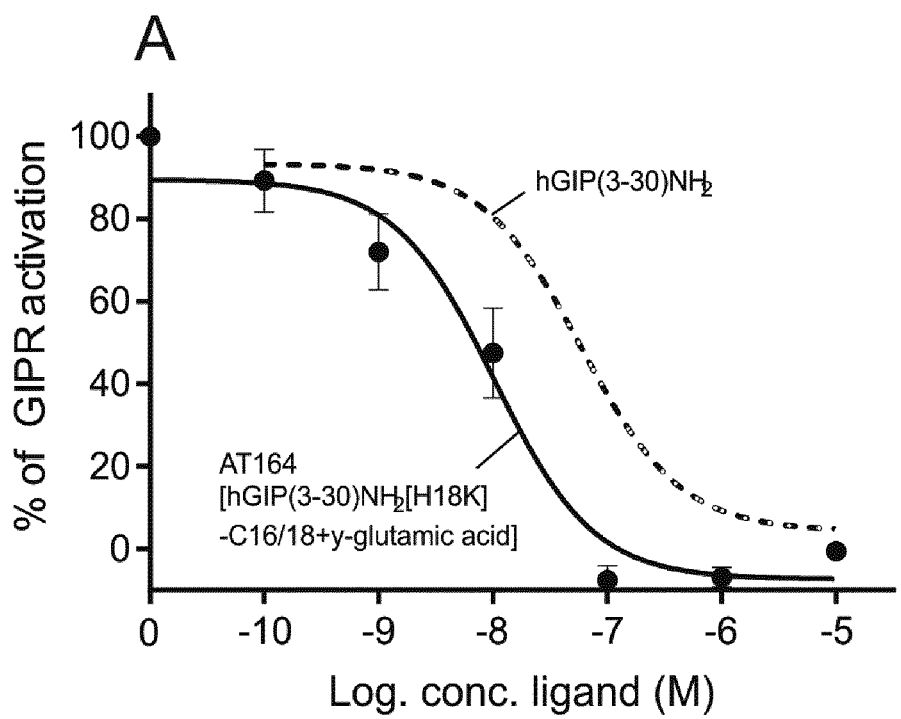
Figure 3:
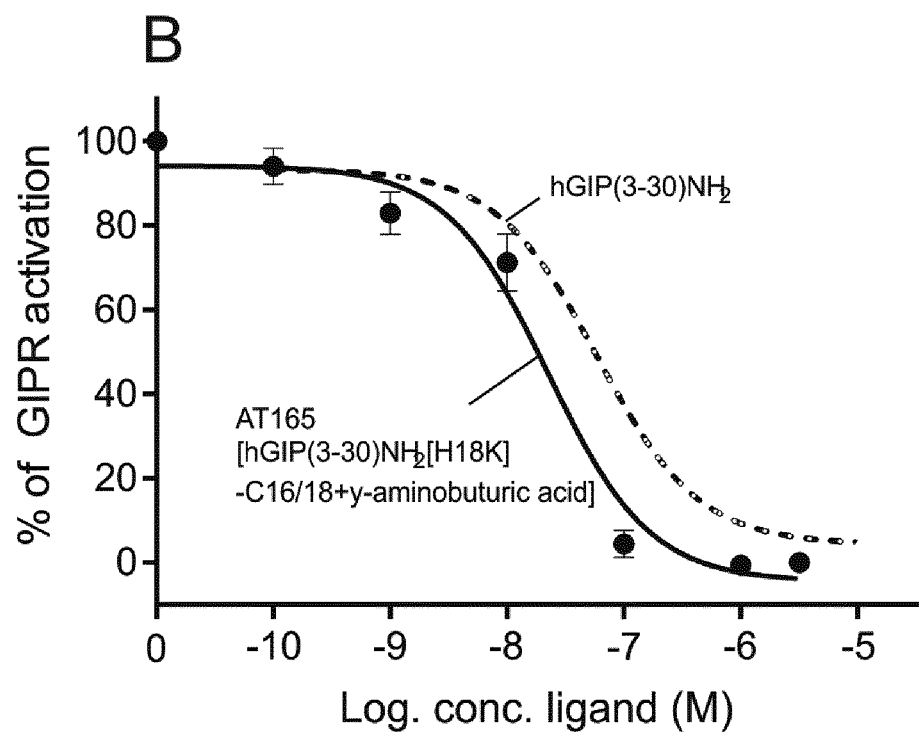
Figure 3:
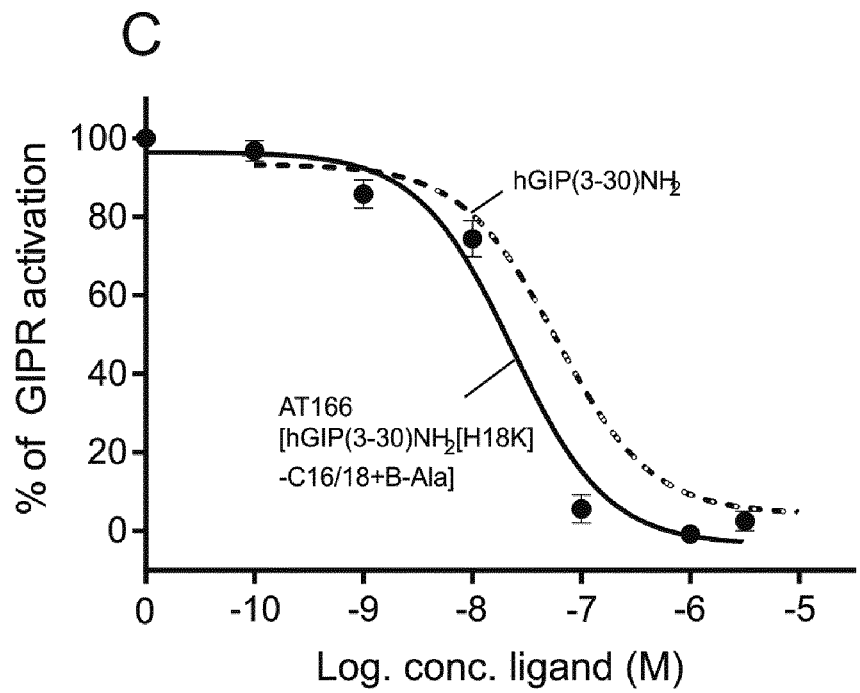
Figure 3:
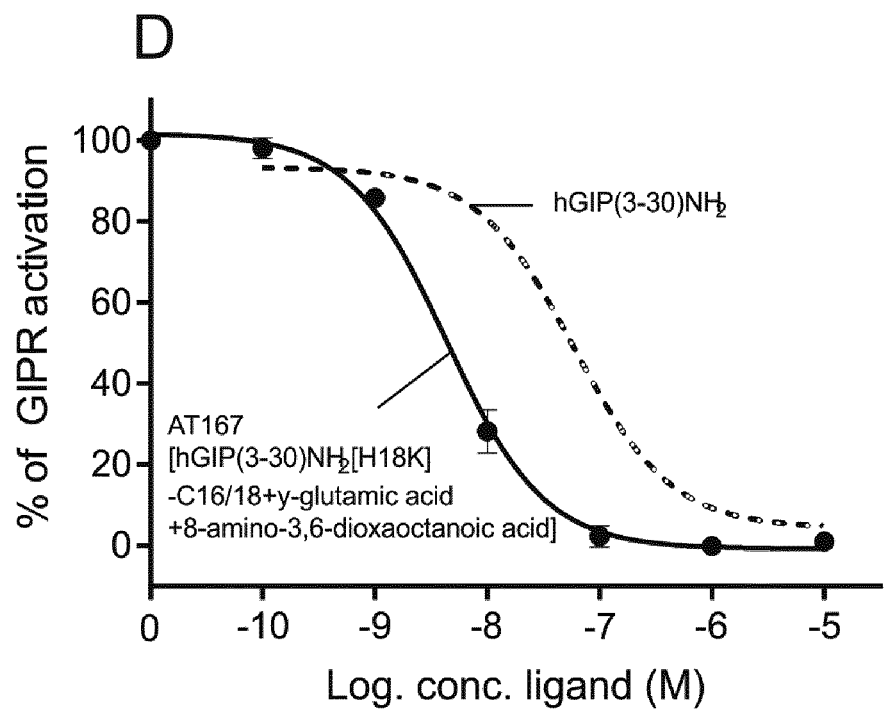

FIG. 3. Addition of linkers (molecules linking the fatty acids to the peptides) improves the antagonistic profile.

cAMP accumulation in transiently transfected COS-7 cells expressing the human GIP receptor was assessed following incubation with the different lipidated analogues with linkers. Antagonist dose-response curves were performed by inhibiting a constant amount of native GIP(1-42) corresponding to 50-80% of max receptor activation with increasing concentrations of the lipidated analogues. Curves are shown as mean±SEM, n=2.

Figure 4:
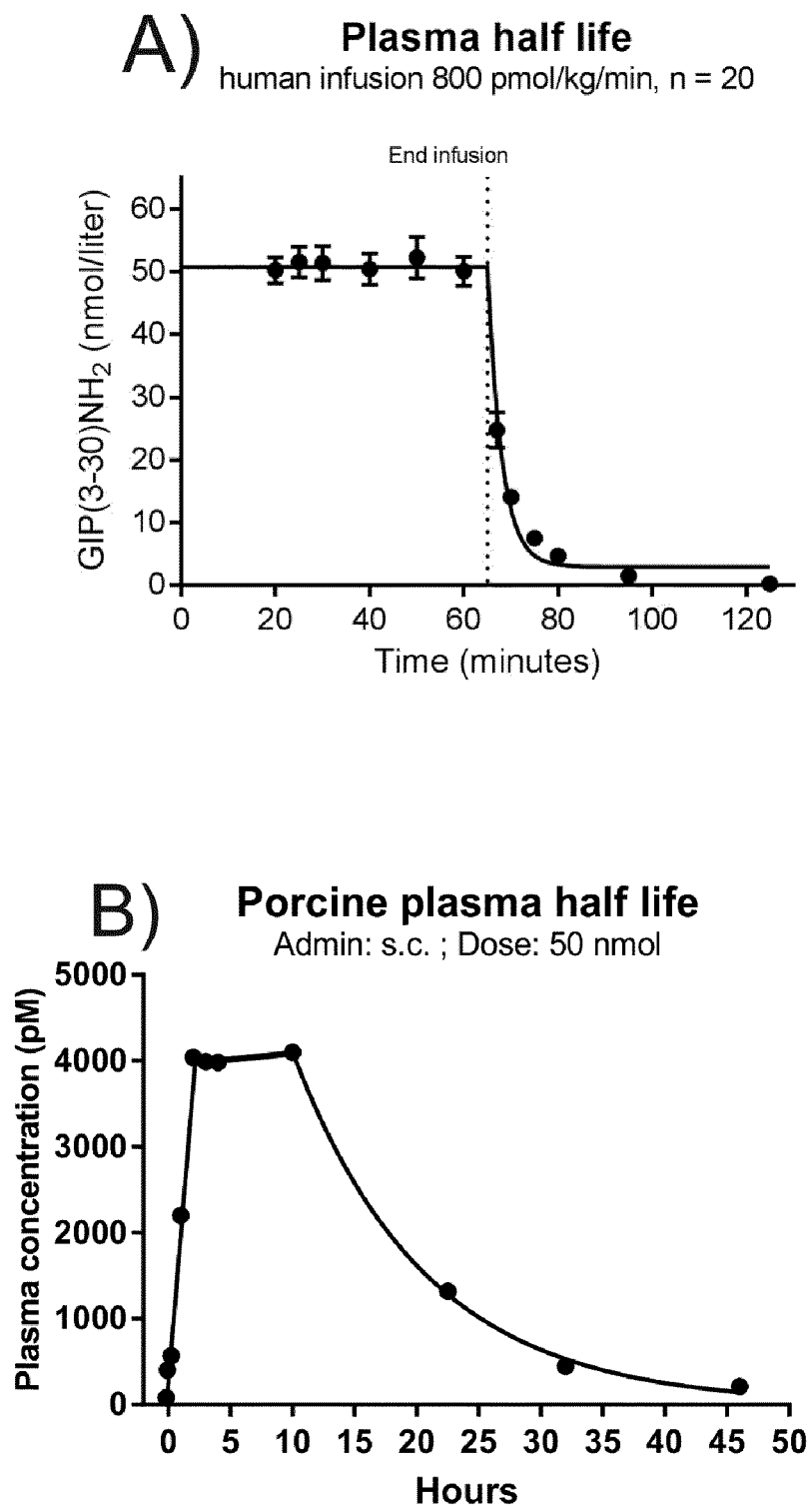

FIG. 4. Lipidation increases the elimination half-life ($T_{1/2}$) of GIP analogues. Subcutaneously administration in a pig of the lipidated GIP(3-30)$NH_2$ analogue AT117 and non-lipidated GIP(3-30)$NH_2$. Blood samples were subsequently collected at the indicated time points from a central venous catheter. The amounts of GIP(3-30)$NH_2$ and AT117 were measured using an in-house radioimmunoassay.

DEFINITIONS

The term "affinity" refers to the strength of binding between a receptor and its ligand(s). In the present context, affinity of a peptide antagonist for its binding site (Ki) will determine the duration of inhibition of agonist activity. The affinity of an antagonist can be determined experimentally using Schild regression on functional studies or by radioligand binding studies like 1) competitive binding experiments using the Cheng-Prusoff equation, 2) saturation binding experiments using the Scatchard equation or 3) kinetic studies with determination of on- and off rates ($K_{on}$ and $K_{off}$, respectively).

The term "IC50" represents the half maximal inhibitory concentration (IC50), which is a measure of the effectiveness of a substance in inhibiting a specific biological or biochemical function. This quantitative measure indicates how much of a particular drug or other substance (e.g. antagonist) is needed to inhibit a given biological process (or component of a process, i.e. an enzyme, cell, cell receptor or microorganism) by half. It is commonly used as a measure of antagonist drug potency in pharmacological research. IC50 represents the concentration of a drug that is required for 50% inhibition in vitro. In the present context, the IC50 value can also refer to the concentration of a drug at which 50% of a radio labelled ligand is displaced from the receptor, which is a characterization of drug affinity done in competition binding experiments.

The term "agonist" in the present context refers to a peptide capable of binding to and activating a receptor.

The term "antagonist" in the present context refers to a GIP peptide analogue as defined herein, capable of binding to and blocking or reducing agonist-mediated responses of a receptor. Antagonists usually do not provoke a biological response themselves upon binding to a receptor. Antagonists have affinity but no efficacy for their cognate receptors, and binding will disrupt the interaction and inhibit the function of an agonist or inverse agonist at receptors. Antagonists mediate their effects by binding to the active (orthosteric) site or to allosteric sites on receptors, or they may interact at unique binding sites not normally involved in the biological regulation of the receptors activity. Antagonist activity may be reversible or irreversible depending on the longevity of the antagonist-receptor complex, which, in turn, depends on the nature of antagonist-receptor binding. The majority of drug antagonists typically achieve their potency by competing with endogenous ligands or substrates at structurally defined binding sites on receptors. Antagonists may be competitive, non-competitive, uncompetitive, silent antagonists, partial agonists or inverse agonists.

A competitive antagonist (also known as surmountable antagonist) reversibly binds to receptors at the same binding site (i.e. at the active site) as the endogenous ligand or agonist, but without activating the receptor. Agonists and antagonists thus "compete" for the same binding site on the receptor. Once bound, an antagonist blocks agonist binding. The level of activity of the receptor is determined by the relative affinity of each molecule for the site and their relative concentrations. High concentrations of a competitive antagonist will increase the proportion of receptors that the antagonist occupies; higher concentrations of the agonist will be required to obtain the same degree of binding site occupancy.

The term "non-competitive antagonism" (also called non-surmountable or insurmountable antagonism) describes two distinct phenomena with functionally similar results: one in which the antagonist binds to the active site of the receptor, and one in which the antagonist binds to an allosteric site of the receptor. Unlike competitive antagonists, which affect the amount of agonist necessary to achieve a maximal response but do not affect the magnitude of that maximal response, non-competitive antagonists reduce the magnitude of the maximum response that can be attained by any amount of agonist.

The term "silent antagonist" refers to a competitive receptor antagonist that has absolutely no intrinsic activity for activating a receptor.

The term "partial agonist" refers to an agonist that, at a given receptor, might differ in the amplitude of the functional response that it elicits after maximal receptor occupancy. Partial agonists can act as a competitive antagonist in the presence of a full agonist (or a more efficacious agonist), as it competes with the full agonist for receptor occupancy, thereby producing a net decrease in the receptor activation as compared to that observed with the full agonist alone.

The term "inverse agonist" refers to agonists having effects similar to those of antagonists, but causing a distinct set of downstream biological responses. Constitutively active receptors that exhibit intrinsic or basal activity can have inverse agonists, which not only block the effects of binding agonists like a classical antagonist but also inhibit the basal activity of the receptor.

The term "Individual" refers to vertebrates, particular members of the mammalian species, preferably primates including humans. As used herein, 'subject' and 'individual' may be used interchangeably.

An "isolated peptide" is a peptide separated and/or recovered from a component of their natural, typically cellular, environment, that is essentially free from contaminating cellular components, such as carbohydrate, lipid, or other proteinaceous impurities associated with the polypeptide in nature. Typically, a preparation of isolated peptide contains the peptide in a highly purified form, i.e., at least about 80% pure, at least about 90% pure, at least about 95% pure, greater than 95% pure, or greater than 99% pure. The term "isolated" does not exclude the presence of the same peptide in alternative physical forms, such as dimers, tetramers or alternatively glycosylated or derived forms.

An "amino acid residue" can be a natural or non-natural amino acid residue linked by peptide bonds or bonds different from peptide bonds. The amino acid residues can be in D-configuration or L-configuration. An amino acid residue comprises an amino terminal part ($NH_2$) and a carboxy terminal part (COOH) separated by a central part comprising a carbon atom, or a chain of carbon atoms, at least one of which comprises at least one side chain or functional group. $NH_2$ refers to the amino group present at the amino terminal end of an amino acid or peptide, and COOH refers to the carboxy group present at the carboxy terminal end of an amino acid or peptide. The generic term amino acid comprises both natural and non-natural amino acids. Natural amino acids of standard nomenclature as listed in J. Biol. Chem., 243:3552-59 (1969) and adopted in 37 C.F.R., section 1.822(b)(2) belong to the group of amino acids listed herewith: Y, G, F, M, A, S, I, L, T, V, P, K, H, Q, E, W, R, D, N and C. Non-natural amino acids are those not listed immediately above. Also, non-natural amino acid residues include, but are not limited to, modified amino acid residues, L-amino acid residues, and stereoisomers of D-amino acid residues.

An "equivalent amino acid residue" refers to an amino acid residue capable of replacing another amino acid residue in a polypeptide without substantially altering the structure and/or functionality of the polypeptide. Equivalent amino acids thus have similar properties such as bulkiness of the side-chain, side chain polarity (polar or non-polar), hydrophobicity (hydrophobic or hydrophilic), pH (acidic, neutral or basic) and side chain organization of carbon molecules (aromatic/aliphatic). As such, "equivalent amino acid residues" can be regarded as "conservative amino acid substitutions".

Within the meaning of the term "equivalent amino acid substitution" as applied herein, one amino acid may be substituted for another, in one embodiment, within the groups of amino acids indicated herein below:
  i) Amino acids having polar side chains (Asp, Glu, Lys, Arg, His, Asn, Gln, Ser, Thr, Tyr, and Cys)
  ii) Amino acids having non-polar side chains (Gly, Ala, Val, Leu, Ile, Phe, Trp, Pro, and Met)
  iii) Amino acids having aliphatic side chains (Gly, Ala Val, Leu, Ile)
  iv) Amino acids having cyclic side chains (Phe, Tyr, Trp, His, Pro)
  v) Amino acids having aromatic side chains (Phe, Tyr, Trp)
  vi) Amino acids having acidic side chains (Asp, Glu)
  vii) Amino acids having basic side chains (Lys, Arg, His)
  viii) Amino acids having amide side chains (Asn, Gln)
  ix) Amino acids having hydroxy side chains (Ser, Thr)
  x) Amino acids having sulphur-containing side chains (Cys, Met),
  xi) Neutral, weakly hydrophobic amino acids (Pro, Ala, Gly, Ser, Thr)
  xii) Hydrophilic, acidic amino acids (Gln, Asn, Glu, Asp), and
  xiii) Hydrophobic amino acids (Leu, Ile, Val)

Where the L or D form (optical isomers) has not been specified it is to be understood that the amino acid in question has the natural L form, cf. Pure & Appl. Chem. Vol. (56(5) pp 595-624 (1984) or the D form, so that the peptides formed may be constituted of amino acids of L form, D form, or a sequence of mixed L forms and D forms.

A "functional variant" of a peptide is a peptide capable of performing essentially the same functions as the peptide it is a functional variant of. In particular, a functional variant can essentially bind the same molecules as the peptide it is a functional variant of.

A "bioactive agent" (i.e. a biologically active substance/ agent) is any agent, drug, compound, composition of matter or mixture which provides some pharmacologic, often beneficial, effect that can be demonstrated in vivo or in vitro. It refers to the GIP peptide analogues as defined herein and compounds or compositions comprising these. As used herein, this term further includes any physiologically or pharmacologically active substance that produces a localized or systemic effect in an individual.

The terms "drug" and "medicament" as used herein include biologically, physiologically, or pharmacologically active substances that act locally or systemically in the human or animal body.

The terms "treatment" and "treating" as used herein refer to the management and care of a patient for the purpose of combating a condition, disease or disorder. The term is intended to include the full spectrum of treatments for a given condition from which the patient is suffering, and refer equally to curative therapy, prophylactic or preventative therapy and ameliorating or palliative therapy, such as administration of the peptide or composition for the purpose of: alleviating or relieving symptoms or complications; delaying the progression of the condition, partially arresting the clinical manifestations, disease or disorder; curing or eliminating the condition, disease or disorder; amelioration or palliation of the condition or symptoms, and remission (whether partial or total), whether detectable or undetectable; and/or preventing or reducing the risk of acquiring the condition, disease or disorder, wherein "preventing" or "prevention" is to be understood to refer to the management and care of a patient for the purpose of hindering the development of the condition, disease or disorder, and includes the administration of the active compounds to prevent or reduce the risk of the onset of symptoms or complications. The term "palliation", and variations thereof, as used herein, means that the extent and/or undesirable manifestations of a physiological condition or symptom are lessened and/or time course of the progression is slowed or lengthened, as compared to not administering compositions of the present invention.

The individual to be treated is preferably a mammal, in particular a human being. Treatment of animals, such as mice, rats, dogs, cats, cows, horses, sheep and pigs, is, however, also encompassed herewith.

An "individual in need thereof" refers to an individual who may benefit from the present disclosure. In one embodiment, said individual in need thereof is a diseased individual, wherein said disease may be a metabolic disease or disorder such as obesity or diabetes, a bone density disorder or a cancer.

A treatment according to the invention can be prophylactic, ameliorating and/or curative.

"Pharmacologically effective amount", "pharmaceutically effective amount" or "physiologically effective amount" of a bioactive agent is the amount of a bioactive agent present in a pharmaceutical composition as described herein that is needed to provide a desired level of active agent in the bloodstream or at the site of action in an individual (e.g. the lungs, the gastric system, the colorectal system, prostate, etc.) to be treated to give an anticipated physiological response when such composition is administered. A bioactive agent in the present context refers to a GIP peptide analogue as disclosed herein.

"Co-administering" or "co-administration" as used herein refers to the administration of one or more GIP peptide analogues of the present invention and a state-of-the-art pharmaceutical composition. The at least two components can be administered separately, sequentially or simultaneously.

DETAILED DESCRIPTION

GIP refers to glucose-dependent insulinotropic polypeptide, also known as Gastric Inhibitory Peptide (or polypeptide). As used herein the abbreviation GIP or hGIP is human GIP (Uniprot accession number P09681). GIP is derived from a 153-amino acid proprotein and circulates as a biologically active 42-amino acid peptide. It is synthesized by K cells of the mucosa of the duodenum and the jejunum of the gastrointestinal tract.

GIPR (or GIP receptor) refers to gastric inhibitory polypeptide receptors. These seven-transmembrane proteins are found at least on beta-cells in the pancreas. As used herein the abbreviation GIPR or hGIPR is human GIPR (Uniprot accession number P48546).

The present inventors have identified GIP peptides which are antagonists of the GIPR, and which are acylated herewith to increase half-life and in vivo stability while retaining the surprising antagonistic properties. This makes them potentially useful in a range of therapeutic applications.

GIP Peptides

The present invention is directed to GIP peptide analogues which comprises a peptide fragment of GIP (native or variants) having GIPR antagonistic properties, and one or more fatty acids attached thereto to increase the half-life of said peptide while retaining the GIPR antagonistic properties.

It is an aspect to provide a glucose-dependent insulinotropic peptide (GIP) analogue of formula 1 (hGIP5-30, SEQ ID NO:1):

```
 1    2    3    4    5    6    7    8    9   10   11   12   13
 T -  F -  I -  S -  D -  Y -  S -  I -  A -  M -  D -  K -  I
14   15   16   17   18   19   20   21   22   23   24   25   26
 H -  Q -  Q -  D -  F -  V -  N -  W -  L -  L -  A -  Q -  K
``` wherein said peptide optionally further comprises the dipeptide E-G at the N-terminus (hGIP3-30, SEQ ID NO:2), or a functional variant having at least 75% sequence identity to any one of SEQ ID NO:1 and SEQ ID NO:2, wherein said peptide is modified by attaching at least one fatty acid molecule at one or more amino acid residues of any one of SEQ ID NO:1 and SEQ ID NO:2, or a functional variant having at least 75% sequence identity to any one of SEQ ID NO:1 and SEQ ID NO:2,
with the proviso that said at least one fatty acid molecule is not attached to the amino acid residue at position 26 of SEQ ID NO:1 or position 28 of SEQ ID NO:2, or a functional variant having at least 75% sequence identity to any one of SEQ ID NO:1 and SEQ ID NO:2.

It is also an aspect to provide a glucose-dependent insulinotropic peptide (GIP) analogue selected from the group consisting of formula 1 (hGIP5-30, SEQ ID NO:1):

```
 1   2   3   4   5   6   7   8   9  10  11  12
 T - F - I - S - D - Y - S - I - A - M - D - K -
13  14  15  16  17  18  19  20  21  22  23  24
 I - H - Q - Q - D - F - V - N - W - L - L - A -
25  26
 Q - K
``` and formula 2 (hGIP3-30, SEQ ID NO:2):
    1 2 3 4 5 6 7 8 9 10 11 12 13 14
    E-G-T-F-I-S-D-Y-S-I-A-M-D-K-
    15 16 17 18 19 20 21 22 23 24 25 26 27 28
    I-H-Q-Q-D-F-V-N-W-L-L-A-Q-K or a functional variant having at least 75% sequence identity to any one of SEQ ID NO:1 and SEQ ID NO:2, wherein said peptide is modified by attaching at least one fatty acid molecule at one or more amino acid residues of any one of SEQ ID NO:1 and SEQ ID NO:2, or a functional variant having at least 75% sequence identity to any one of SEQ ID NO:1 and SEQ ID NO:2,
with the proviso that said at least one fatty acid molecule is not attached to the amino acid residue at position 26 of SEQ ID NO:1 or at position 28 of SEQ ID NO:2, or a functional variant having at least 75% sequence identity to any one of SEQ ID NO:1 and SEQ ID NO:2.

In one embodiment said peptide, or GIP peptide analogue, is C-terminally amidated (—NH$_2$).

In one embodiment said at least one fatty acid molecule is not attached to the Lys (K) residue at position 26 of SEQ ID NO:1 or position 28 of SEQ ID NO:2.

In one embodiment said at least one fatty acid molecule is not attached to the amino acid residue at position 26 of SEQ ID NO:1 or position 28 of SEQ ID NO:2, wherein said amino acid residue at position26 of SEQ ID NO:1 or position 28 of SEQ ID NO:2 has been substituted with an amino acid selected from the group consisting R, A and E.

In one embodiment there is provided a glucose-dependent insulinotropic peptide (GIP) analogue comprising
    a peptide selected from the group consisting of TFISDYSIAMDKIHQQDFVNWLLAQK (hGIP5-30, SEQ ID NO:1) and EGTFISDYSIAMDKIHQQDFVNWLLAQK (hGIP3-30, SEQ ID NO:2), or a functional variant having at least 75% sequence identity to any one of SEQ ID NO:1 and SEQ ID NO:2,
    optionally amidated (—NH$_2$) at the C-terminus, and
    at least one fatty acid molecule attached to one or more amino acid residues of any one of SEQ ID NO:1 and SEQ ID NO:2, or a functional variant having at least 75% sequence identity to any one of SEQ ID NO:1 and SEQ ID NO:2, with the proviso that said at least one fatty acid molecule is not attached to the amino acid residue at position 26 of SEQ ID NO:1 or position 28 of SEQ ID NO:2, or a functional variant having at least 75% sequence identity to any one of SEQ ID NO:1 and SEQ ID NO:2.

In one embodiment there is provided a glucose-dependent insulinotropic peptide (GIP) analogue comprising
- a peptide consisting of TFISDYSIAMD-KIHQQDFVNWLLAQK (hGIP5-30, SEQ ID NO:1) or consisting of EGTFISDYSIAMD-KIHQQDFVNWLLAQK (hGIP3-30, SEQ ID NO:2), or a functional variant having at least 75% sequence identity to any one of SEQ ID NO:1 and SEQ ID NO:2, and
- at least one fatty acid molecule attached to one or more amino acid residues of any one of SEQ ID NO:1 and SEQ ID NO:2, or a functional variant having at least 75% sequence identity to any one of SEQ ID NO:1 and SEQ ID NO:2, with the proviso that said at least one fatty acid molecule is not attached to the amino acid residue at position 26 of SEQ ID NO:1 or position 28 of SEQ ID NO:2, or a functional variant having at least 75% sequence identity to any one of SEQ ID NO:1 and SEQ ID NO:2.

It is also an aspect to provide a glucose-dependent insulinotropic peptide (GIP) analogue of formula 1 (hGIP6-30, SEQ ID NO:147):

```
 6   7   8   9  10  11  12  13  14  15  16  17
 F - I - S - D - Y - S - I - A - M - D - K - I -

18  19  20  21  22  23  24  25  26  27  28  29  30
 H - Q - Q - D - F - V - N - W - L - L - A - Q - K
``` wherein said peptide optionally further comprises
- the peptide T at the N-terminus (hGIP5-30, SEQ ID NO:1),
- the dipeptide G-T at the N-terminus (hGIP4-30, SEQ ID NO:148),
- the tripeptide E-G-T at the N-terminus (hGIP3-30, SEQ ID NO:2), or a functional variant having at least 75% sequence identity to any one of SEQ ID NO:1, SEQ ID NO:2, SEQ ID NO:147 or SEQ ID NO:148,
wherein said peptide is modified by attaching at least one fatty acid molecule at one or more amino acid residues of any one of SEQ ID NO:1, SEQ ID NO:2, SEQ ID NO:147 or SEQ ID NO:148, or a functional variant having at least 75% sequence identity to any one of SEQ ID NO:1, SEQ ID NO:2, SEQ ID NO:147 or SEQ ID NO:148,
with the proviso that said at least one fatty acid molecule is not attached to the amino acid residue at position 26 of SEQ ID NO:1, position 28 of SEQ ID NO:2, position 25 of SEQ ID NO:147, or position 27 of SEQ ID NO:148, or a functional variant having at least 75% sequence identity to any one of SEQ ID NO:1, SEQ ID NO:2, SEQ ID NO:147 or SEQ ID NO:148.

Thus in one embodiment there is disclosed a glucose-dependent insulinotropic peptide (GIP) analogue selected from the group consisting of:

```
                          (hGIP5-30, SEQ ID NO: 1)
TFISDYSIAMDKIHQQDFVNWLLAQK, (hGIP3-30, SEQ ID NO: 2)
EGTFISDYSIAMDKIHQQDFVNWLLAQK, (hGIP6-30, SEQ ID NO: 147)
FISDYSIAMDKIHQQDFVNWLLAQK,
and (hGIP4-30, SEQ ID NO: 148)
GTFISDYSIAMDKIHQQDFVNWLLAQK,
``` or a functional variant having at least 75% sequence identity to any one of SEQ ID NO:1, SEQ ID NO:2, SEQ ID NO:147 or SEQ ID NO:148,
wherein said peptide is modified by attaching at least one fatty acid molecule at one or more amino acid residues of any one of SEQ ID NO:1, SEQ ID NO:2, SEQ ID NO:147 or SEQ ID NO:148, or a functional variant having at least 75% sequence identity to any one of SEQ ID NO:1, SEQ ID NO:2, SEQ ID NO:147 or SEQ ID NO:148,
with the proviso that said at least one fatty acid molecule is not attached to the amino acid residue at position 26 of SEQ ID NO:1, position 28 of SEQ ID NO:2, position 25 of SEQ ID NO:147, or position 27 of SEQ ID NO:148, or a functional variant having at least 75% sequence identity to any one of SEQ ID NO:1, SEQ ID NO:2, SEQ ID NO:147 or SEQ ID NO:148.

Functional Variant—Functionality

A glucose-dependent insulinotropic peptide (GIP) analogue as defined throughout comprises a peptide sequence (SEQ ID NO:1 or SEQ ID NO:2, and variants thereof) and at least one fatty acid molecule.

The terms 'peptide' and 'isolated peptide' may be used interchangeably herein. The terms 'variant' and 'functional variant' may be used interchangeably herein. A peptide as defined herein includes native peptide sequences and also functional variants of the defined amino acid sequences of said peptide.

In one embodiment there is provided a glucose-dependent insulinotropic peptide (GIP) analogue TFISDYSIAMD-KIHQQDFVNWLLAQK (hGIP5-30, SEQ ID NO:1), wherein said peptide optionally further comprises the dipeptide EG at the N-terminus (hGIP3-30, SEQ ID NO:2), or a functional variant having at least 75% sequence identity to any one of SEQ ID NO:1 and SEQ ID NO:2,
wherein said peptide is modified by attaching at least one fatty acid molecule at one or more amino acid residues of any one of SEQ ID NO:1 and SEQ ID NO:2, or a functional variant having at least 75% sequence identity to any one of SEQ ID NO:1 and SEQ ID NO:2,
with the proviso that said at least one fatty acid molecule is not attached to the amino acid residue at position 26 of SEQ ID NO:1 or position 28 of SEQ ID NO:2, or a functional variant having at least 75% sequence identity to any one of SEQ ID NO:1 and SEQ ID NO:2, and
wherein said peptide is capable of binding to and/or antagonising a GIPR.

In one embodiment, the GIP peptide analogues are capable of binding to a GIPR. In one embodiment, the GIP peptide analogues are capable of antagonising a GIPR. In one embodiment, the GIP peptide analogues are capable of binding to and antagonising a GIPR. In some embodiments, the GIPR is the human GIPR (Uniprot accession number P48546), the mouse GIPR (Uniprot accession number Q0P543), the rat GIPR (Uniprot accession number P43219), the dog GIPR (Uniprot accession number E2RIK5), the pig GIPR (Uniprot accession number 13LND8), and/or the *Macaca mulatta* GIPR (Uniprot accession number A0A1D5QDM0) (primate).

In one embodiment the GIP peptide analogue disclosed herein are antagonists of the hGIP receptor.

In one embodiment the GIP peptide analogue disclosed herein are competitive antagonists of the hGIP receptor.

When reference is made to a 'peptide' or 'GIP peptide analogue' herewith, this term will encompass both references to a peptide analogue per se, and also to a peptide analogue for use in therapeutic methods as defined herein.

A functional variant of the peptides of the present GIP peptide analogues are the functional equivalents of said peptide sequences, i.e. they retain at least some effect associated with the native peptide sequence.

In one embodiment a functional variant of a peptide selected from SEQ ID NO:1 or SEQ ID NO:2 (or SEQ ID NO:147 or SEQ ID NO:148) retains the same biological activities or capabilities as the native peptide or the peptide from which it is derived. In one embodiment a peptide and a functional variant thereof as defined herein is capable of one or more of: Binding to one or more GIPR; antagonizing one or more GIPR; displacing GIP1-42 and/or GIP1-30 from one or more GIPR; having a higher, equal or lower affinity for a given GIPR than GIP1-42 and/or GIP1-30; antagonizing somatostatin secretion induced by native GIP, GIP1-42 and/or GIP1-30; antagonizing insulin secretion induced by native GIP, GIP1-42 and/or GIP1-30; and antagonising glucagon secretion induced by native GIP, GIP1-42 and/or GIP1-30.

In one embodiment a peptide and a functional variant thereof is capable of binding (or binds) to one or more of the hGIPR (Uniprot accession number P48546), the rGIPR (Uniprot accession number P43219), the mGIPR (Uniprot accession number Q0P543), the dog GIPR (Uniprot accession number E2RIK5), the pig GIPR (Uniprot accession number 13LND8), and the *Macaca mulatta* GIPR (Uniprot accession number A0A1D5QDM0) (primate).

In one embodiment a peptide and a functional variant thereof is capable of inhibiting (reducing, antagonizing) one or more of i) GIP-induced glucagon secretion, ii) GIP-induced insulin secretion, iii) GIP-induced somatostatin secretion, iv) GIP-induced glucose uptake, v) GIP-induced fatty acid synthesis and/or fatty acid incorporation, vi) high or increased expression or activity of a GIPR and vii) release of GIP following a meal (post-prandial GIP release).

Functional Variant—Mutants

In one embodiment a functional variant of SEQ ID NO:1 and SEQ ID NO:2 as defined herein has at least 75% sequence identity to any one of SEQ ID NO:1 and SEQ ID NO:2. 'Identity' and 'sequence identity' may be used interchangeably herein.

In another embodiment said functional variant has at least 80% sequence identity to any one of SEQ ID NO:1 and SEQ ID NO:2.

In yet another embodiment said functional variant has at least 85% sequence identity to any one of SEQ ID NO:1 and SEQ ID NO:2.

In one embodiment said functional variant has at least 90% sequence identity to any one of SEQ ID NO:1 and SEQ ID NO:2.

In another embodiment said functional variant has at least 95% sequence identity to any one of SEQ ID NO:1 and SEQ ID NO:2.

In another embodiment said functional variant has at least 80% sequence identity, at least 85% sequence identity, at least 90% sequence identity, or at least 95% sequence identity to any one of SEQ ID NO:147 and SEQ ID NO:148.

In one embodiment said functional variant has 75% to 80% sequence identity to any one of SEQ ID NO:1 and SEQ ID NO:2, such as 80% to 85%, such as 85% to 90%, such as 90% to 95% sequence identity to any one of SEQ ID NO:1 and SEQ ID NO:2.

In one embodiment there is provided a glucose-dependent insulinotropic peptide (GIP) analogue TFISDYSIAMD-KIHQQDFVNWLLAQK (hGIP5-30, SEQ ID NO:1), wherein said peptide optionally further comprises the dipeptide EG at the N-terminus (hGIP3-30, SEQ ID NO:2), or a functional variant of any one of SEQ ID NO:1 and SEQ ID NO:2 having 1 to 6 individual amino acid substitutions, wherein said peptide is modified by attaching at least one fatty acid molecule at one or more amino acid residues of any one of SEQ ID NO:1 and SEQ ID NO:2, or a functional variant having at least 75% sequence identity to any one of SEQ ID NO:1 and SEQ ID NO:2, with the proviso that said at least one fatty acid molecule is not attached to the amino acid residue at position 26 of SEQ ID NO:1 or position 28 of SEQ ID NO:2, or a functional variant having at least 75% sequence identity to any one of SEQ ID NO:1 and SEQ ID NO:2.

1 individual amino acid substitution as used herein is understood as an amino acid substitution at any one specific position of any one of SEQ ID NO:1 and SEQ ID NO:2, which is substituted independently of any other features of any one of SEQ ID NO:1 and SEQ ID NO:2, e.g. other amino acid substitutions or fatty acid modifications.

In one embodiment said functional variant of any one of SEQ ID NO:1 and SEQ ID NO:2 has 1 to 6 individual amino acid substitutions, such as 1 to 2, 2 to 3, 3 to 4, 4 to 5 or 5 to 6 individual amino acid substitutions as compared to the corresponding part or position of any one of SEQ ID NO:1 and SEQ ID NO:2 (or, between the variant and the corresponding native GIP peptide).

In one embodiment said functional variant of any one of SEQ ID NO:147 and SEQ ID NO:148 has 1 to 6 individual amino acid substitutions, such as 1 to 2, 2 to 3, 3 to 4, 4 to 5 or 5 to 6 individual amino acid substitutions as compared to the corresponding part or position of any one of SEQ ID NO:147 and SEQ ID NO:148 (or, between the variant and the corresponding native GIP peptide).

In one embodiment said functional variant of any one of SEQ ID NO:1 and SEQ ID NO:2 has 1 individual amino acid substitution. In one embodiment said functional variant of any one of SEQ ID NO:1 and SEQ ID NO:2 has no more than 1 individual amino acid substitution.

In one embodiment said functional variant of any one of SEQ ID NO:1 and SEQ ID NO:2 has 2 individual amino acid substitutions. In one embodiment said functional variant of any one of SEQ ID NO:1 and SEQ ID NO:2 has no more than 2 individual amino acid substitutions.

In one embodiment said functional variant of any one of SEQ ID NO:1 and SEQ ID NO:2 has 3 individual amino acid substitutions. In one embodiment said functional variant of any one of SEQ ID NO:1 and SEQ ID NO:2 has no more than 3 individual amino acid substitutions.

In one embodiment said functional variant of any one of SEQ ID NO:1 and SEQ ID NO:2 has 4 individual amino acid substitutions. In one embodiment said functional variant of any one of SEQ ID NO:1 and SEQ ID NO:2 has no more than 4 individual amino acid substitutions.

In one embodiment said functional variant of any one of SEQ ID NO:1 and SEQ ID NO:2 has 5 individual amino acid substitutions. In one embodiment said functional variant of any one of SEQ ID NO:1 and SEQ ID NO:2 has no more than 5 individual amino acid substitutions.

In one embodiment said functional variant of any one of SEQ ID NO:1 and SEQ ID NO:2 has 6 individual amino acid substitutions. In one embodiment said functional variant of any one of SEQ ID NO:1 and SEQ ID NO:2 has no more than 6 individual amino acid substitutions.

In one embodiment, one or more, or all, of said amino acid substitutions are conservative amino acid substitutions (or synonymous substitutions). A conservative substitution is the substitution of amino acids whose side chains have similar biochemical properties and thus do not affect the function of the peptide.

Among the common amino acids, for example, a "conservative amino acid substitution" can also be illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

In one embodiment, a serine residue of a peptide of the invention is substituted with an amino acid selected from the group consisting of Gln, Asn and Thr (all amino acids with polar uncharged side chains); and independently thereof, a glycine residue (Gly) is substituted with an amino acid selected from the group consisting of Ala, Val, Leu, and Ile; and independently thereof, an arginine residue (Arg) is substituted with an amino acid selected from the group consisting of Lys and His (all have positively charged side chains); and independently thereof, a lysine residue (Lys) is substituted with an amino acid selected from the group consisting of Arg and His; and independently thereof, a methionine residue (Met) is substituted with an amino acid selected from the group consisting of Leu, Pro, Ile, Val, Phe, Tyr and Trp (all have hydrophobic side chains); and independently thereof, a glutamine residue (Gin) is substituted with an amino acid selected from the group consisting of Asp, Glu, and Asn; and independently thereof, an alanine residue (Ala) is substituted with an amino acid selected from the group consisting of Gly, Val, Leu, and Ile.

Particular amino acid substitutions as disclosed herein are K to R, E to D, L to M, Q to E, I to V, I to L, A to S, Y to W, K to Q, S to T, N to S, M to L and Q to R.

The identity between amino acid sequences may be calculated using well known algorithms such as BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, or BLOSUM 90, or by simple comparison of the specific amino acids present at corresponding positions in two peptide sequences to be compared.

Homology may be used as a synonym to identity/sequence identity.

In another embodiment, a functional variant as defined herein includes sequences wherein an alkyl amino acid is substituted for an alkyl amino acid, wherein an aromatic amino acid is substituted for an aromatic amino acid, wherein a sulfur-containing amino acid is substituted for a sulfur-containing amino acid, wherein a hydroxy-containing amino acid is substituted for a hydroxy-containing amino acid, wherein an acidic amino acid is substituted for an acidic amino acid, wherein a basic amino acid is substituted for a basic amino acid, and/or wherein a dibasic monocarboxylic amino acid is substituted for a dibasic monocarboxylic amino acid.

Conservative substitutions may be introduced in any one or more positions of a peptide selected from any one of SEQ ID NO:1 and SEQ ID NO:2, as long as the resulting variant remains functional. It may however also be desirable to introduce non-conservative substitutions in one or more positions (non-synonymous substitutions).

A non-conservative substitution leading to the formation of a variant of a peptide selected from any one of SEQ ID NO:1 and SEQ ID NO:2 in one embodiment comprises substitution of amino acid residues that i) differ substantially in polarity, for example a residue with a non-polar side chain (Ala, Leu, Pro, Trp, Val, Ile, Leu, Phe or Met) substituted for a residue with a polar side chain such as Gly, Ser, Thr, Cys, Tyr, Asn, or Gln or a charged amino acid such as Asp, Glu, Arg, or Lys, or substituting a charged or a polar residue for a non-polar one; and/or ii) differ substantially in its effect on peptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Substitution of amino acids can in one embodiment be made based upon their hydrophobicity and hydrophilicity values and the relative similarity of the amino acid side-chain substituents, including charge, size, and the like.

The peptides or their functional variant counterparts as defined herein comprise proteinogenic or natural amino acids, i.e. the 22 amino acids naturally incorporated into polypeptides. Of these, 20 are encoded by the universal genetic code and the remaining 2; selenocysteine (Sec, U) and pyrrolysine (Pyl, O), are incorporated into proteins by unique synthetic mechanisms.

A peptide as defined herein in one embodiment comprises one or more non-naturally occurring amino acid residues (unnatural, non-proteinogenic or non-standard amino acids). Non-naturally occurring amino acids include e.g., without limitation, beta-2-naphthyl-alanine, trans-3-methylproline, 2,4-methanoproline, cis-4-hydroxyproline, ornithine (Orn), trans-4-hydroxyproline, N-methylglycine, allo-threonine, methylthreonine, hydroxyethylcysteine, hydroxyethylhomocysteine, nitroglutamnine, homoglutamine, pipecolic acid, thiazolidine carboxylic acid, dehydroproline, 3- and 4-methylproline, 3,3-dimethylproline, tert-leucine, norleucine (Nle), methoxinine (Mox), norvaline, 2-azaphenylalanine, 3-azaphenylalanine, 4-azaphenylalanine, and 4-fluorophenylalanine.

In one embodiment the amino acid Met is substituted with an oxidation resistant amino acid analogue, for example, norleucine (Nle) which preserves the length of the amino acid side chain important for hydrophobic interactions but not its hydrogen-bonding properties; or methoxinine (Mox), a non-canonical amino acid that resembles more closely the electronic properties of Met in comparison to Nle.

Any amino acids as defined herein may be in the L- or D-configuration. If nothing is specified, reference to the L-isomeric form is preferably meant.

The standard and/or non-standard amino acids may be linked by peptide bonds (to form a linear peptide chain), or by non-peptide bonds (e.g. via the variable side-chains of the amino acids). Preferably, the amino acids of the peptides defined herein are linked by peptide bonds.

The term peptide also embraces post-translational modifications introduced by chemical or enzyme-catalyzed reactions, as are known in the art. These include acetylation, phosphorylation, methylation, glucosylation, glycation, amidation, hydroxylation, deimination, deamidation, carbamylation and sulfation of one or more amino acid residues, and also proteolytic modification by known proteinases including lysosomal kathepsins, and also calpains, secretases and matrix-metalloproteinases.

In a preferred embodiment a peptide selected from the group consisting of SEQ ID NO:1 and SEQ ID NO:2 or a functional variant thereof is amidated, such as C-terminally amidated (—NH$_2$). In one exemplary embodiment thereof, the peptide is hGIP(5-30)-NH$_2$ or hGIP(3-30)-NH$_2$, or variants thereof, which comprises also a fatty acid molecule.

In one embodiment a peptide selected from the group consisting of SEQ ID NO:1 and SEQ ID NO:2 or a functional variant thereof is acetylated, such as N-terminally acetylated.

Also, functional equivalents of the peptides may comprise chemical modifications such as ubiquitination, labeling (e.g., with radionuclides, various enzymes, etc.), pegylation (derivatization with polyethylene glycol), or by insertion (or substitution by chemical synthesis) of amino acids such as ornithine, which do not normally occur in human proteins (non-proteinogenic).

Sterically similar compounds may be formulated to mimic the key portions of the peptide structure. This may be achieved by techniques of modelling and chemical designing known to those of skill in the art. For example, esterification and other alkylations may be employed to modify the amino terminus of e.g. a di-arginine peptide backbone, to mimic a tetra peptide structure. It will be understood that all such sterically similar constructs fall within the scope of the present invention. Peptides with N-terminal and C-terminal alkylations and esterifications are also encompassed within the present invention.

In one embodiment a functional variant of any one of SEQ ID NO:1 and SEQ ID NO:2 is a variant wherein an amino acid selected from the group consisting of N, Q and T is substituted with an amino acid selected from the group consisting of D, E and S. In one embodiment such amino acid substitutions increase the solubility of the resulting peptide.

In one embodiment a functional variant of any one of SEQ ID NO:1 and SEQ ID NO:2 is a variant wherein the K at position 26 of SEQ ID NO:1 or position 28 of SEQ ID NO:2 is substituted with any amino acid.

Any amino acid as used herein refers to both naturally occurring and non-naturally occurring amino acids as defined herein.

In one embodiment a functional variant of any one of SEQ ID NO:1 and SEQ ID NO:2 is a variant wherein the K at position 26 of SEQ ID NO:1 or position 28 of SEQ ID NO:2 is substituted with a conservative amino acid substitution.

In one embodiment a functional variant of any one of SEQ ID NO:1 and SEQ ID NO:2 is a variant wherein a hydrophobic amino acid is substituted with a hydrophilic amino acid.

In one embodiment a functional variant of any one of SEQ ID NO:1 and SEQ ID NO:2 is a variant wherein the K at position 26 of SEQ ID NO:1 or position 28 of SEQ ID NO:2 is substituted with a hydrophilic amino acid.

In one embodiment a functional variant of any one of SEQ ID NO:1 and SEQ ID NO:2 is a variant wherein the K at position 26 of SEQ ID NO:1 or position 28 of SEQ ID NO:2 is substituted with an amino acid selected from the group consisting of D, E, S, R and A, such as an amino acid selected from the group consisting of R, A and E.

In one embodiment a functional variant of any one of SEQ ID NO:1 and SEQ ID NO:2 is a variant wherein the K at position 26 of SEQ ID NO:1 or position 28 of SEQ ID NO:2 is substituted with any amino acid when the K at position 26 of SEQ ID NO:1 or position 28 of SEQ ID NO:2 is not modified by attaching a fatty acid molecule.

In one embodiment a functional variant of any one of SEQ ID NO:1 and SEQ ID NO:2 is a variant wherein the K at position 12 of SEQ ID NO:1 or position 14 of SEQ ID NO:2 is substituted with any amino acid.

In one embodiment a functional variant of any one of SEQ ID NO:1 and SEQ ID NO:2 is a variant wherein the K at position 12 of SEQ ID NO:1 or position 14 of SEQ ID NO:2 is substituted with a conservative amino acid substitution.

In one embodiment a functional variant of any one of SEQ ID NO:1 and SEQ ID NO:2 is a variant wherein the K at position 12 of SEQ ID NO:1 or position 14 of SEQ ID NO:2 is substituted with an amino acid selected from the group consisting of D, E, S, R and A, such as an amino acid selected from the group consisting of R, A and E.

In one embodiment a functional variant of any one of SEQ ID NO:1 and SEQ ID NO:2 is a variant wherein the K at position 12 of SEQ ID NO:1 or position 14 of SEQ ID NO:2 is substituted with any amino acid when the K at position 16 is not modified by attaching a fatty acid molecule.

In one embodiment a functional variant of any one of SEQ ID NO:1 and SEQ ID NO:2 is a variant wherein the K at position 2 of SEQ ID NO:1 or position 14 of SEQ ID NO:2 and the K at position 26 of SEQ ID NO:1 or position 28 of SEQ ID NO:2 are both substituted with any amino acid, such as conservative amino acid substitutions, such as substituted with an amino acid selected from the group consisting of D, E, S, R and A, such as substituted with an amino acid selected from the group consisting of R, A and E.

In one embodiment a functional variant of any one of SEQ ID NO:1 and SEQ ID NO:2 is a variant wherein the M at position 10 of SEQ ID NO:1 or position 12 of SEQ ID NO:2 is substituted with any amino acid, such as substituted with L, S, K or norleucine (Nle) or methoxinine (Mox).

In one embodiment a functional variant of any one of SEQ ID NO:1 and SEQ ID NO:2 is a variant wherein the D at position 11 of SEQ ID NO:1 or position 13 of SEQ ID NO:2 is substituted with any amino acid.

In one embodiment a functional variant of any one of SEQ ID NO:1 and SEQ ID NO:2 is a variant wherein the D at position 11 of SEQ ID NO:1 or position 13 of SEQ ID NO:2 is substituted with a conservative amino acid substitution.

In one embodiment a functional variant of any one of SEQ ID NO:1 and SEQ ID NO:2 is a variant wherein the D at position 11 of SEQ ID NO:1 or position 13 of SEQ ID NO:2 is substituted with an amino acid selected from the group consisting of E, A, Orn and K.

In one embodiment a functional variant of any one of SEQ ID NO:1 and SEQ ID NO:2 is a variant wherein the H at position 14 of SEQ ID NO:1 or position 16 of SEQ ID NO:2 is substituted with any amino acid.

In one embodiment a functional variant of any one of SEQ ID NO:1 and SEQ ID NO:2 is a variant wherein the H at position 14 of SEQ ID NO:1 or position 16 of SEQ ID NO:2 is substituted with a conservative amino acid substitution.

In one embodiment a functional variant of any one of SEQ ID NO:1 and SEQ ID NO:2 is a variant wherein the H at position 14 of SEQ ID NO:1 or position 16 of SEQ ID NO:2 is substituted with an amino acid selected from the group consisting of A, R, Orn and K.

In one embodiment a functional variant of any one of SEQ ID NO:1 and SEQ ID NO:2 is a variant wherein the S at position 7 of SEQ ID NO:1 or position 9 of SEQ ID NO:2 is substituted with an amino acid selected from the group consisting of Orn and K.

In one embodiment a functional variant of any one of SEQ ID NO:1 and SEQ ID NO:2 is a variant wherein the I at position 8 of SEQ ID NO:1 or position 10 of SEQ ID NO:2 is substituted with an amino acid selected from the group consisting of Orn and K.

In one embodiment a functional variant of any one of SEQ ID NO:1 and SEQ ID NO:2 is a variant wherein the A at position 9 of SEQ ID NO:1 or position 11 of SEQ ID NO:2 is substituted with an amino acid selected from the group consisting of Orn and K.

In one embodiment a functional variant of any one of SEQ ID NO:1 and SEQ ID NO:2 is a variant having (comprising) an amino acid substitution at one or more of positions 7 (Ser), 8 (Ile), 9 (Ala), 10 (Met), 11 (Asp), 12 (Lys), 14 (His) and 26 (Lys) of SEQ ID NO:1; or at one or more of positions 9 (Ser), 10 (Ile), 11 (Ala), 12 (Met), 13 (Asp), 14 (Lys), 16 (His) and 28 (Lys) of SEQ ID NO:2, including conservative and non-conservative amino acid substitutions.

In one embodiment a functional variant of any one of SEQ ID NO:1 and SEQ ID NO:2 is a variant wherein one or more amino acid residues are substituted with Ornithine. In one embodiment a variant as defined herein making reference to substitution with a Lys residue may equally be substituted an Orn residue. Both Lys and Orn can be modified on their side chain amino group (epsilon- or delta-amino group, respectively).

In one embodiment a functional variant of any one of SEQ ID NO:1 and SEQ ID NO:2 is a variant wherein one or more amino acid residues are substituted with Ornithine, wherein a fatty acid molecule is attached to said Ornithine residue.

In one embodiment a functional variant of any one of SEQ ID NO:1 and SEQ ID NO:2 is a variant wherein one amino acid residue is substituted with Ornithine.

In one embodiment a functional variant of SEQ ID NO:2 is a variant wherein E (Glu) at position 1 is substituted with pGlu (pyroglutamic acid).

In one embodiment the peptide is non-naturally occurring.

In one embodiment the peptide is synthetic.

In one embodiment the peptide is an isolated peptide.

GIP(5-30) Peptides

In one embodiment there is provided a GIP peptide analogue said peptide having the sequence TFISDYX$_{11}$X$_{12}$X$_{13}$X$_{14}$X$_{15}$X$_{16}$IX$_{18}$QQDFVNWLLAQX$_{30}$ (SEQ ID NO:3), wherein X$_{11}$ is selected from the group consisting of S, K and Orn,
X$_{12}$ is selected from the group consisting of I, K and Orn,
X$_{13}$ is selected from the group consisting of A, K and Orn,
X$_{14}$ is selected from the group consisting of M, K, L, S, Nle and Mox,
X$_{16}$ is selected from the group consisting of D, E, A, K and Orn,
X$_{16}$ is selected from the group consisting of K, R, A and E,
X$_{18}$ is selected from the group consisting of H, A, R, K and Orn, and
X$_{30}$ is selected from the group consisting of K, R, A and E, or a functional variant thereof having at least 75% sequence identity to said sequence, wherein said peptide is modified by attaching at least one fatty acid molecule at one or more amino acid residues of said sequence, with the proviso that said at least one fatty acid molecule is not attached to X$_{30}$.

In one embodiment the peptide of the present GIP peptide analogue is selected from the group consisting of:

```
                              (hGIP5-30, SEQ ID NO: 1)
TFISDYSIAMDKIHQQDFVNWLLAQK, (hGIP(5-30)K16R H18K K30R; SEQ ID NO: 5)
TFISDYSIAMDRIKQQDFVNWLLAQR, (hGIP(5-30)K16R K30R; SEQ ID NO: 6)
TFISDYSIAMDRIHQQDFVNWLLAQR, (hGIP(5-30)H18A; SEQ ID NO: 7)
TFISDYSIAMDKIAQQDFVNWLLAQK, (hGIP(5-30)H18K; SEQ ID NO: 8)
TFISDYSIAMDKIKQQDFVNWLLAQK, (hGIP(5-30)D15E H18A; SEQ ID NO: 9)
TFISDYSIAMEKIAQQDFVNWLLAQK, (hGIP(5-30)K16A H18A; SEQ ID NO: 10)
TFISDYSIAMDAIAQQDFVNWLLAQK, (hGIP(5-30)D15E; SEQ ID NO: 11)
TFISDYSIAMEKIHQQDFVNWLLAQK, (hGIP(5-30)D15N; SEQ ID NO: 12)
TFISDYSIAMNKIHQQDFVNWLLAQK, (hGIP(5-30)K16A; SEQ ID NO: 13)
TFISDYSIAMDAIHQQDFVNWLLAQK, (hGIP(5-30)K16H; SEQ ID NO: 14)
TFISDYSIAMDHIHQQDFVNWLLAQK, (hGIP(5-30)K16R; SEQ ID NO: 15)
TFISDYSIAMDRIHQQDFVNWLLAQK, (hGIP(5-30)H18F; SEQ ID NO: 16)
TFISDYSIAMDKIFQQDFVNWLLAQK, (hGIP(5-30)H18W; SEQ ID NO: 17)
TFISDYSIAMDKIWQQDFVNWLLAQK, (hGIP(5-30)K30R; SEQ ID NO: 18)
TFISDYSIAMDKIHQQDFVNWLLAQR, (hGIP(5-30)K30H; SEQ ID NO: 19)
TFISDYSIAMDKIHQQDFVNWLLAQH (hGIP(5-30)T5K, SEQ ID NO: 20)
KFISDYSIAMDKIHQQDFVNWLLAQK, (hGIP(5-30)F6K, SEQ ID NO: 21)
TKISDYSIAMDKIHQQDFVNWLLAQK, (hGIP(5-30)I7K, SEQ ID NO: 22)
TFKSDYSIAMDKIHQQDFVNWLLAQK, (hGIP(5-30)S8K, SEQ ID NO: 23)
TFIKDYSIAMDKIHQQDFVNWLLAQK, (hGIP(5-30)D9K, SEQ ID NO: 24)
TFISKYSIAMDKIHQQDFVNWLLAQK, (hGIP(5-30)Y10K, SEQ ID NO: 25)
TFISDKSIAMDKIHQQDFVNWLLAQK, (hGIP(5-30)S11K, SEQ ID NO: 26)
TFISDYKIAMDKIHQQDFVNWLLAQK, (hGIP(5-30)I12K, SEQ ID NO: 27)
TFISDYSKAMDKIHQQDFVNWLLAQK, (hGIP(5-30)A13K, SEQ ID NO: 28)
TFISDYSIKMDKIHQQDFVNWLLAQK, (hGIP(5-30)M14K, SEQ ID NO: 29)
TFISDYSIAKDKIHQQDFVNWLLAQK, (hGIP(5-30)D15K, SEQ ID NO: 30)
TFISDYSIAMKKIHQQDFVNWLLAQK, (hGIP(5-30)I17K, SEQ ID NO: 31)
TFISDYSIAMDKKHQQDFVNWLLAQK, (hGIP(5-30)Q19K, SEQ ID NO: 32)
TFISDYSIAMDKIHKQDFVNWLLAQK,
```

| | |
|---|---|
| (hGIP(5-30)Q20K, SEQ ID NO: 33) | TFISDYSIAMDKIHQKDFVNWLLAQK, |
| (hGIP(5-30)D21K, SEQ ID NO: 34) | TFISDYSIAMDKIHQQKFVNWLLAQK, |
| (hGIP(5-30)F22K, SEQ ID NO: 35) | TFISDYSIAMDKIHQQDKVNWLLAQK, |
| (hGIP(5-30)V23K, SEQ ID NO: 36) | TFISDYSIAMDKIHQQDFKNWLLAQK, |
| (hGIP(5-30)N24K, SEQ ID NO: 37) | TFISDYSIAMDKIHQQDFVKWLLAQK, |
| (hGIP(5-30)W25K, SEQ ID NO: 38) | TFISDYSIAMDKIHQQDFVNKLLAQK, |
| (hGIP(5-30)L26K, SEQ ID NO: 39) | TFISDYSIAMDKIHQQDFVNWKLAQK, |
| (hGIP(5-30)L27K, SEQ ID NO: 40) | TFISDYSIAMDKIHQQDFVNWLKAQK, |
| (hGIP(5-30)A28K, SEQ ID NO: 41) | TFISDYSIAMDKIHQQDFVNWLLKQK, |
| (hGIP(5-30)Q29K, SEQ ID NO: 42) | TFISDYSIAMDKIHQQDFVNWLLAKK |
| (hGIP(5-30)S11K H18A, SEQ ID NO: 43) | TFISDYKIAMDKIAQQDFVNWLLAQK, |
| (hGIP(5-30)S11K H18R, SEQ ID NO: 44) | TFISDYKIAMDKIRQQDFVNWLLAQK, |
| (hGIP(5-30)S11K D15E, SEQ ID NO: 45) | TFISDYKIAMEKIHQQDFVNWLLAQK, |
| (hGIP(5-30)S11K M14Nle, SEQ ID NO: 46) | TFISDYKIANleDKIHQQDFVNWLLAQK, |
| (hGIP(5-30)S11K M14L, SEQ ID NO: 47) | TFISDYKIALDKIHQQDFVNWLLAQK, |
| (hGIP(5-30)I12K H18A, SEQ ID NO: 48) | TFISDYSKAMDKIAQQDFVNWLLAQK, |
| (hGIP(5-30)I12K H18R, SEQ ID NO: 49) | TFISDYSKAMDKIRQQDFVNWLLAQK, |
| (hGIP(5-30)I12K D15E, SEQ ID NO: 50) | TFISDYSKAMEKIHQQDFVNWLLAQK, |
| (hGIP(5-30)I12K M14Nle, SEQ ID NO: 51) | TFISDYSKANleDKIHQQDFVNWLLAQK, |
| (hGIP(5-30)I12K M14L, SEQ ID NO: 52) | TFISDYSKALDKIHQQDFVNWLLAQK, |
| (hGIP(5-30)A13K H18A, SEQ ID NO: 53) | TFISDYSIKMDKIAQQDFVNWLLAQK, |
| (hGIP(5-30)A13K H18R, SEQ ID NO: 54) | TFISDYSIKMDKIRQQDFVNWLLAQK, |
| (hGIP(5-30)A13K D15E, SEQ ID NO: 55) | TFISDYSIKMEKIHQQDFVNWLLAQK, |
| (hGIP(5-30)A13K M14Nle, SEQ ID NO: 56) | TFISDYSIKNleDKIHQQDFVNWLLAQK, |
| (hGIP(5-30)A13K M14L, SEQ ID NO: 57) | TFISDYSIKLDKIHQQDFVNWLLAQK, |
| (hGIP(5-30)D15E H18K; SEQ ID NO: 58) | TFISDYSIAMEKIKQQDFVNWLLAQK, |
| (hGIP(5-30) M14Nle H18K; SEQ ID NO: 59) | TFISDYSIANleDKIKQQDFVNWLLAQK, |
| (hGIP(5-30) M14L H18K; SEQ ID NO: 60) | TFISDYSIALDKIKQQDFVNWLLAQK, |
| (hGIP(5-30)D15Orn, SEQ ID NO: 61) | TFISDYSIAMOrnKIHQQDFVNWLLAQK, |
| (hGIP(5-30)H18Orn; SEQ ID NO: 62) | TFISDYSIAMDKIOrnQQDFVNWLLAQK, |
| (hGIP(5-30)M14L K16R H18K K30R; SEQ ID NO: 63) | TFISDYSIALDRIKQQDFVNWLLAQR, |
| (hGIP(5-30)T5K K16R K30R, SEQ ID NO: 64) | KFISDYSIAMDRIHQQDFVNWLLAQR, |
| (hGIP(5-30)T5K M14L K16R K30R, SEQ ID NO: 65) | KFISDYSIAMDKIHQQDFVNWLLAQK, |
| (hGIP(5-30)S11K K16R K30R, SEQ ID NO: 66) | TFISDYKIAMDRIHQQDFVNWLLAQR, |
| (hGIP(5-30)S11K M14L K16R K30R, SEQ ID NO: 67) | TFISDYKIALDRIHQQDFVNWLLAQR, |
| (hGIP(5-30)I12K K16R K30R, SEQ ID NO: 68) | TFISDYSKAMDRIHQQDFVNWLLAQR, |
| (hGIP(5-30)I12K M14L K16R K30R, SEQ ID NO: 69) | TFISDYSKALDRIHQQDFVNWLLAQR, |
| (hGIP(5-30)A13K K16R K30R, SEQ ID NO: 70) | TFISDYSIKMDRIHQQDFVNWLLAQR, |
| (hGIP(5-30)A13K M14L K16R K30R, SEQ ID NO: 71) | TFISDYSIKLDRIHQQDFVNWLLAQR, and |
| (SEQ ID NO: 145) | TFISDYSIAMDRIHQQKFVNWLLAQR, | wherein said peptide is modified by attaching at least one fatty acid molecule at one or more amino acid residues, such as by attaching one fatty acid molecule at one amino acid residue, with the proviso that said at least one fatty acid molecule is not attached to the amino acid residue at position 30, such as not attached to the amino acid residue K or R at position 30

In one embodiment the fatty acid molecule is attached to a K residue within position 1-25 of SEQ ID NO:1 and variants thereof. In one embodiment the fatty acid molecule is attached to the N-terminal amino acid residue, i.e. the T residue at position 1 of SEQ ID NO:1.

In one embodiment said peptide is C-terminally amidated (—NH$_2$).

GIP(3-30) Peptides

In one embodiment there is provided a GIP peptide analogue said peptide having the sequence EGTFISDY$X_{11}X_{12}X_{13}X_{14}X_{15}X_{16}IX_{18}$QQDFVNWLLAQX$_{30}$ (SEQ ID NO:4), wherein $X_{11}$ is selected from the group consisting of S, K and Orn,
$X_{12}$ is selected from the group consisting of I, K and Orn,
$X_{13}$ is selected from the group consisting of A, K and Orn,
$X_{14}$ is selected from the group consisting of M, K, L, S, Nle and Mox,
$X_{16}$ is selected from the group consisting of D, E, A, K and Orn,
$X_{16}$ is selected from the group consisting of K, R, A and E,
$X_{18}$ is selected from the group consisting of H, A, R, K and Orn, and
$X_{30}$ is selected from the group consisting of K, R, A and E or a functional variant thereof having at least 75% sequence identity to said sequence, wherein said peptide is modified by attaching at least one fatty acid molecule at one or more amino acid residues of said sequence, with the proviso that said at least one fatty acid molecule is not attached to $X_{30}$.

In one embodiment the peptide of the present GIP peptide analogue is selected from the group consisting of:

```
                            (hGIP3-30, SEQ ID NO: 2)
EGTFISDYSIAMDKIHQQDFVNWLLAQK, (hGIP(3-30)K16R H18K K30R; SEQ ID NO: 72)
EGTFISDYSIAMDRIKQQDFVNWLLAQR, (hGIP(3-30)K16R K30R; SEQ ID NO: 73)
EGTFISDYSIAMDRIHQQDFVNWLLAQR, (hGIP(3-30)H18A; SEQ ID NO: 74)
EGTFISDYSIAMDKIAQQDFVNWLLAQK, (hGIP(3-30)H18K; SEQ ID NO: 75)
EGTFISDYSIAMDKIKQQDFVNWLLAQK, (hGIP(3-30)D15E H18A; SEQ ID NO: 76)
EGTFISDYSIAMEKIAQQDFVNWLLAQK, (hGIP(3-30)K16A H18A; SEQ ID NO: 77)
EGTFISDYSIAMDAIAQQDFVNWLLAQK, (hGIP(3-30)D15E; SEQ ID NO: 78)
EGTFISDYSIAMEKIHQQDFVNWLLAQK, (hGIP(3-30)D15N; SEQ ID NO: 79)
EGTFISDYSIAMNKIHQQDFVNWLLAQK, (hGIP(3-30)K16A; SEQ ID NO: 80)
EGTFISDYSIAMDAIHQQDFVNWLLAQK, (hGIP(3-30)K16H; SEQ ID NO: 81)
EGTFISDYSIAMDHIHQQDFVNWLLAQK, (hGIP(3-30)K16R; SEQ ID NO: 82)
EGTFISDYSIAMDRIHQQDFVNWLLAQK, (hGIP(3-30)H18F; SEQ ID NO: 83)
EGTFISDYSIAMDKIFQQDFVNWLLAQK, (hGIP(3-30)H18W; SEQ ID NO: 84)
EGTFISDYSIAMDKIWQQDFVNWLLAQK, (hGIP(3-30)K30R; SEQ ID NO: 85)
EGTFISDYSIAMDKIHQQDFVNWLLAQR, (hGIP(3-30)K30H; SEQ ID NO: 86)
EGTFISDYSIAMDKIHQQDFVNWLLAQH (hGIP(3-30)G4K, SEQ ID NO: 87)
EKTFISDYSIAMDKIHQQDFVNWLLAQK, (hGIP(3-30)T5K, SEQ ID NO: 88)
EGKFISDYSIAMDKIHQQDFVNWLLAQK, (hGIP(3-30)F6K, SEQ ID NO: 89)
EGTKISDYSIAMDKIHQQDFVNWLLAQK, (hGIP(3-30)I7K, SEQ ID NO: 90)
EGTFKSDYSIAMDKIHQQDFVNWLLAQK, (hGIP(3-30)S8K, SEQ ID NO: 91)
EGTFIKDYSIAMDKIHQQDFVNWLLAQK, (hGIP(3-30)D9K, SEQ ID NO: 92)
EGTFISKYSIAMDKIHQQDFVNWLLAQK, (hGIP(3-30)Y10K, SEQ ID NO: 93)
EGTFISDKSIAMDKIHQQDFVNWLLAQK, (hGIP(3-30)S11K, SEQ ID NO: 94)
EGTFISDYKIAMDKIHQQDFVNWLLAQK, (hGIP(3-30)I12K, SEQ ID NO: 95)
EGTFISDYSKAMDKIHQQDFVNWLLAQK,
```

```
                   (hGIP(3-30)A13K, SEQ ID NO: 96)
EGTFISDYSIKMDKIHQQDFVNWLLAQK, (hGIP(3-30)M14K, SEQ ID NO: 97)
EGTFISDYSIAKDKIHQQDFVNWLLAQK, (hGIP(3-30)D15K, SEQ ID NO: 98)
EGTFISDYSIAMKKIHQQDFVNWLLAQK, (hGIP(3-30)I17K, SEQ ID NO: 99)
EGTFISDYSIAMDKKHQQDFVNWLLAQK, (hGIP(3-30)Q19K, SEQ ID NO: 100)
EGTFISDYSIAMDKIHKQDFVNWLLAQK, (hGIP(3-30)Q20K, SEQ ID NO: 101)
EGTFISDYSIAMDKIHQKDFVNWLLAQK, (hGIP(3-30)D21K, SEQ ID NO: 102)
EGTFISDYSIAMDKIHQQKFVNWLLAQK, (hGIP(3-30)F22K, SEQ ID NO: 103)
EGTFISDYSIAMDKIHQQDKVNWLLAQK, (hGIP(3-30)V23K, SEQ ID NO: 104)
EGTFISDYSIAMDKIHQQDFKNWLLAQK, (hGIP(3-30)N24K, SEQ ID NO: 105)
EGTFISDYSIAMDKIHQQDFVKWLLAQK, (hGIP(3-30)W25K, SEQ ID NO: 106)
EGTFISDYSIAMDKIHQQDFVNKLLAQK, (hGIP(3-30)L26K, SEQ ID NO: 107)
EGTFISDYSIAMDKIHQQDFVNWKLAQK, (hGIP(3-30)L27K, SEQ ID NO: 108)
EGTFISDYSIAMDKIHQQDFVNWLKAQK, (hGIP(3-30)A28K, SEQ ID NO: 109)
EGTFISDYSIAMDKIHQQDFVNWLLKQK, (hGIP(3-30)Q29K, SEQ ID NO: 110)
EGTFISDYSIAMDKIHQQDFVNWLLAKK (hGIP(3-30)S11K H18A, SEQ ID NO: 111)
EGTFISDYKIAMDKIAQQDFVNWLLAQK, (hGIP(3-30)S11K H18R, SEQ ID NO: 112)
EGTFISDYKIAMDKIRQQDFVNWLLAQK, (hGIP(3-30)S11K D15E, SEQ ID NO: 113)
EGTFISDYKIAMEKIHQQDFVNWLLAQK, (hGIP(3-30)S11K M14Nle, SEQ ID NO: 114)
EGTFISDYKIANleDKIHQQDFVNWLLAQK, (hGIP(3-30)S11K M14L, SEQ ID NO: 115)
EGTFISDYKIALDKIHQQDFVNWLLAQK, (hGIP(3-30)I12K H18A, SEQ ID NO: 116)
EGTFISDYSKAMDKIAQQDFVNWLLAQK, (hGIP(3-30)I12K H18R, SEQ ID NO: 117)
EGTFISDYSKAMDKIRQQDFVNWLLAQK, (hGIP(3-30)I12K D15E, SEQ ID NO: 118)
EGTFISDYSKAMEKIHQQDFVNWLLAQK, (hGIP(3-30)I12K M14Nle, SEQ ID NO: 119)
EGTFISDYSKANleDKIHQQDFVNWLLAQK, (hGIP(3-30)I12K M14L, SEQ ID NO: 120)
EGTFISDYSKALDKIHQQDFVNWLLAQK, (hGIP(3-30)A13K H18A, SEQ ID NO: 121)
EGTFISDYSIKMDKIAQQDFVNWLLAQK, (hGIP(3-30)A13K H18R, SEQ ID NO: 122)
EGTFISDYSIKMDKIRQQDFVNWLLAQK,
```

```
                  (hGIP(3-30)A13K D15E, SEQ ID NO: 123)
EGTFISDYSIKMEKIHQQDFVNWLLAQK, (hGIP(3-30)A13K M14Nle, SEQ ID NO: 124)
EGTFISDYSIKNleDKIHQQDFVNWLLAQK, (hGIP(3-30)A13K M14L, SEQ ID NO: 125)
EGTFISDYSIKLDKIHQQDFVNWLLAQK, (hGIP(3-30)D15E H18K; SEQ ID NO: 126)
EGTFISDYSIAMEKIKQQDFVNWLLAQK, (hGIP(3-30) M14Nle H18K; SEQ ID NO: 127)
EGTFISDYSIANleDKIKQQDFVNWLLAQK, (hGIP(3-30) M14L H18K; SEQ ID NO: 128)
EGTFISDYSIALDKIKQQDFVNWLLAQK, (hGIP(3-30)T5K K16R K30R, SEQ ID NO: 129)
EGKFISDYSIAMDRIHQQDFVNWLLAQR, (hGIP(3-30)D15Orn, SEQ ID NO: 130)
EGTFISDYSIAMOrnKIHQQDFVNWLLAQK, (hGIP(3-30)H18Orn; SEQ ID NO: 131)
EGTFISDYSIAMDKIOrnQQDFVNWLLAQK, (hGIP(3-30)M14L K16R H18K K30R; SEQ ID NO: 132)
EGTFISDYSIALDRIKQQDFVNWLLAQR, (SEQ ID NO: 144)
EGWFISDYSIAMEKIAQQDFVNWLLAQK,
and (SEQ ID NO: 146)
EGTFISDYSIAMDKIKQQDFVNWLLAQR,
``` wherein said peptide is modified by attaching at least one fatty acid molecule at one or more amino acid residues, such as by attaching one fatty acid molecule at one amino acid residue, with the proviso that said at least one fatty acid molecule is not attached to the amino acid residue at position 30, such as not attached to the amino acid residue K or R at position 30.

In one embodiment the fatty acid molecule is attached to a K residue within position 2 to 27 of SEQ ID NO:2 and variants thereof.

In one embodiment said peptide is C-terminally amidated (—NH$_2$).

Attachment of Fatty Acid Molecules

In one embodiment there is provided a glucose-dependent insulinotropic peptide (GIP) analogue comprising or consisting of the peptide sequence TFISDYSIAMD-KIHQQDFVNWLLAQK (hGIP5-30, SEQ ID NO:1), optionally C-terminally amidated, or a functional variant having at least 75% sequence identity to SEQ ID NO:1, wherein said peptide is modified by attaching at least one fatty acid molecule at one or more amino acid residues of SEQ ID NO:1, or a functional variant thereof, with the proviso that said at least one fatty acid molecule is not attached to the amino acid residue at position 26 of SEQ ID NO:1, or not attached to the amino acid residue at position 26 of a functional variant having at least 75% sequence identity to SEQ ID NO:1.

In another embodiment there is provided a glucose-dependent insulinotropic peptide (GIP) analogue comprising or consisting of the peptide sequence EGTFISDYSIAMD-KIHQQDFVNWLLAQK (hGIP3-30, SEQ ID NO:2), optionally C-terminally amidated, or a functional variant having at least 75% sequence identity to SEQ ID NO:2, wherein said peptide is modified by attaching at least one fatty acid molecule at one or more amino acid residues of SEQ ID NO:2, or a functional variant thereof, with the proviso that said at least one fatty acid molecule is not attached to the amino acid residue at position 30 of SEQ ID NO:2 or not attached to the amino acid residue at position 30 of a functional variant having at least 75% sequence identity to SEQ ID NO:2.

In one embodiment said at least one fatty acid molecule is not attached to the N-terminal amino acid residue at position 3 of SEQ ID NO:2, such as not attached to the N-terminal E at position 3 of SEQ ID NO:2.

In one embodiment a fatty acid molecule is attached to an amino acid residue at any one of positions 1 to 25 of SEQ ID NO:1 or a variant thereof.

In one embodiment a fatty acid molecule is attached to an amino acid residue at any one of positions 2 to 27 of SEQ ID NO:2 or a variant thereof.

In one embodiment a fatty acid molecule is attached to an amino acid residue at any one of positions 6 to 29 of SEQ ID NO:147 or a variant thereof.

In one embodiment a fatty acid molecule is attached to an amino acid residue at any one of positions 4 to 29 of SEQ ID NO:148 or a variant thereof.

In one embodiment a fatty acid molecule is attached to an amino acid residue at position 1, position 2, position 3, position 4, position 5, position 6, position 7, position 8, position 9, position 10, position 11, position 12, position 13, position 14, position 15, position 16, position 17, position 18, position 19, position 20, position 21, position 22, position 23, position 24, or position 25 of SEQ ID NO:1, or a functional variant thereof.

In one embodiment a fatty acid molecule is attached to an amino acid residue at position 2, position 3, position 4, position 5, position 6, position 7, position 8, position 9, position 10, position 11, position 12, position 13, position 14, position 15, position 16, position 17, position 18, position 19, position 20, position 21, position 22, position 23, position 24, or position 25, position 26, or position 27 of SEQ ID NO:2, or a functional variant thereof.

In one embodiment a fatty acid molecule is attached to an amino acid residue at position 6, position 7, position 8, position 9, position 10, position 11, position 12, position 13, position 14, position 15, position 16, position 17, position 18, position 19, position 20, position 21, position 22, position 23, position 24, position 25, position 26, position 27, position 28 or position 29 of SEQ ID NO:147, or a functional variant thereof.

In one embodiment at least one fatty acid molecule is attached to one or more amino acid residues in the mid-region of any one of SEQ ID NO:1 and SEQ ID NO:2, or a functional variant thereof.

In one embodiment at least one fatty acid molecule is attached to one or more amino acid residues at any one of positions 7 to 17 of SEQ ID NO:1 or 9 to 19 of SEQ ID NO:2, or a functional variant thereof.

In one embodiment at least one fatty acid molecule is attached to one or more amino acid residues at any one of positions 7 to 8, 8 to 9, 9 to 10, 10 to 11, 11 to 12, 12 to 13, 13 to 14, 14 to 15, 15 to 26, or 16 to 17 of SEQ ID NO:1 or positions 9 to 10, 10 to 11, 11 to 12, 12 to 13, 13 to 14, 14 to 15, 15 to 26, 16 to 17, 17 to 18, or 18 to 19 of SEQ ID NO:2, or a functional variant thereof.

In one embodiment at least one fatty acid molecule is attached to one or more amino acid residues at any one of positions 7, 8, and 9 of SEQ ID NO:1 or positions 9, 10, and 11 of SEQ ID NO:2, or a functional variant thereof.

In one embodiment said at least one fatty acid molecule is attached to one or more amino acid residues of the N-terminal region of any one of SEQ ID NO:1 and SEQ ID NO:2, or a functional variant thereof, with the proviso that said at least one fatty acid molecule is not attached to the amino acid residue at position 1 of SEQ ID NO:2.

In one embodiment said at least one fatty acid molecule is attached to one or more amino acid residues at any one of positions 1 to 6 of SEQ ID NO:1 or a functional variant thereof.

In one embodiment said at least one fatty acid molecule is attached to one or more amino acid residues at any one of positions 1 to 2, 2 to 3, 3 to 4, 4 to 5, or 5 to 6 of SEQ ID NO:1 or a functional variant thereof.

In one embodiment said at least one fatty acid molecule is attached to one or more amino acid residues at any one of positions 2 to 8 of SEQ ID NO:2 or a functional variant thereof.

In one embodiment said at least one fatty acid molecule is attached to one or more amino acid residues at any one of positions 2 to 3, 3 to 4, 4 to 5, 5 to 6, 6 to 7, or 7 to 8 of SEQ ID NO:2 or a functional variant thereof.

In one embodiment said at least one fatty acid molecule is attached to one or more amino acid residues of the C-terminal region of any one of SEQ ID NO:1 and SEQ ID NO:2, or a functional variant thereof, with the proviso that said at least one fatty acid molecule is not attached to the amino acid residue at position 26 of SEQ ID NO:1 or position 28 of SEQ ID NO:2.

In one embodiment said at least one fatty acid molecule is attached to one or more amino acid residues at any one of positions 18 to 25 of SEQ ID NO:1 positions 20 to 27 of SEQ ID NO:2, or a functional variant thereof.

In one embodiment said at least one fatty acid molecule is attached to one or more amino acid residues at any one of positions 18 to 19, 19 to 20, 20 to 21, 21 to 22, 22 to 23, 23 to 24, or 24 to 25 of any one of SEQ ID NO:1 and positions 20 to 21, 21 to 22, 22 to 23, 23 to 24, 24 to 25, 25 to 26, 26 to 27, or 27 to 28 SEQ ID NO:2, or a functional variant thereof.

In one embodiment a fatty acid molecule is attached to one or more amino acid residues having a side-chain aminoalkyl group (—$C_nH_{2n}NH_2$).

In one embodiment a fatty acid molecule is attached to one or more amino acid residues having a side-chain amino group ($NH_2$).

In one embodiment a fatty acid molecule is attached to the side-chain amino group of an amino acid residue.

In one embodiment a fatty acid molecule is attached to the ε (epsilon) side-chain amino group of a lysine residue (Lys, K).

In one embodiment a fatty acid molecule is attached to the δ (delta) side-chain amino group of an ornithine residue (Orn).

In one embodiment the amino acid residue having a fatty acid molecule attached is selected from the group consisting of Lys and Orn.

In one embodiment the amino acid residue having a fatty acid molecule attached is Lys.

In one embodiment the fatty acid molecule is attached to the delta-amino group of a Orn residue of a functional variant of any one of SEQ ID NO:1 and SEQ ID NO:2 comprising an Orn amino acid residue.

In one embodiment the fatty acid molecule is attached to the epsilon-amino group of a K residue of any one of SEQ ID NO:1 and SEQ ID NO:2, or a variant thereof.

In one embodiment the amino acid residue having a fatty acid molecule attached is the most N-terminal amino acid residue, such as the most N-terminal amino acid residue of SEQ ID NO:1, or a variant thereof.

In one embodiment said fatty acid molecule is attached to the alpha-amino group of an N-terminal amino acid residue. In one embodiment said fatty acid molecule is attached to the N-terminal amino acid residue at position 1 of SEQ ID NO:1, or a functional variant thereof. In one embodiment said fatty acid molecule is attached to T at position 1 of SEQ ID NO:1, or functional variant thereof.

In one embodiment a fatty acid molecule is attached to the amino acid residue at position 12 of SEQ ID NO:1 or position 14 of SEQ ID NO:2, or a functional variant thereof.

In one embodiment a fatty acid molecule is attached to K at position 12 of SEQ ID NO:1 or position 14 of SEQ ID NO:2, or a functional variant thereof, such as attached to the epsilon-amino group of K at position 12 of SEQ ID NO:1 or position 14 of SEQ ID NO:2, or a functional variant thereof.

In one embodiment a fatty acid molecule is attached to the amino acid residue at position 14 of SEQ ID NO:1 or position 16 of SEQ ID NO:2, or a variant thereof, wherein H at position 14 of SEQ ID NO:1 or position 16 of SEQ ID NO:2 has been substituted with K (or Orn) in any one of SEQ ID NO:1 and SEQ ID NO:2.

In one embodiment a fatty acid molecule is attached to the epsilon-amino group of K at position 14 of SEQ ID NO:1 or position 16 of SEQ ID NO:2, or a variant thereof.

In one embodiment a fatty acid molecule is attached to the epsilon-amino group of K at position 18 of a peptide selected from TFISDYSIAMDKIKQQDFVNWLLAQK (hGIP(5-30)H18K; SEQ ID NO:8), EGTFISDYSIAMD-KIKQQDFVNWLLAQK (hGIP(3-30)H18K; SEQ ID NO:75), or a functional variant thereof.

In one embodiment a fatty acid molecule is attached to the epsilon-amino group of a K residue at any one position of SEQ ID NO:1 and SEQ ID NO:2, or functional variants thereof.

In one embodiment a fatty acid molecule is attached to the delta-amino group of Orn at position 18 of a peptide selected from TFISDYSIAMDKIOrnQQDFVNWLLAQK (hGIP(5-30)H18Orn; SEQ ID NO:62), EGTFISDYSIAMDKI-OrnQQDFVNWLLAQK (hGIP(3-30)H18Orn; SEQ ID NO:131), or a functional variant thereof.

In one embodiment the K at position 12 of SEQ ID NO:1 or position 14 of SEEQ ID NO:2, and/or the K at position 26 of SEQ ID NO:1 or position 28 of SEQ ID NO:2, or a functional variant thereof, are individually substituted with any amino acid when a fatty acid molecule is attached to an amino acid residue at a position other than position 12 and position 26 of SEQ ID NO:1, or position 14 and position 28 of SEQ ID NO:2, or a functional variant thereof.

In one embodiment a fatty acid molecule is attached to the epsilon-amino group of K at position 15 of a peptide selected from TFISDYSIAMKKIHQQDFVNWLLAQK (hGIP(5-30)D15K, SEQ ID NO:30), EGTFISDYSIAMK-KIHQQDFVNWLLAQK (hGIP(3-30)D15K, SEQ ID NO:98), or a functional variant thereof.

In one embodiment a fatty acid molecule is attached to the delta-amino group of Orn at position 15 of a peptide selected from TFISDYSIAMOrnKIHQQDFVNWLLAQK (hGIP(5-30)D15Orn, SEQ ID NO:61), EGTFISDYSIA-MOrnKIHQQDFVNWLLAQK (hGIP(3-30)D15Orn, SEQ ID NO:130), or a functional variant thereof.

In one embodiment a fatty acid molecule is attached to the epsilon-amino group of K at position 11 of a peptide selected from TFISDYKIAMDKIHQQDFVNWLLAQK (hGIP(5-30)S11K, SEQ ID NO:26), EGTFISDYKIAMD-KIHQQDFVNWLLAQK (hGIP(3-30)S11K, SEQ ID NO:94), or a functional variant thereof.

In one embodiment a fatty acid molecule is attached to the delta-amino group of Orn at position 11 of a peptide selected from TFISDYOrnlAMDKIHQQDFVNWLLAQK (hGIP(5-30)S11Orn, SEQ ID NO:133), EGTFISDYOrnlAMD-KIHQQDFVNWLLAQK (hGIP(3-30)S11Orn, SEQ ID NO:134), or a functional variant thereof.

In one embodiment a fatty acid molecule is attached to the epsilon-amino group of K at position 12 of a peptide selected from TFISDYSKAMDKIHQQDFVNWLLAQK (hGIP(5-30)I12K, SEQ ID NO:27), EGTFISDYSKAMD-KIHQQDFVNWLLAQK (hGIP(3-30)I12K, SEQ ID NO:95), or a functional variant thereof.

In one embodiment a fatty acid molecule is attached to the delta-amino group of Orn at position 12 of a peptide selected from TFISDYSOrnAMDKIHQQDFVNWLLAQK (hGIP(5-30)I12Orn, SEQ ID NO:135), EGTFISDYSOrnAMD-KIHQQDFVNWLLAQK (hGIP(3-30)I12Orn, SEQ ID NO:136), or a functional variant thereof.

In one embodiment a fatty acid molecule is attached to the epsilon-amino group of K at position 13 of a peptide selected from TFISDYSIKMDKIHQQDFVNWLLAQK (hGIP(5-30)A13K, SEQ ID NO:28), EGTFISDYSIKMD-KIHQQDFVNWLLAQK (hGIP(3-30)A13K, SEQ ID NO:96), or a functional variant thereof.

In one embodiment a fatty acid molecule is attached to the delta-amino group of Orn at position 13 of a peptide selected from TFISDYSIOrnMDKIHQQDFVNWLLAQK (hGIP(5-30)A13Orn, SEQ ID NO:137), EGTFISDYSIOrnMD-KIHQQDFVNWLLAQK (hGIP(3-30)A13Orn, SEQ ID NO:138), or a functional variant thereof.

In one embodiment a fatty acid molecule is attached to the amino acid residue at position 5 of SEQ ID NO:1 or position 7 of SEQ ID NO:2, or a variant thereof, wherein D at position 5 of SEQ ID NO:1 or position 7 of SEQ ID NO:2 has been substituted with K or Orn in any one of SEQ ID NO:1 and SEQ ID NO:2.

In one embodiment a fatty acid molecule is attached to the epsilon-amino group of K at position 9 of a peptide selected from TFISKYSIAMDKIHQQDFVNWLLAQK (hGIP(5-30)D9K, SEQ ID NO:24), EGTFISKYSIAMD-KIHQQDFVNWLLAQK (hGIP(3-30)D9K, SEQ ID NO:92), or a functional variant thereof.

In one embodiment a fatty acid molecule is attached to the delta-amino group of Orn at position 9 of a peptide selected from TFISKYSIAMDKIHQQDFVNWLLAQK (hGIP(5-30)D9Orn, SEQ ID NO:24), EGTFISKYSIAMD-KIHQQDFVNWLLAQK (hGIP(3-30)D9Orn, SEQ ID NO:92), or a functional variant thereof.

In one embodiment a fatty acid molecule is attached to the amino acid residue at position17 of SEQ ID NO:1 or position 19 of SEQ ID NO:2, or a variant thereof, wherein D at position 17 of SEQ ID NO:1 or position 19 of SEQ ID NO:2 has been substituted with K or Orn in any one of SEQ ID NO:1 and SEQ ID NO:2.

In one embodiment a fatty acid molecule is attached to the epsilon-amino group of K at position 21 of a peptide selected from TFISDYSIAMDKIHQQKFVNWLLAQK (hGIP(5-30)D21K, SEQ ID NO:34), EGTFISDYSIAMD-KIHQQKFVNWLLAQK (hGIP(3-30)D21K, SEQ ID NO:102), or a functional variant thereof.

In one embodiment a fatty acid molecule is attached to the delta-amino group of Orn at position 21 of a peptide selected from TFISDYSIAMDKIHQQOrnFVNWLLAQK (hGIP(5-30)D21Orn, SEQ ID NO:139), EGTFISDYSIAMD-KIHQQOrnFVNWLLAQK (hGIP(3-30)D21Orn, SEQ ID NO:140), or a functional variant thereof.

In one embodiment a fatty acid molecule is attached to the amino acid residue at position 1 of SEQ ID NO:2, or a variant thereof, wherein T at position 1 has been substituted with K or Orn in SEQ ID NO:2.

In one embodiment a fatty acid molecule is attached to the epsilon-amino group of K at position 5 of a peptide of sequence EGKFISDYSIAMDKIHQQDFVNWLLAQK (hGIP(3-30)T5K, SEQ ID NO:88), or a functional variant thereof.

In one embodiment a fatty acid molecule is attached to the delta-amino group of Orn at position 5 of a peptide of sequence EGOrnFISDYSIAMDKIHQQKFVNWLLAQK (hGIP(3-30)T5Orn, SEQ ID NO:141), or a functional variant thereof.

In one embodiment a fatty acid molecule is attached to the amino acid residue at position 13 of SEQ ID NO:2, or a variant thereof, wherein D at position 13 has been substituted with K or Orn in SEQ ID NO:2.

In one embodiment a fatty acid molecule is attached to the epsilon-amino group of K at position 15 of a peptide of sequence EGTFISDYSIAMKKIHQQDFVNWLLAQK (hGIP(3-30)D15K, SEQ ID NO:98), or a functional variant thereof.

In one embodiment a fatty acid molecule is attached to the delta-amino group of Orn at position 15 of a peptide of sequence EGTFISDYSIAMOrnKIHQQKFVNWLLAQK (hGIP(3-30)D15Orn, SEQ ID NO:142), or a functional variant thereof.

In one embodiment a fatty acid molecule is attached to the amino acid residue at position 18 of SEQ ID NO:2, or a variant thereof, wherein Q at position 18 has been substituted with K or Orn in SEQ ID NO:2.

In one embodiment a fatty acid molecule is attached to the epsilon-amino group of K at position 20 of a peptide of sequence EGTFISDYSIAMDKIHQKDFVNWLLAQK (hGIP(3-30)Q20K, SEQ ID NO:101), or a functional variant thereof.

In one embodiment a fatty acid molecule is attached to the delta-amino group of Orn at position 20 of a peptide of sequence EGTFISDYSIAMDKIHQOrnKFVNWLLAQK (hGIP(3-30)Q20Orn, SEQ ID NO:143), or a functional variant thereof.

In one embodiment said peptide is modified by attaching a (one) fatty acid molecule at one (a single) amino acid residue of any one of SEQ ID NO:1 and SEQ ID NO:2, or a functional variant thereof.

In one embodiment the peptide of the GIP peptide analogue comprises no more than one K amino acid residue, which K amino acid residue is modified by attaching a fatty acid molecule to the epsilon-amino group of K.

In one embodiment the fatty acid molecule according to the present disclosure is a straight-chain fatty acid.

In one embodiment the fatty acid molecule according to the present disclosure is a branched fatty acid.

In one embodiment the fatty acid molecule according to the present disclosure is a monoacyl fatty acid molecule, comprising one fatty acid.

In one embodiment the fatty acid molecule according to the present disclosure is a diacyl fatty acid molecule.

In one embodiment the fatty acid molecule according to the present disclosure is a diacyl fatty acid molecule comprising two fatty acids.

In one embodiment the fatty acid molecule according to the present disclosure is a diacyl fatty acid molecule containing two carboxyl functional groups.

In one embodiment the fatty acid molecule according to the present disclosure comprises an acyl group of the formula $CH_3(CH_2)_nCO-$, wherein n is an integer from 4 to 24.

In one embodiment said fatty acid molecule comprises an acyl group selected from the group consisting of $CH_3(CH_2)_6CO-$, $CH_3(CH_2)_8CO-$, $CH_3(CH_2)_{10}CO-$, $CH_3(CH_2)_{12}CO-$, $CH_3(CH_2)_{14}CO-$, $CH_3(CH_2)_{16}CO-$, $CH_3(CH_2)_{18}CO-$, $CH_3(CH_2)_{20}CO-$ and $CH_3(CH_2)_{22}CO-$.

In one embodiment said fatty acid molecule comprises an acyl group selected from the group consisting of $CH_3(CH_2)_{10}CO-$ (lauryl, C12), $CH_3(CH_2)_{12}CO-$ (myristoyl, C14), $CH_3(CH_2)_{14}CO-$ (palmitoyl, C16) and $CH_3(CH_2)_{16}CO-$ (stearyl, C18).

In one embodiment said fatty acid molecule is a monoacyl fatty acid selected from the group consisting of $CH_3(CH_2)_{10}CO-$ (lauryl, C12), $CH_3(CH_2)_{12}CO-$ (myristoyl, C14), $CH_3(CH_2)_{14}CO-$ (palmitoyl, C16) and $CH_3(CH_2)_{16}CO-$ (stearyl, C18).

In one embodiment said fatty acid molecule comprises two fatty acids each selected from the group consisting of $CH_3(CH_2)_{10}CO-$ (lauryl, C12), $CH_3(CH_2)_{12}CO-$ (myristoyl, C14), $CH_3(CH_2)_{14}CO-$ (palmitoyl, C16) and $CH_3(CH_2)_{16}CO-$ (stearyl, C18).

In one embodiment said fatty acid molecule comprises an acyl group of the formula $COOH(CH_2)_nCO-$ (dicarboxylic acid), wherein n is an integer from 4 to 24.

In one embodiment said fatty acid molecule comprises an acyl group selected from the group consisting of $COOH(CH_2)_{14}CO-$, $COOH(CH_2)_{16}CO-$, $COOH(CH_2)_{18}CO-$ and $COOH(CH_2)_{20}CO-$.

In one embodiment said fatty acid molecule is selected from C12, C14, C16 and C18.

In one embodiment said fatty acid molecule is selected from C14 diacid, C16 diacid and C18 diacid.

In one embodiment said fatty acid molecule is palmitoyl.

In one embodiment said fatty acid molecule is 1,16-Hexadecanedioic acid/hexadecanedioic acid.

In one embodiment said fatty acid molecule is stearyl.

In one embodiment said fatty acid molecule is 1,18-Octadecanedioic acid/octadecanedioic acid.

A fatty acid molecule may be attached to an amino acid residue in such a way that a carboxyl group of the fatty acid molecule forms an amide bond with an amino group of the amino acid residue.

Attachment of fatty acid molecules to a peptide herein can occur either directly in indirectly, i.e. via a linker or spacer.

In one embodiment the fatty acid molecule according to the present disclosure is attached to an amino acid residue directly.

In one embodiment the fatty acid molecule according to the present disclosure is directly attached to the alpha-amino group of an amino acid residue, wherein said amino acid residue is the N-terminal amino acid residue.

In one embodiment the fatty acid molecule according to the present disclosure is directly attached to the epsilon-amino group of a Lys residue.

In one embodiment the fatty acid molecule according to the present disclosure is directly attached to the delta-amino group of an Orn residue.

In one embodiment the fatty acid molecule according to the present disclosure is attached to an amino acid residue via a linker or spacer.

In one embodiment the fatty acid molecule according to the present disclosure is attached to the alpha-amino group of an amino acid residue via a linker or spacer, wherein said amino acid residue is the N-terminal amino acid residue.

In one embodiment the fatty acid molecule according to the present disclosure is attached to the epsilon-amino group of a Lys residue via linker or spacer.

In one embodiment the fatty acid molecule according to the present disclosure is attached to the delta-amino group of an Orn residue via linker or spacer.

In one embodiment the fatty acid molecule may be attached to an amino acid residue by means of a spacer (or linker) in such a way that a carboxyl group of the spacer forms an amide bond with an amino group of the fatty acid molecule.

In one embodiment the spacer is an α,ω-amino acid. Examples of suitable spacers are succinic acid, Lys, Glu or Asp, or a dipeptide such as Gly-Lys. When the spacer is succinic acid, one carboxyl group thereof may form an amide bond with an amino group of the amino acid residue, and the other carboxyl group thereof may form an amide bond with an amino group of the fatty acid molecule. When the spacer is Lys, Glu or Asp, the carboxyl group thereof may form an amide bond with an amino group of the amino acid residue, and the amino group thereof may form an amide bond with a carboxyl group of the fatty acid molecule. When Lys is used as the spacer, a further spacer may in some instances be inserted between the ε-amino group of Lys and the fatty acid molecule. In one embodiment such a further spacer is succinic acid which forms an amide bond with the ε-amino group of Lys and with an amino group present in the fatty acid molecule. Other spacers are Nε-(γ-L-glutamyl), Nε-(β-L-asparagyl), Nε-glycyl, and Nε-(α-(γ-aminobutanoyl)).

In one embodiment the spacer is a hydrophilic linker. In one embodiment the spacer is a non-natural amino acid hydrophilic linker.

In one embodiment the spacer is selected from the group consisting of γ-aminobutanoyl (γ-aminobutyric acid), γ-glutamyl (γ-glutamic acid), β-asparagyl, β-alanyl and glycyl. In one embodiment the spacer comprises one or more of γ-aminobutanoyl (γ-aminobutyric acid), γ-glutamyl (γ-glutamic acid), β-asparagyl, β-alanyl and glycyl.

In one embodiment the spacer is a repeat of individual spacer moieties. In one embodiment the spacer is a repeat of identical spacer moieties. In one embodiment the spacer is a repeat of different spacer moieties.

In one embodiment the spacer is γ-glutamic acid-8-amino-3,6-dioxaoctanoic acid (γ-Glu)-AEEAc), or a repeat thereof.

In one embodiment the spacer comprises one or more repeats of γ-glutamic acid-8-amino-3,6-dioxaoctanoic acid (γ-Glu)-AEEAc$_n$).

In one embodiment the spacer is [γ-glutamic acid-8-amino-3,6-dioxaoctanoic acid]$_n$ (γ-Glu)-AEEAc$_n$), wherein n is an integer between 1 and 50.

In one embodiment the spacer is [γ-glutamic acid-8-amino-3,6-dioxaoctanoic acid]$_n$ (γ-Glu)-AEEAc$_n$), wherein n is an integer between 1 and 50, such as an integer between 1-2, 2-3, 3-4, 4-5, 5-6, 6-7, 7-8, 8-9, 9-10, 10-11, 11-12, 12-13, 13-14, 14-15, 15-20, 20-25, 25-30, 30-35, 35-40, 40-45, 45-50.

In one embodiment the spacer is [γ-glutamic acid-8-amino-3,6-dioxaoctanoic acid]$_n$ (γ-Glu)-AEEAc$_n$), wherein n is an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50. In one embodiment the spacer is an amino acid residue except Cys. In one embodiment the spacer is 4-Abu. In one embodiment the spacer is γ-aminobuturic acid.

In another embodiment the spacer is a dipeptide, such as a dipeptide wherein the C-terminal amino acid residue is Lys, His or Trp, preferably Lys, and wherein the N-terminal amino acid residue is selected from the group comprising Ala, Arg, Asp, Asn, Gly, Glu, Gln, Ile, Leu, Val, Phe and Pro. In one embodiment the dipeptide spacer is Gly-Lys.

In one embodiment the spacer comprises one or more moieties selected from the group consisting of γ-aminobutanoyl (γ-aminobutyric acid), γ-glutamyl (γ-glutamic acid), β-asparagyl, β-alanyl and glycyl. In one embodiment the spacer comprises one or more of γ-aminobutanoyl (γ-aminobutyric acid), γ-glutamyl (γ-glutamic acid), β-asparagyl, β-alanyl, glycyl, γ-glutamic acid-8-amino-3,6-dioxaoctanoic acid (γ-Glu-AEEAc$_n$, wherein n is an integer between 1 and 50), an amino acid residue except Cys, 4-Abu, γ-aminobuturic acid and a dipeptide.

In another embodiment spacer is an unbranched alkane α,ω-dicarboxylic acid group having from 1 to 7 methylene groups, preferably two methylene groups, which spacer forms a bridge between an amino group of the parent peptide and an amino group of the fatty acid molecule.

GIP(5-30) Peptides with Fatty Acid

In one embodiment the GIP analogue as defined herein is selected from the group consisting of:

```
                                            (SEQ ID NO: 1)
TFISDYSIAMDKIHQQDFVNWLLAQK-C12/T1, (SEQ ID NO: 1)
TFISDYSIAMDKIHQQDFVNWLLAQK-C12/K12, (SEQ ID NO: 1)
TFISDYSIAMDKIHQQDFVNWLLAQK-C14/T1, (SEQ ID NO: 1)
TFISDYSIAMDKIHQQDFVNWLLAQK-C14/K12, (SEQ ID NO: 1)
TFISDYSIAMDKIHQQDFVNWLLAQK-C16/T1, (SEQ ID NO: 1)
TFISDYSIAMDKIHQQDFVNWLLAQK-C16/K12, (SEQ ID NO: 1)
TFISDYSIAMDKIHQQDFVNWLLAQK-C18/T1, (SEQ ID NO: 1)
TFISDYSIAMDKIHQQDFVNWLLAQK-C18/K12, (SEQ ID NO: 5)
TFISDYSIAMDRIKQQDFVNWLLAQR-C16/T1, (SEQ ID NO: 5)
TFISDYSIAMDRIKQQDFVNWLLAQR-C16/K14, (SEQ ID NO: 6)
TFISDYSIAMDRIHQQDFVNWLLAQR-C16/T1, (SEQ ID NO: 1)
TFISDYSIAMDKIHQQDFVNWLLAQK-C14-diacid/T1, (SEQ ID NO: 1)
TFISDYSIAMDKIHQQDFVNWLLAQK-C16-diacid/T1, (SEQ ID NO: 1)
TFISDYSIAMDKIHQQDFVNWLLAQK-C18-diacid/T1, (SEQ ID NO: 1)
TFISDYSIAMDKIHQQDFVNWLLAQK-C14-diacid/K12, (SEQ ID NO: 1)
TFISDYSIAMDKIHQQDFVNWLLAQK-C16-diacid/K12, (SEQ ID NO: 1)
TFISDYSIAMDKIHQQDFVNWLLAQK-C18-diacid/K12, (SEQ ID NO: 8)
TFISDYSIAMDKIKQQDFVNWLLAQK-C16-diacid/K14, (SEQ ID NO: 8)
TFISDYSIAMDKIKQQDFVNWLLAQK-C18-diacid/K14, (SEQ ID NO: 5)
TFISDYSIAMDRIKQQDFVNWLLAQR-C16-diacid/K14, (SEQ ID NO: 20)
KFISDYSIAMDKIHQQDFVNWLLAQK-C14-diacid/K1, (SEQ ID NO: 20)
KFISDYSIAMDKIHQQDFVNWLLAQK-C16-diacid/K1, (SEQ ID NO: 20)
KFISDYSIAMDKIHQQDFVNWLLAQK-C18-diacid/K1, (SEQ ID NO: 64)
KFISDYSIAMDRIHQQDFVNWLLAQR-C16-diacid/K1, (SEQ ID NO: 64)
KFISDYSIAMDRIHQQDFVNWLLAQR-C18-diacid/K1, (SEQ ID NO: 26)
TFISDYKIAMDKIHQQDFVNWLLAQK-C16-diacid/K7, (SEQ ID NO: 66)
TFISDYKIAMDRIHQQDFVNWLLAQR-C16-diacid/K7, (SEQ ID NO: 26)
TFISDYKIAMDKIHQQDFVNWLLAQK-C18-diacid/K7, (SEQ ID NO: 66)
TFISDYKIAMDRIHQQDFVNWLLAQR-C18-diacid/K7, (SEQ ID NO: 27)
TFISDYSKAMDKIHQQDFVNWLLAQK-C16-diacid/K8, (SEQ ID NO: 68)
TFISDYSKAMDRIHQQDFVNWLLAQR-C16-diacid/K8, (SEQ ID NO: 27)
TFISDYSKAMDKIHQQDFVNWLLAQK-C18-diacid/K8, (SEQ ID NO: 68)
TFISDYSKAMDRIHQQDFVNWLLAQR-C18-diacid/K8, (SEQ ID NO: 28)
TFISDYSIKMDKIHQQDFVNWLLAQK-C16-diacid/K9, (SEQ ID NO: 70)
TFISDYSIKMDRIHQQDFVNWLLAQR-C16-diacid/K9, (SEQ ID NO: 28)
TFISDYSIKMDKIHQQDFVNWLLAQK-C18-diacid/K9, (SEQ ID NO: 70)
TFISDYSIKMDRIHQQDFVNWLLAQR-C18-diacid/K9, (SEQ ID NO: 6)
TFISDYSIAMDRIHQQDFVNWLLAQR-C16-diacid/K12, (SEQ ID NO: 6)
TFISDYSIAMDRIHQQDFVNWLLAQR-C18-diacid/K12, (SEQ ID NO: 5)
TFISDYSIAMDRIKQQDFVNWLLAQR-C18-diacid/K14, (SEQ ID NO: 34)
TFISDYSIAMDKIHQQKFVNWLLAQK-C16-diacid/K17, (SEQ ID NO: 145)
TFISDYSIAMDRIHQQKFVNWLLAQR-C16-diacid/K17, (SEQ ID NO: 34)
TFISDYSIAMDKIHQQKFVNWLLAQK-C18-diacid/K17,
and
```

TFISDYSIAMDRIHQQKFVNWLLAQR-C18-diacid/K17, (SEQ ID NO: 145)

or a functional variant thereof,
wherein said fatty acid is attached directly or via a linker/spacer as defined herein.

It follows that C12 is the fatty acid $CH_3(CH_2)_{10}CO$— (lauryl); C14 is the fatty acid $CH_3(CH_2)_{12}CO$— (myristoyl); C16 is the fatty acid $CH_3(CH_2)_{14}CO$— (palmitoy) and C18 is the fatty acid $CH_3(CH_2)_{16}CO$— (stearyl). The suffix "-diacid" means that the fatty acid molecule is a diacyl fatty acid molecule. No such suffix refers to a monoacyl fatty acid molecule.

In one embodiment said peptide is C-terminally amidated (—$NH_2$).

In one embodiment the GIP analogue is selected from the group consisting of:
hGIP(5-30)NH2[H18K]-C16/K18+γ-glutamic acid,
hGIP(5-30)NH2[H18K]-C16/K18+γ-aminobuturic acid,
hGIP(5-30)NH2[H18K]-C16/K18+β-alanine, and
hGIP(5-30)NH2[H18K]-C16/K18+γ-glutamic acid+ one or more repeats of 8-amino-3,6-dioxaoctanoic acid.

In one embodiment the GIP analogue is selected from the group consisting of:
hGIP(5-30)NH2[H18K]-C16-diacid/K18+γ-glutamic acid,
hGIP(5-30)NH2[H18K]-C16-diacid/K18+γ-aminobuturic acid,
hGIP(5-30)NH2[H18K]-C16-diacid/K18+β-alanine, and
hGIP(5-30)NH2[H18K]-C16-diacid/K18+γ-glutamic acid+ one or more repeats of 8-amino-3,6-dioxaoctanoic acid.

GIP(3-30) Peptides with Fatty Acid

In one embodiment the GIP analogue as defined herein is selected from the group consisting of:

EGTFISDYSIAMDKIHQQDFVNWLLAQK-C12/K14, (SEQ ID NO: 2)

EGTFISDYSIAMDKIHQQDFVNWLLAQK-C16/K14, (SEQ ID NO: 2)

EGWFISDYSIAMEKIAQQDFVNWLLAQK-C16/K14, (SEQ ID NO: 144)

EGTFISDYSIAMDKIHQQDFVNWLLAQK-C14/K14, (SEQ ID NO: 2)

EGTFISDYSIAMDKIHQQDFVNWLLAQK-C18/K14, (SEQ ID NO: 2)

EGTFISDYSIAMDKIKQQDFVNWLLAQK-C12/K16, (SEQ ID NO: 75)

EGTFISDYSIAMDKIKQQDFVNWLLAQK-C16/K16, (SEQ ID NO: 75)

EGTFISDYSIAMEKIAQQDFVNWLLAQK-C16/K14, (SEQ ID NO: 76)

EGTFISDYSIAMDKIKQQDFVNWLLAQK-C16-diacid/K16, (SEQ ID NO: 75)

EGTFISDYSIAMDKIKQQDFVNWLLAQK-C18-diacid/K16, (SEQ ID NO: 75)

EGTFISDYSIAMDRIKQQDFVNWLLAQR-C16-diacid/K16, (SEQ ID NO: 72)

EGTFISDYSIAMDKIKQQDFVNWLLAQR-C18/K16, (SEQ ID NO: 146)

EGTFISDYSIAMDKIKQQDFVNWLLAQR-C16/K16, (SEQ ID NO: 146)

EGTFISDYSIALDKIKQQDFVNWLLAQK-C16/K16, (SEQ ID NO: 128)

EGTFISDYSIAMDKIKQQDFVNWLLAQK-C16-diacid/K16, (SEQ ID NO: 75)

EGTFISDYSIAMDRIKQQDFVNWLLAQR-C16-diacid/K16, and (SEQ ID NO: 72)

EGTFISDYSIAMDKIKQQDFVNWLLAQK-C18/K16, (SEQ ID NO: 75)

EGKFISDYSIAMDKIHQQDFVNWLLAQK-C16-diacid/K3, (SEQ ID NO: 88)

EGKFISDYSIAMDRIHQQDFVNWLLAQR-C16-diacid/K3, (SEQ ID NO: 129)

EGKFISDYSIAMDKIHQQDFVNWLLAQK-C18-diacid/K3, (SEQ ID NO: 88)

EGKFISDYSIAMDRIHQQDFVNWLLAQR-C18-diacid/K3, and (SEQ ID NO: 129)

EGTFISDYSIAMDRIKQQDFVNWLLAQR-C18-diacid/K16, (SEQ ID NO: 72)

or a functional variant thereof,
wherein said fatty acid is attached directly or via a linker/spacer as defined herein.

In one embodiment said peptide is C-terminally amidated (—$NH_2$).

In one embodiment the GIP analogue is selected from the group consisting of:
AT164 [hGIP(3-30)NH2[H18K]-C16/K18+y-glutamic acid],
AT165 [hGIP(3-30)NH2[H18K]-C16/K18+y-aminobuturic acid],
AT166 [hGIP(3-30)NH2[H18K]-C16/K18+β-alanine], and
AT167 [hGIP(3-30)NH2[H18K]-C16/K18+y-glutamic acid+ one or more repeats of 8-amino-3,6-dioxaoctanoic acid].

In one embodiment the GIP analogue is selected from the group consisting of:
[hGIP(3-30)NH2[H18K]-C16-diacid/K18+y-glutamic acid],
[hGIP(3-30)NH2[H18K]-C16-diacid/K18+y-aminobuturic acid],
[hGIP(3-30)NH2[H18K]-C16-diacid/K18+β-alanine], and
[hGIP(3-30)NH2[H18K]-C16-diacid/K18+y-glutamic acid+ one or more repeats of 8-amino-3,6-dioxaoctanoic acid].

Compound

It is a further aspect to provide a compound comprising or consisting of a peptide as defined herein. In one embodiment, said compound is formulated as a peptide monomer (i.e. comprising 1 copy of the peptide), whereas in another embodiment, said compound is formulated as a peptide multimer.

Multimeric Compound

In one embodiment the peptide according to the present disclosure is formulated as a multimer. A multimer is a protein comprising or consisting of multiple peptide monomers. A multimer is an aggregate of multiple molecules that is usually held together with non-covalent bonds. This definition distinguishes a multimer from a polymer, which is a series of monomers that are held together with covalent bonds.

A peptide sequence of the present disclosure is in one embodiment connected to another (identical or non-identical) peptide sequence of the present disclosure by a chemical bond or through a linker group. In some embodiments a peptide of the disclosure is formulated as an oligomer or multimer of monomers, wherein each monomer is as a peptide sequence as defined according to the present disclosure.

Thus, according to the disclosure a multimeric compound is in one embodiment a polymer comprising two or more peptide sequences of the disclosure, said peptide sequences being identical or non-identical, wherein at least one of the two or more peptide sequences is a peptide according to the present disclosure. Preferably, both peptide sequences are a peptide according to the present disclosure.

In one embodiment the multimeric compound is a dimer, comprising two peptides according to the present disclosure, said two peptides being identical or non-identical with respect to each other.

In another embodiment the multimeric compound is a trimer, comprising three peptides according to the present disclosure, said peptides being identical or non-identical with respect to each other.

In another embodiment the multimeric compound is a tetramer, comprising four peptides according to the present disclosure, said peptides being identical or non-identical with respect to each other.

In one embodiment the multimeric compound is a dendrimer, such as a tetrameric or octameric dendrimer. Dendrimers are repeatedly branched, roughly spherical large molecules, typically symmetric around the core, and often adopts a spherical three-dimensional morphology.

Dendrimers according to the present disclosure may comprise 4 peptides, 8 peptides, 16 peptides, or 32 peptides. In one particular embodiment said dendrimer comprises four peptides (i.e. a tetrameric dendrimer) or eight peptides (octameric dendrimer).

In some particular embodiments, the multimeric compound comprises two identical amino acid sequences of the present invention (dimer) or the compound comprises four identical copies of an amino acid sequence of the present disclosure (tetrameric dendrimer).

The multimers according to the disclosure is in one embodiment made by linking two or more peptide monomers via a peptide bond or a linker group. In one embodiment they are linked to a lysine backbone, such as a lysine residue (each peptide chain is linked to a single lysine residue), or coupled to a polymer carrier, for example a protein carrier. Said linker group in one embodiment comprises a plurality of lysine residues, such as a core moiety having a plurality of lysine residues, such as seen in a lysine-based dendrimeric structure containing three, seven, fifteen and more lysine residues However, any other linking of peptide monomers known to the skilled person may be envisioned.

The linking in one embodiment occurs at the N-terminal and/or C-terminal end of the peptide monomers.

In one embodiment there is provided a multimeric compound, consisting of A) one or more glucose-dependent insulinotropic peptide (GIP) analogues of formula 1 (hGIP5-30, SEQ ID NO:1):

```
 1    2    3    4    5    6    7    8    9   10   11   12
 T  - F  - I  - S  - D  - Y  - S  - I  - A  - M  - D  - K  -

13   14   15   16   17   18   19   20   21   22   23   24
 I  - H  - Q  - Q  - D  - F  - V  - N  - W  - L  - L  - A  -

25   26
 Q  - K
``` wherein said peptide optionally further comprises the dipeptide E-G at the N-terminus (hGIP3-30, SEQ ID NO:2), or a functional variant having at least 75% sequence identity to any one of SEQ ID NO:1 and SEQ ID NO:2, wherein said peptide is modified by attaching at least one fatty acid molecule at one or more amino acid residues of any one of SEQ ID NO:1 and SEQ ID NO:2, or a functional variant having at least 75% sequence identity to any one of SEQ ID NO:1 and SEQ ID NO:2, with the proviso that said at least one fatty acid molecule is not attached to the amino acid residue at position 26 of SEQ ID NO:1 or position 28 of SEQ ID NO:2, or a functional variant having at least 75% sequence identity to any one of SEQ ID NO:1 and SEQ ID NO:2, and
B) optionally one or more linker groups.

Determining Antagonist Properties and Affinity

In order to determine whether a peptide is an antagonist of the GIPR, methods known in the art may be employed, for example by determining the I050 of the peptide. This can be done by constructing a dose-response curve and examining the effect of different concentrations of the peptide on reversing agonist activity. The agonist can be GIP1-42, for example hGIP-1-42 or hGIP1-30. The GIPR can be hGIPR, rGIPR, mGIPR, dog GIPR, pig GIPR or the *Macaca mulatta* GIPR. I050 values can be calculated for a given antagonist by determining the concentration needed to inhibit half of the maximum biological response of the agonist. A method for determining whether a peptide is an antagonist is described in example 4, but other methods known in the art may also be used. For example, Schild plot analysis may be performed on hGIP1-42 cAMP dose-response curves with increasing concentrations of GIP-derived peptides. In this way, the type of antagonist activity may also be determined.

Heterologous competition binding experiments may be performed in order to measure the affinity of the peptide for a GIPR, i.e. how efficiently the peptide is capable of displacing a given GIP1-42, for example hGIP1-42. These competition binding experiments may be performed by methods known in the art. For example, GIP1-42 may be radioactively labelled, for example with 125I. Other suitable isotopes are known to the skilled person.

Method of Treatment

It is also an aspect to provide a peptide as defined herein, or a composition comprising the peptide, for use as a medicament.

In one embodiment there is provided a glucose-dependent insulinotropic peptide (GIP) analogue of formula 1 (hGIP5-30, SEQ ID NO:1):

```
 1    2    3    4    5    6    7    8    9   10   11   12
 T  - F  - I  - S  - D  - Y  - S  - I  - A  - M  - D  - K  -

13   14   15   16   17   18   19   20   21   22   23   24
 I  - H  - Q  - Q  - D  - F  - V  - N  - W  - L  - L  - A  -

25   26
 Q  - K
``` wherein said peptide optionally further comprises the dipeptide E-G at the N-terminus (hGIP3-30, SEQ ID NO:2), or a functional variant having at least 75% sequence identity to any one of SEQ ID NO:1 and SEQ ID NO:2,
wherein said peptide is modified by attaching at least one fatty acid molecule at one or more amino acid residues of any one of SEQ ID NO:1 and SEQ ID NO:2, or a functional variant having at least 75% sequence identity to any one of SEQ ID NO:1 and SEQ ID NO:2,
with the proviso that said at least one fatty acid molecule is not attached to the amino acid residue at position 26 of SEQ ID NO:1 or position 28 of SEQ ID NO:2, or a functional variant having at least 75% sequence identity to any one of SEQ ID NO:1 and SEQ ID NO:2,
for use as a medicament.

In another embodiment there is provided a glucose-dependent insulinotropic peptide (GIP) analogue of formula 1 (hGIP5-30, SEQ ID NO:1):

```
1   2   3   4   5   6   7   8   9   10  11  12
T - F - I - S - D - Y - S - I - A - M - D - K -

13  14  15  16  17  18  19  20  21  22  23  24
I - H - Q - Q - D - F - V - N - W - L - L - A -

25  26
Q - K
``` wherein said peptide optionally further comprises the dipeptide E-G at the N-terminus (hGIP3-30, SEQ ID NO:2), or a functional variant having at least 75% sequence identity to any one of SEQ ID NO:1 and SEQ ID NO:2,
wherein said peptide is modified by attaching at least one fatty acid molecule at one or more amino acid residues of any one of SEQ ID NO:1 and SEQ ID NO:2, or a functional variant having at least 75% sequence identity to any one of SEQ ID NO:1 and SEQ ID NO:2,
with the proviso that said at least one fatty acid molecule is not attached to the amino acid residue at position 26 of SEQ ID NO:1 or position 28 of SEQ ID NO:2, or a functional variant having at least 75% sequence identity to any one of SEQ ID NO:1 and SEQ ID NO:2,
for use in a method of inhibiting or reducing one or more of i) GIP-induced glucagon secretion, ii) GIP-induced insulin secretion, iii) GIP-induced somatostatin secretion, iv) GIP-induced glucose uptake, v) GIP-induced fatty acid synthesis and/or fatty acid incorporation, vi) high or increased expression or activity of a GIPR, vii) post-prandial GIP release, viii) serum levels of free fatty acids and/or triglycerides, ix) GIP-induced reduction of bone resorption.

In another embodiment there is provided a glucose-dependent insulinotropic peptide (GIP) analogue of formula 1 (hGIP5-30, SEQ ID NO:1):

```
1   2   3   4   5   6   7   8   9   10  11  12
T - F - I - S - D - Y - S - I - A - M - D - K -

13  14  15  16  17  18  19  20  21  22  23  24
I - H - Q - Q - D - F - V - N - W - L - L - A -

25  26
Q - K
``` wherein said peptide optionally further comprises the dipeptide E-G at the N-terminus (hGIP3-30, SEQ ID NO:2), or a functional variant having at least 75% sequence identity to any one of SEQ ID NO:1 and SEQ ID NO:2,
wherein said peptide is modified by attaching at least one fatty acid molecule at one or more amino acid residues of any one of SEQ ID NO:1 and SEQ ID NO:2, or a functional variant having at least 75% sequence identity to any one of SEQ ID NO:1 and SEQ ID NO:2,
with the proviso that said at least one fatty acid molecule is not attached to the amino acid residue at position 26 of SEQ ID NO:1 or position 28 of SEQ ID NO:2, or a functional variant having at least 75% sequence identity to any one of SEQ ID NO:1 and SEQ ID NO:2,
for use in a method of treating a condition selected from the group consisting of metabolic syndrome, obesity, overweight, an obesity-related disorder, pre-diabetes (impaired fasting glucose), diabetes mellitus (type I and type 2), a diabetes-related disorder, insulin resistance, elevated fasting glucose (hyperglycemia), elevated fasting serum triglyceride level (VLDL triglyceride), low high-density lipoprotein (HDL) levels, a fatty acid metabolism disorder, a cardiovascular disease, elevated blood pressure and atherosclerosis.

In one particular embodiment there is provided a peptide as defined herein for use in a method of treating obesity.

In one particular embodiment there is provided a peptide as defined herein for use in a method of treating diabetes mellitus, including diabetes mellitus type I and type II.

In one particular embodiment there is provided a peptide as defined herein for use in a method of treating insulin resistance.

In another embodiment there is provided a glucose-dependent insulinotropic peptide (GIP) analogue of formula 1 (hGIP5-30, SEQ ID NO:1):

```
1   2   3   4   5   6   7   8   9   10  11  12
T - F - I - S - D - Y - S - I - A - M - D - K -

13  14  15  16  17  18  19  20  21  22  23  24
I - H - Q - Q - D - F - V - N - W - L - L - A -

25  26
Q - K
``` wherein said peptide optionally further comprises the dipeptide E-G at the N-terminus (hGIP3-30, SEQ ID NO:2), or a functional variant having at least 75% sequence identity to any one of SEQ ID NO:1 and SEQ ID NO:2,
wherein said peptide is modified by attaching at least one fatty acid molecule at one or more amino acid residues of any one of SEQ ID NO:1 and SEQ ID NO:2, or a functional variant having at least 75% sequence identity to any one of SEQ ID NO:1 and SEQ ID NO:2,
with the proviso that said at least one fatty acid molecule is not attached to the amino acid residue at position 26 of SEQ ID NO:1 or position 28 of SEQ ID NO:2, or a functional variant having at least 75% sequence identity to any one of SEQ ID NO:1 and SEQ ID NO:2,
for use in a method of inducing weight-loss.

It is a further aspect to provide a peptide as defined herein for use in a method of treating cancer.

In one embodiment the cancer is selected from the group consisting of colon cancer, a neuroendocrine cancer and adrenal adenoma.

It is a further aspect to provide a peptide as defined herein for use in a method of treating a bone density disorder (or a bone volume disorder).

In one embodiment there is provided a peptide as defined herein for use in a method of inhibiting activity of bone cells.

In one embodiment there is provided a peptide as defined herein for use in a method of inhibiting (or antagonizing) GIP-induced postprandial reduction in bone resorption. In one embodiment there is provided a peptide as defined herein for use in a method of treating bone cancer.

In one embodiment, the bone density (or volume) disorder is selected from the group consisting of osteoporosis, disorders characterized by low bone density and/or reduced bone volume, disorders characterized by high bone density and/or increased bone volume and osteoporosis.

It is a further aspect to provide a GIP peptide analogue as defined herein for use in a method of characterizing or examining aspects of a disorder, and/or characterizing or examining aspects of the human physiology associated with a disorder, wherein said disorder in one embodiment is selected from metabolic disorder or syndrome, such as obesity, diabetes mellitus, insulin resistance or fatty acid metabolism disorder. In other aspects the invention relates to methods of treating cancer, such as colon cancer or adrenal adenoma. In other aspects the invention relates to methods of treating a bone density disorder characterized by high bone density and/or increased bone volume or osteoporosis. In other aspects the invention relates to methods of treating atherosclerosis.

In another embodiment there is provided the use of a glucose-dependent insulinotropic peptide (GIP) analogue of formula 1 (hGIP5-30, SEQ ID NO:1):

```
1    2    3    4    5    6    7    8    9   10   11   12
T  - F  - I  - S  - D  - Y  - S  - I  - A  - M  - D  - K  -

13   14   15   16   17   18   19   20   21   22   23   24
I  - H  - Q  - Q  - D  - F  - V  - N  - W  - L  - L  - A  -

25   26
Q  - K
``` wherein said peptide optionally further comprises the dipeptide E-G at the N-terminus (hGIP3-30, SEQ ID NO:2),
or a functional variant having at least 75% sequence identity to any one of SEQ ID NO:1 and SEQ ID NO:2,
wherein said peptide is modified by attaching at least one fatty acid molecule at one or more amino acid residues of any one of SEQ ID NO:1 and SEQ ID NO:2, or a functional variant having at least 75% sequence identity to any one of SEQ ID NO:1 and SEQ ID NO:2,
with the proviso that said at least one fatty acid molecule is not attached to the amino acid residue at position 26 of SEQ ID NO:1 or position 28 of SEQ ID NO:2, or a functional variant having at least 75% sequence identity to any one of SEQ ID NO:1 and SEQ ID NO:2,
in the manufacture of a medicament for
  treating a condition selected from the group consisting of metabolic syndrome, obesity, over-weight, an obesity-related disorder, pre-diabetes (impaired fasting glucose), diabetes mellitus (type I and type 2), a diabetes-related disorder, insulin resistance, elevated fasting glucose (hyperglycemia), elevated fasting serum triglyceride level (VLDL triglyceride), low high-density lipoprotein (HDL) levels, a fatty acid metabolism disorder, a cardiovascular disease, elevated blood pressure and atherosclerosis, or
  inducing weight-loss, or
  treating cancer, including but not limited to colon cancer, a neuroendocrine cancer and adrenal adenoma, or
  treating a bone density disorder, including but not limited to osteoporosis, disorders characterized by low bone density and/or reduced bone volume, disorders characterized by high bone density and/or increased bone volume and osteoporosis.

Also provided is a method for treating metabolic syndrome such as obesity, over-weight, diabetes mellitus, insulin resistance or fatty acid metabolism disorder; a cancer such as colon cancer or adrenal adenoma; a bone density disorder, such as bone density disorders characterized by high bone density and/or increased bone volume; or atherosclerosis; said method comprising the step of administering to an individual in need thereof an effective amount of a peptide as defined herein.

An individual in need as referred to herein, is an individual that may benefit from the administration of a peptide or pharmaceutical composition according to the present disclosure. Such an individual may suffer from a metabolic disorder such as obesity, over-weight, diabetes, insulin resistance or fatty acid metabolism disorder, a cancer such as colon cancer or adrenal adenoma, a bone density disorder, or be in risk of suffering therefrom. The individual may be any human being, male or female, infant, middle-aged or old. The disorder to be treated or prevented in the individual may relate to the age of the individual, the general health of the individual, the medications used for treating the individual and whether or not the individual has a prior history of suffering from diseases or disorders that may have or have induced a metabolic disorder such as obesity, over-weight, diabetes, insulin resistance or fatty acid metabolism disorder, a cancer such as colon cancer or adrenal adenoma, atherosclerosis, a bone density disorder. In some embodiments, the disorder to be treated is linked to GIP-induced glucagon secretion, GIP-induced insulin secretion, to GIP-induced somatostatin secretion, to GIP-induced glucose uptake, to GIP-induced fatty acid synthesis and/or fatty acid incorporation, to high expression and/or activity of a GIPR, to release of GIP following a meal; wherein the term "high" is to be construed as referring to levels greater than the corresponding levels observed in individuals not in need of treatment.

Method of Preparation (Peptide)

The peptides according to the present disclosure may be prepared by any methods known in the art. Thus, the GIP-derived peptides may be prepared by standard peptide-preparation techniques such as solution synthesis or Merrifield-type solid phase synthesis.

In one embodiment, a peptide as defined herein is a non-naturally occurring peptide; being derived from naturally occurring protein native GIP, such as GIP1-42.

In one embodiment a peptide according to the present disclosure is purified from a naturally occurring source thereof, such as serum. Protein purification is a series of processes intended to isolate a single type of protein from a complex mixture. The starting material is usually a biological tissue. The various steps in the purification process may free the protein from a matrix that confines it, separate the protein and non-protein parts of the mixture, and finally separate the desired protein from all other proteins. Separation steps may exploit differences in (for example) protein size, physico-chemical properties, binding affinity and biological activity.

In one embodiment a peptide according to the disclosure is synthetically made or produced.

The methods for synthetic production of peptides are well known in the art. Detailed descriptions as well as practical advice for producing synthetic peptides may be found in Synthetic Peptides: A Users Guide (Advances in Molecular Biology), Grant G. A. ed., Oxford University Press, 2002, or in: Pharmaceutical Formulation: Development of Peptides and Proteins, Frokjaer and Hovgaard eds., Taylor and Francis, 1999.

In one embodiment the peptide or peptide sequences of the invention are produced synthetically, in particular, by the Sequence Assisted Peptide Synthesis (SAPS) method, by solution synthesis, by Solid-phase peptide synthesis (SPPS) such as Merrifield-type solid phase synthesis, by recombinant techniques (production by host cells comprising a first nucleic acid sequence encoding the peptide operably associated with a second nucleic acid capable of directing expression in said host cells) or enzymatic synthesis. These are well-known to the skilled person.

Peptides may be synthesised either batch-wise on a fully automated peptide synthesiser using 9-fluorenylmethyloxycarbonyl (Fmoc) or tert-Butyloxycarbonyl (Boc) as N-a-amino protecting group and suitable common protection groups for side-chain functionalities.

After purification such as by reversed phase HPLC, peptides may be further processed to obtain for example cyclic or C- or N-terminal modified isoforms. The methods for cyclization and terminal modification are well-known in the art.

Peptides according to the invention may be synthesized as monomers or multimers such as dimers or tetramers.

Pharmaceutical Composition and Formulation

Whilst it is possible for the bioactive agent of the present disclosure to be administered as the raw chemical (peptide), it is sometimes preferred to present them in the form of a pharmaceutical formulation. Such a pharmaceutical formulation may be referred to as a pharmaceutical composition, pharmaceutically acceptable composition or pharmaceutically safe composition.

Accordingly, further provided is a pharmaceutical formulation, which comprises a bioactive agent of the present invention, or a pharmaceutically acceptable salt or ester thereof, and a pharmaceutically acceptable carrier, excipient and/or diluent. The pharmaceutical formulations may be prepared by conventional techniques, e.g. as described in Remington: The Science and Practice of Pharmacy 2005, Lippincott, Williams & Wilkins.

Pharmaceutically acceptable salts of the instant peptide compounds, where they can be prepared, are also intended to be covered by this invention. These salts will be ones which are acceptable in their application to a pharmaceutical use. By that it is meant that the salt will retain the biological activity of the parent compound and the salt will not have untoward or deleterious effects in its application and use in treating diseases.

Pharmaceutically acceptable salts are prepared in a standard manner. If the parent compound is a base it is treated with an excess of an organic or inorganic acid in a suitable solvent. If the parent compound is an acid, it is treated with an inorganic or organic base in a suitable solvent.

The peptide compounds as disclosed herein may be administered in the form of an alkali metal or earth alkali metal salt thereof, concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount.

Examples of pharmaceutically acceptable acid addition salts for use in the present inventive pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic acids, and arylsulphonic, for example.

In a particular embodiment, the peptide according to the disclosure is formulated as an acetate salt or TFA (trifluoroacetate) salt.

Administration and Dosage

According to the present disclosure, a peptide, or a composition comprising a peptide as defined herein is administered to individuals in need of treatment in pharmaceutically effective doses or a therapeutically effective amount. The dosage requirements will vary with the particular drug composition employed, the route of administration and the particular subject being treated, which depend on the severity and the sort of the disorder as well as on the weight and general state of the subject. It will also be recognized by one skilled in the art that the optimal quantity and spacing of individual dosages of a peptide compound will be determined by the nature and extent of the condition being treated, the form, route and site of administration, and the particular patient being treated, and that such optima can be determined by conventional techniques. It will also be appreciated by one of skill in the art that the optimal course of treatment, i.e., the number of doses of a compound given per day for a defined number of days, can be ascertained using conventional course of treatment determination tests.

In one embodiment the bioactive agent is administered at least once daily, such as once daily, such as twice daily, such as thrice daily, such as four times daily, such as five times daily.

A dose may also be administered in intermittent intervals, or intervals, whereby a dose is not administered every day. Rather one or more doses may be administered every second day, every third day, every fourth day, every fifth day, every sixth day, every week, every second week, every third week, every fourth week, every fifth week, every sixth week, or intervals within those ranges (such as every 2 to 4 weeks, or 4 to 6 weeks).

In one embodiment, the bioactive agent is administered in doses of at least 30000 pmol/kg/day, such as at least 60000 pmol/kg/day, such as at least 72000 pmol/kg/day, such as at least 90000 pmol/kg/day, such as at least 120000 pmol/kg/day, such as at least 150000 pmol/kg/day, such as at least 30000 pmol/kg/day, preferably such as at least 60000 pmol/kg/day. In a particular embodiment, the bioactive agent is administered at a dosage of 72000 pmol/kg/day.

In one embodiment, the bioactive agent is administered at a daily dosage of 30000 pmol/kg to 40000 pmol/kg, such as 40000 pmol/kg to 50000 pmol/kg, such as 50000 pmol/kg to 60000 pmol/kg, such as 60000 pmol/kg to 70000 pmol/kg, such as 70000 pmol/kg to 80000 pmol/kg, such as 80000 pmol/kg to 90000 pmol/kg, such as 90000 pmol/kg to 100000 pmol/kg, such as 100000 pmol/kg to 110000 pmol/kg, such as 110000 pmol/kg to 120000 pmol/kg. In a particular embodiment, the bioactive agent is a peptide and is administered at a daily dose of 60000 pmol/kg or 72000 pmol/kg.

In one embodiment the bioactive agent is administered by infusion. In one embodiment, the bioactive agent is a peptide, and the infusion takes place over a duration of at least 15 min, such as at least 20 min, such as at least 30 min, such as at least 40 min, such as at least 50 min, such as at least 60 min, such as at least 90 min, such as at least 120 min, preferably such as 60 min.

In one embodiment the bioactive agent is administered over a duration between 15 and 120 min, such as between 15 and 20 min, such as between 20 and 30 min, such as between 30 and 40 min, such as between 40 and 50 min, such as between 50 and 60 min, such as between 60 and 90 min, such as between 90 and 120 min.

In one embodiment the bioactive agent is administered once daily over a duration of 60 min, or twice daily over a duration of 30 min, or thrice daily over a duration of 20 min, or four times daily over a duration of 15 min, or five times daily over a duration of 12 min, where the duration is the duration of each individual administration.

In one embodiment the bioactive agent is administered at a dosage of at least 500 pmol/kg/min, such as at least 1000 pmol/kg/min, such as at least 1200 pmol/kg/min, such as at least 1500 pmol/kg/min, such as at least 2000 pmol/kg/min, such as at least 2500 pmol/kg/min, such as at least 5000 pmol/kg/min.

The skilled person knows that if the number of daily administrations is increased, the dose to be administered in each administration may be decreased accordingly. Likewise, if the duration of each administration is decreased, the dosage may be increased accordingly.

The bioactive agent to be administered is a peptide according to the present disclosure. In preferred embodiments, the peptide is SEQ ID NO:1 or SEQ ID NO:2, or a functional variant having at least 75% sequence identity to any one of SEQ ID NO:1 and SEQ ID NO:2, wherein said peptide is modified by attaching at least one fatty acid molecule at one or more amino acid residues of any one of SEQ ID NO:1 and SEQ ID NO:2, or a functional variant thereof, with the proviso that said at least one fatty acid molecule is not attached to the amino acid residue at position 26 of SEQ ID NO:1 or position 28 of SEQ ID NO:2.

In one embodiment the bioactive agent is administered with one or more additional active ingredients. These other ingredients may be pharmaceutically active. In some embodiments, the bioactive agent is a peptide as defined above and the other ingredient is hGIP1-42 or a variant thereof.

Routes of Administration

It will be appreciated that the preferred route of administration will depend on the general condition and age of the subject to be treated, the nature of the condition to be treated, the location of the tissue to be treated in the body and the active ingredient chosen.

Systemic Treatment

For systemic treatment according to the present disclosure the route of administration is capable of introducing the bioactive agent into the blood stream to ultimately target the sites of desired action.

Such routes of administration are any suitable routes, such as an enteral route (including the oral, rectal, nasal, pulmonary, buccal, sublingual, transdermal, intracisternal and intraperitoneal administration), and/or a parenteral route (including subcutaneous, intramuscular, intrathecal, intracerebral, intravenous and intradermal administration).

Parenteral Administration

Parenteral administration is any administration route not being the oral/enteral route whereby the medicament avoids first-pass degradation in the liver. Accordingly, parenteral administration includes any injections and infusions, for example bolus injection or continuous infusion, such as intravenous administration, intramuscular administration or subcutaneous administration. Furthermore, parenteral administration includes inhalations and topical administration.

Accordingly, the bioactive agent may be administered topically to cross any mucosal membrane of an animal to which the biologically active substance is to be given, e.g. in the nose, vagina, eye, mouth, genital tract, lungs, gastro-intestinal tract, or rectum, preferably the mucosa of the nose, or mouth, and accordingly, parenteral administration may also include buccal, sublingual, nasal, rectal, vaginal and intraperitoneal administration as well as pulmonal and bronchial administration by inhalation or installation. Also, the agent may be administered topically to cross the skin.

Local Treatment

The bioactive agent according to the invention may in one embodiment be used as a local treatment, i.e. be introduced directly to the site(s) of action. Accordingly, the bioactive agent may be applied to the skin or mucosa directly, or the bioactive agent may be injected into the site of action, for example into the diseased tissue or to an end artery leading directly to the diseased tissue. These administration forms preferably avoid the blood brain barrier.

Kit-of-Parts

The present disclosure also relates to a kit-of-parts comprising one or more of the bioactive agents described above and at least one additional or further component, such as one or more second active ingredients.

REFERENCES

1. Baggio L L, Drucker D J. Biology of Incretins: GLP-1 and GIP. Gastroenterology 2007; 132(6):2131-2157.
2. Hoist J J. On the Physiology of GIP and GLP-1. Horm Metab Res 2004; 36(11/12):747-754.
3. Heer J, Rasmussen C, Coy D H, Hoist J J. Glucagon-like peptide-1, but not glucose-dependent insulinotropic peptide, inhibits glucagon secretion via somatostatin (receptor subtype 2) in the perfused rat pancreas. Diabetologia 2008; 51(12):2263-2270.
4. Gutniak M, +ÿrkov C, Hoist J J, Ahr+®n B, Efendi-ç S. Antidiabetogenic Effect of Glucagon-like Peptide-1 (7GÇô36)amide in Normal Subjects and Patients with Diabetes Mellitus. N Engl J Med 1992; 326(20):1316-1322.
5. Christensen M, Vedtofte L, Hoist J J, Vilsboell T, Knop F K. Glucose-Dependent Insulinotropic Polypeptide: A Bifunctional Glucose-Dependent Regulator of Glucagon and Insulin Secretion in Humans. Diabetes 2011; 60(12): 3103-3109.
6. Pederson R, Brown J. Interaction of Gastric Inhibitory Polypeptide, Glucose, and Arginine on Insulin and Glucagon Secretion from the Perfused Rat Pancreas. Endocrinology 1978; 103(2):610-615.
7. Adrian T E, Bloom S R, Hermansen K, Iversen J. Pancreatic polypeptide, glucagon and insulin secretion from the isolated perfused canine pancreas. Diabetologia 1978; 14(6):413-417.
8. Brunicardi F C, Druck P, Seymour N E, Sun Y S, Elahi D, Andersen D K. Selective neurohormonal interactions in islet cell secretion in the isolated perfused human pancreas. Journal of Surgical Research 1990; 48(4):273-278.
9. Dupre J, Caussignac Y, McDonald T J, Van Vliet S. Stimulation of Glucagon Secretion by Gastric Inhibitory Polypeptide in Patients with Hepatic Cirrhosis and Hyperglucagonemia. The Journal of Clinical Endocrinology & Metabolism 1991; 72(1):125-129.
10. Ding W G, Renstrom E, Rorsman P, Buschard K, Gromada J. Glucagon-like peptide I and glucose-dependent insulinotropic polypeptide stimulate Ca2+-induced secretion in rat alpha-cells by a protein kinase A-mediated mechanism. Diabetes 1997; 46(5):792-800.
11. Meier J J, Gallwitz B, Siepmann N et al. Gastric inhibitory polypeptide (GIP) dose-dependently stimulates glucagon secretion in healthy human subjects at euglycaemia. Diabetologia 2003; 46(6):798-801.

12. Christensen M B, Calanna S, Hoist J J, Vilsboell T, Knop F K. Glucose-dependent Insulinotropic Polypeptide: Blood Glucose Stabilizing Effects in Patients With Type 2 Diabetes. The Journal of Clinical Endocrinology & Metabolism 2013; 99(3):E418-E426.
13. Christensen M, Calanna S, Sparre-Ulrich A H et al. Glucose-Dependent Insulinotropic Polypeptide Augments Glucagon Responses to Hypoglycemia in Type 1 Diabetes. Diabetes 2014.
14. Song D H, GettyGÇôKaushik L, Tseng E, Simon J, Corkey B E, Wolfe M M. Glucose-Dependent Insulinotropic Polypeptide Enhances Adipocyte Development and Glucose Uptake in Part Through Akt Activation. Gastroenterology 2007; 133(6):1796-1805.
15. Miyawaki K, Yamada Y, Ban N et al. Inhibition of gastric inhibitory polypeptide signaling prevents obesity. Nat Med 2002; 8(7):738-742.
16. Stanch G H, Bar R S, Mazzaferri E L. GIP increases insulin receptor affinity and cellular sensitivity in adipocytes. Am J Physiol 1985; 249(6 Pt 1):E603-E607.
17. Getty-Kaushik L, Song D H, Boylan M O, Corkey B E, Wolfe M M. Glucose-Dependent Insulinotropic Polypeptide Modulates Adipocyte Lipolysis and Reesterification. Obesity 2006; 14(7):1124-1131.
18. Hauner H, Glatting G, Kaminska D, Pfeiffer E F. Effects of gastric inhibitory polypeptide on glucose and lipid metabolism of isolated rat adipocytes. Ann Nutr Metab 1988; 32(5-6):282-288.
19. Kim S J, Nian C, Karunakaran S, Clee S M, Isales C M, McIntosh C H S. GIP-Overexpressing Mice Demonstrate Reduced Diet-Induced Obesity and Steatosis, and Improved Glucose Homeostasis. PLoS ONE 2012; 7(7): e40156.
20. Nasteska D, Harada N, Suzuki K et al. Chronic Reduction of GIP Secretion Alleviates Obesity and Insulin Resistance Under High-Fat Diet Conditions. Diabetes 2014; 63(7):2332-2343.
21. Miyawaki K, Yamada Y, Yano H et al. Glucose intolerance caused by a defect in the entero-insular axis: A study in gastric inhibitory polypeptide receptor knockout mice. Proceedings of the National Academy of Sciences 1999; 96(26):14843-14847.
22. Ahlqvist E, Osmark P, Kuulasmaa T et al. Link Between GIP and Osteopontin in Adipose Tissue and Insulin Resistance. Diabetes 2013; 62(6):2088-2094.
23. Calanna S, Christensen M, Hoist J J et al. Secretion of Glucose-Dependent Insulinotropic Polypeptide in Patients With Type 2 Diabetes: Systematic review and meta-analysis of clinical studies. Diabetes Care 2013; 36(10):3346-3352.
24. Asmar M, Simonsen L, Madsbad S, Stallknecht B, Hoist J J, B++low J. Glucose-Dependent Insulinotropic Polypeptide May Enhance Fatty Acid Re-esterification in Subcutaneous Abdominal Adipose Tissue in Lean Humans. Diabetes 2010; 59(9):2160-2163.
25. Deschamps I, Heptner W, Desjeux J F, Baltakse V, Machinot S, Lestradet H. Effects of diet on insulin and gastric inhibitory polypeptide levels in obese children. Pediatr Res 1980; 14(4 Pt 1):300-303.
26. Brøns C, Jensen C B, Storgaard H et al. Impact of short-term high-fat feeding on glucose and insulin metabolism in young healthy men. The Journal of Physiology 2009; 587(10):2387-2397.
27. Raufman J P, Singh L, Eng J. Exendin-3, a novel peptide from Heloderma horridum venom, interacts with vasoactive intestinal peptide receptors and a newly described receptor on dispersed acini from guinea pig pancreas. Description of exendin-3(9-39) amide, a specific exendin receptor antagonist. Journal of Biological Chemistry 1991; 266(5):2897-2902.
28. Jorgensen N B, Dirksen C, Bojsen-Møller K N et al. Exaggerated Glucagon-Like Peptide 1 Response Is Important for Improved+|-Cell Function and Glucose Tolerance After Roux-en-Y Gastric Bypass in Patients With Type 2 Diabetes. Diabetes 2013; 62(9):3044-3052.
29. Nakamura T, Tanimoto H, Mizuno Y, Tsubamoto Y, Noda H. Biological and functional characteristics of a novel lowGÇômolecular weight antagonist of glucose-dependent insulinotropic polypeptide receptor, SKL-14959, in vitro and in vivo. Diabetes, Obesity and Metabolism 2012; 14(6):511-517.
30. Ebert R, Illmer K, Creutzfeldt W. Release of gastric inhibitory polypeptide (GIP) by intraduodenal acidification in rats and humans and abolishment of the incretin effect of acid by GIP-antiserum in rats. Gastroenterology 1979; 76(3):515-523.
31. Fulurija A, Lutz T A, Sladko K et al. Vaccination against GIP for the Treatment of Obesity. PLoS ONE 2008; 3(9):e3163.
32. Irwin N, McClean P L, Patterson S, Hunter K, Flatt P R. Active immunisation against gastric inhibitory polypeptide (GIP) improves blood glucose control in an animal model of obesity-diabetes. Biological Chemistry. bchm 390, 75. 2009. 16-7-2014.
33. Hinke S A, Manhart S, Pamir N et al. Identification of a bioactive domain in the amino-terminus of glucose-dependent insulinotropic polypeptide (GIP). Biochimica et Biophysica Acta (BBA)—Protein Structure and Molecular Enzymology 2001; 1547(1):143-155.
34. Tseng C C, Kieffer T J, Jarboe L A, Usdin T B, Wolfe M M. Postprandial stimulation of insulin release by glucose-dependent insulinotropic polypeptide (GIP). Effect of a specific glucose-dependent insulinotropic polypeptide receptor antagonist in the rat. J Clin Invest 1996; 98(11): 2440-2445.
35. Irwin N, Green B D, Parker J C, Gault V A, O'Harte F P M, Flatt P R. Biological activity and antidiabetic potential of synthetic fragment peptides of glucose-dependent insulinotropic polypeptide, GIP(1-16) and (Pro3)GIP(1-16). Regulatory Peptides 2006; 135(1GÇô2):45-53.
36. Kerr B D, Flatt A J S, Flatt P R, Gault V A. Characterization and biological actions of N-terminal truncated forms of glucose-dependent insulinotropic polypeptide. Biochemical and Biophysical Research Communications 2011; 404(3):870-876.
37. Gelling R W, Coy D H, Pederson R A et al. GIP(6-30 amide) contains the high affinity binding region of GIP and is a potent inhibitor of GIP1-42 action in vitro. Regulatory Peptides 1997; 69(3):151-154.
38. Deacon C F P. GIP-(3-42) does not antagonize insulinotropic effects of GIP at physiological concentrations. American Journal of Physiology—Endocrinology and Metabolism 2006; 291(3):E468-E475.
39. Gault V A, O'Harte F P M, Harriott P, Flatt P R. Characterization of the Cellular and Metabolic Effects of a Novel Enzyme-Resistant Antagonist of Glucose-Dependent Insulinotropic Polypeptide. Biochemical and Biophysical Research Communications 2002; 290(5):1420-1426.
40. Ravn P, Madhurantakam C, Kunze S et al. Structural and Pharmacological Characterization of Novel Potent and Selective Monoclonal Antibody Antagonists of Glucose-dependent Insulinotropic Polypeptide Receptor. Journal of Biological Chemistry 2013; 288(27):19760-19772.

41. Deacon C F, Plamboeck A, Rosenkilde M M, de Heer J, Hoist J J. GIP-(3-42) does not antagonize insulinotropic effects of GIP at physiological concentrations. American Journal of Physiology—Endocrinology and Metabolism 2006; 291(3):E468-E475.

42. Goetze J P, Hunter I, Lippert S K, Bardram L, Rehfeld J F. Processing-independent analysis of peptide hormones and prohormones in plasma. Front Biosci 2012; 17:1804-1815.

43. Goetze J P, Rehfeld J F. Peptide hormones and their prohormones as biomarkers. Biomarkers Med 2009; 3(4): 335-338.

44. Fujita Y, Asadi A, Yang G K, Kwok Y N, Kieffer T J. Differential processing of pro-glucose-dependent insulinotropic polypeptide in gut. American Journal of Physiology—Gastrointestinal and Liver Physiology 2010; 298 (5):G608-G614.

45. Widenmaier S B, Kim S J, Yang G K et al. A GIP Receptor Agonist Exhibits beta-Cell Anti-Apoptotic Actions in Rat Models of Diabetes Resulting in Improved beta-Cell Function and Glycemic Control. PLoS ONE 2010; 5(3):e9590.

46. Graham F L, van der Eb A J. A new technique for the assay of infectivity of human adenovirus 5 DNA. Virology 1973; 52(2):456-467.

47. Kissow H, Hartmann B, Hoist J J et al. Glucagon-like peptide-1 (GLP-1) receptor agonism or DPP-4 inhibition does not accelerate neoplasia in carcinogen treated mice. Regulatory Peptides 2012; 179(1GÇô3):91-100.

48. Hoejberg P V, Vilsboell T, Raboel R et al. Four weeks of near-normalisation of blood glucose improves the insulin response to glucagon-like peptide-1 and glucose-dependent insulinotropic polypeptide in patients with type 2 diabetes. Diabetologia 2009; 52(2):199-207.

DEBLASI, A., O'REILLY, K. & MOTULSKY, H. J. 1989. Calculating receptor number from binding experiments using same compound as radioligand and competitor. Trends in Pharmacological Sciences, 10, 227-229.

LAZARENO, S. & BIRDSALL, N. J. 1993. Estimation of competitive antagonist affinity from functional inhibition curves using the Gaddum, Schild and Cheng-Prusoff equations. Br J Pharmacol, 109, 1110-9.

ROSENKILDE, M. M., CAHIR, M., GETHER, U., HJORTH, S. A. & SCHWARTZ, T. W. 1994. Mutations along transmembrane segment II of the NK-1 receptor affect substance P competition with non-peptide antagonists but not substance P binding. J Biol Chem, 269, 28160-4.

HOLST, J. J. & BERSANI, M. 1991. 1—Assays for Peptide Products of Somatostatin Gene Expression. In: CONN, P. M. (ed.) Methods in Neurosciences. Academic Press.

PATHAK, V., GAULT, V. A., FLATT, P. R. & IRWIN, N. 2015. Antagonism of gastric inhibitory polypeptide (GIP) by palmitoylation of GIP analogues with N- and C-terminal modifications improves obesity and metabolic control in high fat fed mice. Mol Cell Endocrinol, 401, 120-9.

HANSEN L S, SPARRE-ULRICH A H, CHRISTENSEN M, KNOP F K, HARTMANN B, HOLST J J & ROSENKILDE M. N-terminally and C-terminally truncated forms of glucose-dependent insulinotropic polypeptide are high-affinity competitive antagonists of the human GIP receptor.British Journal of Pharmacology (2016) 173, 826-838.

EXAMPLES

The present examples support the following conclusions:
1) Antagonistic properties of human GIP(3-30)NH$_2$ are preserved following lipidation (fatty acyl) in the midregion but not at position 3 and position 30
2) Antagonistic properties of human GIP(5-30)NH$_2$ are preserved following lipidation (fatty acyl) at the N-terminus (position 5) and mid-region but not at position 30
3) Several acylation sites show great potential on both GIP(3-30)NH$_2$ and GIP(5-30)NH$_2$
4) Addition of linkers (molecules linking the fatty acids to the peptides) may improve the antagonistic profile
5) Lipidation increases albumin binding of GIP analogues
6) Lipidation increases the elimination half-life of GIP analogues Materials and Methods The generation and action of GIP(3-30) and GIP(5-30) peptides per se is disclosed in WO 2016/034186.

Materials

Human GIP(1-42) was purchased from Bachem, Bubendorf, Switzerland (H5645) while the remaining ligands were synthesized by Caslo™, Lyngby, Denmark and Almac Group, Craigavon, United Kingdom. cDNA of the human GIP receptor was purchased from Origene, Rockville, Md., USA (SC110906) and cloned into a pCMV-Script vector. Iodinated human GIP(1-42) was purchased from PerkinElmer Life Sciences, Skovlunde, Denmark (NEX402025UC).

Animals

LYH/LYD strain pigs or mini-pigs were housed in the animal facility at the Faculty of Health and Medical Sciences.

Transfections and Tissue Culture

COS-7 cells were cultured at 10% $CO_2$ and 37° C. in Dulbecco's modified Eagle's medium 1885 supplemented with 10% fetal bovine serum, 2 mM glutamine, 180 units/ml penicillin, and 45 g/ml streptomycin. Transient transfection of the COS-7 cells for cAMP accumulation and competition binding was performed using the calcium phosphate precipitation method with the addition of chloroquine[46-47].

cAMP Assay

Transient transfected COS-7 cells expressing the human GIP receptor were seeded in white 96-well plates with a density of $3.5*10^4$/well. The day after, the cells were washed twice with Hepes buffered saline (HBS) buffer and incubated with HBS and 1 mM 3-isobutyl-1-methylxanthine (IBMX) for 30 min at 37° C. To test for agonistic properties, ligands were added and incubated for 30 min at 37° C. In order to test for antagonistic properties, the cells were preincubated with the antagonists for 10 min prior to the addition of the agonist and subsequent incubated for 20 additional min. The HitHunter™ cAMP XS assay (DiscoveRx) was carried out according to the manufacturer's instructions.

$^{125}$I-Human GIP Competition Binding Assay

Transient transfected COS-7 cells expressing the human GIP receptor were seeded in clear 96-well plates the day after transfection using a number of cells/well that obtained 5-10% specific binding of the added radioactive ligand. The following day, cells were assayed by competition binding for 3 h at 4° C. using 15-40 pM 125 I-human GIP as well as increasing concentrations unlabeled ligand in 50 mM Hepes buffer (pH 7.2) in the presence and absence of 2% HSA. After incubation, the cells were washed twice in ice-cold binding buffer (+/−2% HSA) and lysed using 200 mM NaOH with 1% SDS for 30 min. Nonspecific binding was determined as the binding of radioactive ligand to untransfected cells.

Elimination Half-Life ($T_{1/2}$) Estimated in Pigs

A pig was subcutaneously administered one of the lipidated GIP(3-30)NH$_2$ analogs (compound AT117) (1-10 nmol/kg, total volume 2-6 mL) after which 10-18 blood samples were collected before and up to 57 hours post subcutaneous administration) from a central venous catheter. The catheter was flushed with saline and heparin between samples. Blood was collected into cold EDTA tubes, centrifuged and plasma was kept at −20° C. pending analyses. When experiments are completed, the animals will be killed.

Hormone Analysis

Concentrations of the lipidated GIP(3-30)NH$_2$ or GIP(5-30)NH$_2$ analogues in blood samples from pigs were analysed by RIA. Analogues' immunoreactivity was determined using antiserum Ab95234, Ab95235, Ab95236, a polyclonal in-house antibody raised in rabbits specific for either the mid region of GIP(1-30)NH$_2$ or amidated C-terminus of GIP(3-30)NH$_2$.

Data Analysis

IC$_{50}$, EC$_{50}$, and K$_i$ values were determined by nonlinear regression. These were carried out with the GraphPad Prism 6.0 software (GraphPad, San Diego, Calif., USA) and Microsoft Excel™. K$_i$ values were based on the formula for one class of binding sites in homologous competition binding studies and the Cheng Prussoffs formula, respectively (DeBlasi et al., 1989). To determine the HSA binding potential, the fold change in affinity (as determined by IC$_{50}$) was calculated as IC$_{50 \, (plus \, HSA)}$/IC$_{50 \, (minus \, HSA)}$.

Example 1—Antagonistic Properties of Human GIP(3-30)NH$_2$ are Preserved Following Lipidation at Selected Amino Acids Positions and for Example in the Midregion but not at Position 3 and Position 30

Figure 1:
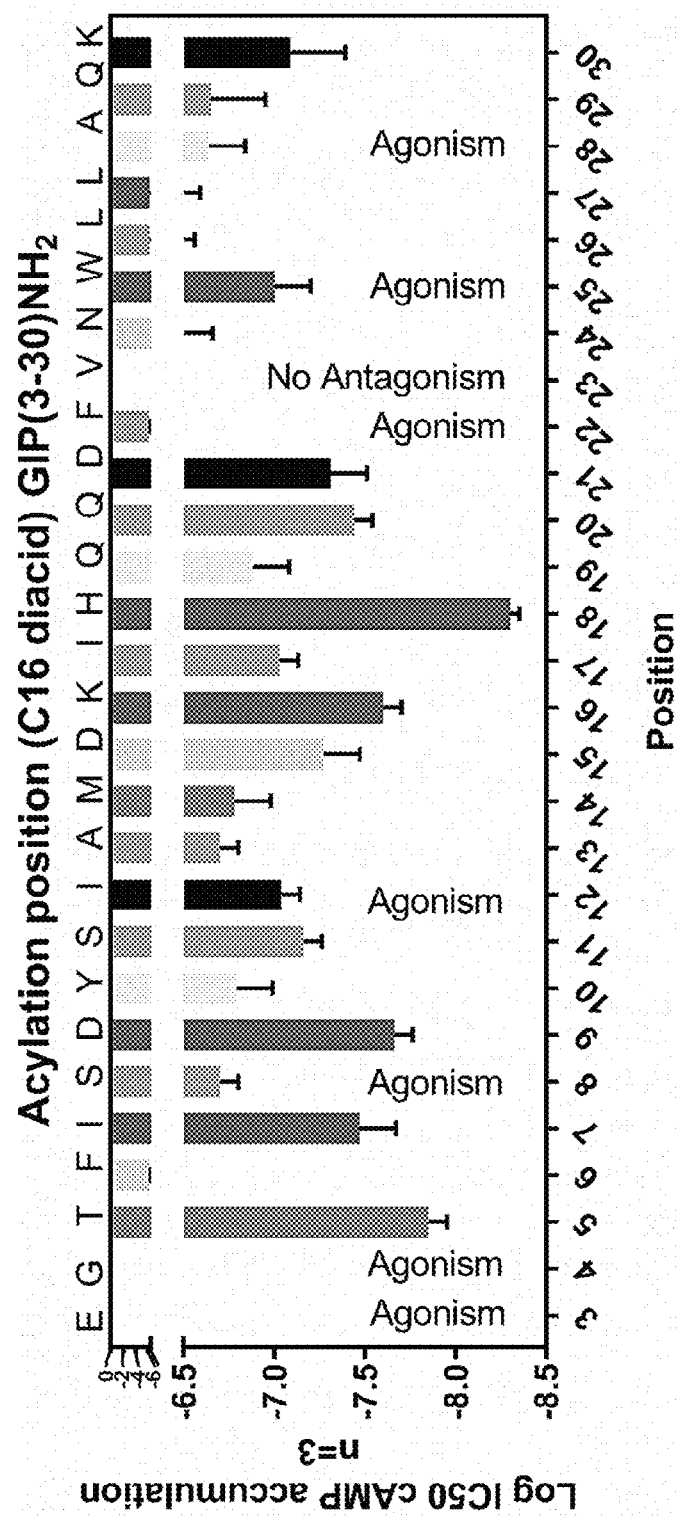
FIG. 1. Lysine (Lys) scan coupled with C16-diacid of GIP(5-30)$NH_2$ from position 5 to position 30 shows highly promising lipidation sites for the development of high potent, long-acting GIP receptor antagonists.

We have previously showed that GIP(3-30)NH$_2$ has a half-life ($T_{1/2}$) of 7.5 min in humans and pigs. In order to develop a long-acting GIP receptor antagonist, GIP(3-30)NH$_2$ was lipidated at different regions with different lengths of fatty acids (C12-C18, C16 diacid). In particular, GIP(3-30)NH$_2$ was either lipidated at the N-terminus, the naturally occurring lysines at position 16 or 30, or the latter amino acids positions which GIP(3-30)NH$_2$ were substituted to lysine prior to lipidation (FIG. 1 and table 1). Both the agonistic and antagonistic profiles of the compounds were tested in cAMP accumulation experiments done in transiently transfected COS-7 cells expressing the human GIP receptor. To investigate if these lipidated analogues still retained their antagonistic properties following lipidation, their ability to inhibit a GIP-mediated cAMP response corresponding to 50-80% of maximum activation was examined. In addition, for selected analogues, we measured their affinities in the absence and presence of 2% human albumin as a proxy estimate for the compounds' ability to bind to human albumin (HSA). Increased ability to bind to HSA would be an estimate for a possibly increased $T_{1/2}$ in vivo since binding to albumin in plasma will decrease the elimination.

TABLE 1

Antagonistic and agonistic properties of human GIP(3-30)NH$_2$ and human GIP(3-50)NH$_2$ peptides, modified and lapidated as described in the table.

| | | cAMP antagonism | | | | cAMP agonism | | | | | |
|---|---|---|---|---|---|---|---|---|---|---|---|
| ID | Formula | log | SEM | nM | n | Emax | SEM | EC50 | SEM | nM | n |
| NA | hGIP(3-30)NH2 | −7.2 | 0.1 | 65 | >3 | | | | | | |
| AT101 | [hGIP(3-30)NH2—C12/3] | 0.0 | 0.0 | 0.0 | 3 | 62 | 8.1 | −9.1 | −0.1 | 0.7 | 3 |
| AT102 | [hGIP(3-30)NH2—C12/16] | 0.0 | 0.0 | 0.0 | 3 | 66 | 10 | −9.1 | −0.1 | 0.7 | 3 |
| AT103 | [hGIP(3-30)NH2—C12/30] | −6.9 | −0.1 | 121 | 3 | 7 | 5.3 | −5.3 | −1.5 | 4883 | 3 |
| AT104 | [hGIP(3-30)NH2—C16/3] | 0.0 | 0.0 | 0.0 | 3 | 81 | 8.6 | −8.6 | −0.1 | 2.4 | 3 |
| AT105 | [hGIP(3-30)NH2—C16/16] | −7.6 | −0.2 | 24 | 3 | 34 | 16 | −5.9 | 0.0 | 1135 | 3 |
| AT106 | [hGIP(3-30)NH2—C16/30] | 0.0 | 0.0 | 0.0 | 3 | 64 | 5.6 | −6.4 | −0.2 | 390 | 3 |
| AT107 | [hGIP(3-30)NH2[T5W; D15E; H18A]-C16/16] | −7.1 | −0.1 | 77 | 3 | 23 | 8.0 | −5.9 | −0.7 | 1303 | 2 |
| AT110 | [hGIP(3-30)NH2—C14/3] | 0.0 | 0.0 | 0.0 | 3 | 64 | 3 | −8.4 | 0.1 | 3.6 | 3 |
| AT111 | [hGIP(3-30)NH2—C14/16] | −7.6 | 0.3 | 22 | 2 | 0 | 0.0 | 0.0 | 0.0 | 0.0 | 3 |
| AT112 | [hGIP(3-30)NH2—C14/30] | 0.0 | 0.0 | 0 | 3 | 29 | 2.5 | −5.4 | −1.3 | 3954 | 3 |
| AT113 | [hGIP(3-30)NH2—C18/3] | 0.0 | 0.0 | 0.0 | 3 | 77 | 4.3 | −8.0 | −0.3 | 9.9 | 3 |
| AT114 | [hGIP(3-30)NH2—C18/16] | −7.2 | 0.4 | 46 | 3 | 39 | 15 | −5.5 | −0.1 | 2958 | 3 |
| AT115 | [hGIP(3-30)NH2—C18/30] | 0.0 | 0.0 | 0.0 | 3 | na | na | −6.9 | na | 134 | 3 |
| AT116 | [hGIP(3-30)NH2—C12/18] | −7.9 | −0.2 | 12 | 3 | 0 | 0.0 | 0.0 | 0.0 | 0.0 | 3 |
| AT117 | [hGIP(3-30)NH2[H18K]-C16/18] | −7.8 | −0.2 | 15 | 3 | 0 | 0.0 | 0.0 | 0.0 | 0.0 | 3 |
| AT130 | [hGIP(3-30)NH2[D15E; H18A]-C12/30] | 0.0 | 0.0 | 0.0 | 3 | 49 | 8.6 | −5.1 | −0.3 | 8690 | 3 |
| AT131 | [hGIP(3-30)NH2[D15E; H18A]-C16/16] | −7.4 | 0.5 | 65 | 3 | 35 | 9.0 | −4.9 | −0.8 | 11767 | 3 |
| AT143 | [hGIP(3-30)NH2[M14L; H18K]-C16/18] | −7.8 | 0.2 | 15.1 | 3 | 40 | 1.9 | −6.3 | 0.1 | 521.2 | 3 |
| AT144 | [hGIP(3-30)NH2[K16R; H18K; K30R]-C16/18] | −7.3 | 0.2 | 53.3 | 3 | 0 | 0.0 | 0.0 | 0.0 | 0.0 | 3 |
| AT146 | [hGIP(3-30)NH2[M14L]-C12/3] | na | na | na | | na | na | na | | | |
| AT147 | [hGIP(3-30)NH2[M14L; H18R; K30R]-C12/3] | na | na | na | | na | na | na | | | |
| AT148 | [hGIP(3-30)NH2—C12/3] | 0 | 0.0 | 0.0 | 3 | 43 | 4.9 | −7.9 | 0.3 | 13 | 3 |
| AT149 | [hGIP(3-30)NH2[H18R; K30R]-C12diacid/3] | 0 | 0.0 | 0.0 | 3 | 50 | 9.1 | −7.6 | 0.5 | 24 | 3 |
| AT150 | [hGIP(3-30)NH2[H18R; K30R]-C16/3] | na | na | na | | na | na | na | | | |
| AT153 | [hGIP(3-30)NH2[H18R; K30R]-C12/16] | −6.7 | 0.3 | 187 | 3 | 0 | 0.0 | 0.0 | 0.0 | 0.0 | 3 |
| AT154 | [hGIP(3-30)NH2—C12/16] | −7.2 | 0.3 | 63 | 3 | 0 | 0.0 | 0.0 | 0.0 | 0.0 | 3 |
| AT155 | [hGIP(3-30)NH2[H18R; K30R]-C12diacid/16] | na | na | na | | na | na | na | | | |

TABLE 1-continued

Antagonistic and agonistic properties of human GIP(3-30)NH₂ and human GIP(3-50)NH₂ peptides, modified and lapidated as described in the table.

| ID | Formula | cAMP antagonism | | | | cAMP agonism | | | | | |
|---|---|---|---|---|---|---|---|---|---|---|---|
| | | log | SEM | nM | n | Emax | SEM | EC50 | SEM | nM | n |
| AT158 | [hGIP(3-30)NH2[H18K]-C16diacid/18] | −8.3 | 0.0 | 5 | 3 | 6 | 0.5 | −8.5 | 0.3 | 3.1 | 3 |
| AT159 | [hGIP(3-30)NH2[K16R; H18K; K30R]-C16diacid/18] | −8.2 | 0.0 | 6 | 3 | 6 | 1.1 | −8.7 | 0.7 | 2.0 | 3 |
| AT160 | [hGIP(3-30)NH2[H18K]-C18/18] | −7.4 | 0.2 | 38 | 3 | 13 | 5.8 | −6.0 | 0.4 | 962 | 3 |
| AT162 | [hGIP(3-30)NH2[H18R; K30R]-C18/16] | −7.6 | 0.3 | 27 | 3 | 44 | 3.7 | −5.9 | 0.1 | 1374 | 3 |
| AT163 | [hGIP(3-30)NH2[H18K]-C16/16] | −6.7 | 0.2 | 212 | 3 | 0 | 0.0 | 0.0 | 0.0 | 0.0 | 2 |
| AT294 | [hGIP(3-30)NH2[E3K]-C16diacid/3] | −8.6 | 0.5 | 2.5 | 2 | 74.0 | 6.0 | −8.7 | 0.3 | 1.8 | 3 |
| AT295 | [hGIP(3-30)NH2[G4K]-C16diacid/4] | −8.1 | 0.7 | 9.5 | 3 | 78.6 | 7.5 | −8.6 | 0.4 | 2.6 | 3 |
| AT296 | [hGIP(3-30)NH2[T5K]-C16diacid/5] | −7.8 | 0.1 | 14.0 | 3 | 6.7 | 2.7 | −8.6 | 2.3 | 2.6 | 3 |
| AT297 | [hGIP(3-30)NH2[F6K]-C16diacid/6] | −6.2 | 0.2 | 603.0 | 3 | 19.0 | 2.8 | −7.0 | 0.4 | 9.0 | 3 |
| AT298 | [hGIP(3-30)NH2[I7K]-C16diacid/7] | −7.5 | 0.2 | 33.0 | 3 | no ag. | | | | | 3 |
| AT299 | [hGIP(3-30)NH2[S8K]-C16diacid/8] | −6.7 | 0.1 | 199.0 | 3 | 15.2 | 1.8 | −7.8 | 0.4 | 15.0 | 3 |
| AT300 | [hGIP(3-30)NH2[D9K]-C16diacid/9] | −7.7 | 0.1 | 22.0 | 3 | no ag. | | | | | 3 |
| AT301 | [hGIP(3-30)NH2[Y10K]-C16diacid/10] | −6.8 | 0.2 | 163.0 | 3 | 8.5 | 1.3 | −7.9 | 0.7 | 12.0 | 3 |
| AT302 | [hGIP(3-30)NH2[S11K]-C16diacid/11] | −7.2 | 0.1 | 69.0 | 3 | no ag. | | | | | 3 |
| AT303 | [hGIP(3-30)NH2[I12K]-C16diacid/12] | −7.0 | 0.1 | 90.0 | 3 | 24.2 | 2.2 | −7.6 | 0.3 | 28.0 | 3 |
| AT304 | [hGIP(3-30)NH2[A13K]-C16diacid/13] | −6.7 | 0.1 | 199.0 | 3 | no ag. | | | | | 3 |
| AT305 | [hGIP(3-30)NH2[M14K]-C16diacid/14] | −6.8 | 0.2 | 166.0 | 3 | 12.0 | 1.3 | −8.1 | 0.4 | 8.0 | 3 |
| AT306 | [hGIP(3-30)NH2[D15K]-C16diacid/15] | −7.3 | 0.2 | 53.0 | 3 | 6.6 | 2.0 | −7.9 | 0.9 | 13.0 | 3 |
| AT370 | [hGIP(3-30)NH2—C16diacid/16] | −7.6 | 0.1 | 24.9 | 2 | no ag. | | | | | 3 |
| AT307 | [hGIP(3-30)NH2[I17K]-C16diacid/17] | −7.0 | 0.1 | 93.0 | 3 | 4.9 | 1.4 | −7.9 | 1.4 | 14.0 | 3 |
| AT308 | [hGIP(3-30)NH2[Q19K]-C16diacid/19] | −6.9 | 0.2 | 132.0 | 3 | 7.9 | 1.3 | −7.5 | 0.4 | 34.0 | 3 |
| AT309 | [hGIP(3-30)NH2[Q20K]-C16diacid/20] | −7.4 | 0.1 | 36.0 | 3 | no ag. | | | | | 3 |
| AT310 | [hGIP(3-30)NH2[D21K]-C16diacid/21] | −7.3 | 0.2 | 49.0 | 3 | 6.2 | 3.0 | −7.4 | 1.4 | 39.0 | 3 |
| AT311 | [hGIP(3-30)NH2[F22K]-C16diacid/22] | −6.0 | 0.3 | 923.0 | 3 | 17.5 | 7.6 | −6.1 | 0.6 | 784.0 | 3 |
| AT312 | [hGIP(3-30)NH2[V23K]-C16diacid/23] | 0.0 | 0.0 | 0.0 | 3 | 54.0 | 12.6 | −5.4 | 0.3 | 4076.0 | 3 |
| AT313 | [hGIP(3-30)NH2[N24K]-C16diacid/24] | −6.5 | 0.2 | 348.0 | 3 | 7.2 | 2.1 | −7.0 | 0.8 | 97.0 | 3 |
| AT314 | [hGIP(3-30)NH2[W25K]-C16diacid/25] | −7.0 | 0.2 | 101.0 | 3 | 28.4 | 2.9 | −7.2 | 0.3 | 62.0 | 3 |
| AT315 | [hGIP(3-30)NH2[L26K]-C16diacid/26] | −6.3 | 0.3 | 556.0 | 3 | 5.9 | 1.7 | −6.7 | 0.6 | 183.0 | 3 |
| AT316 | [hGIP(3-30)NH2[L27K]-C16diacid/27] | −6.2 | 0.4 | 649.0 | 3 | 6.2 | 2.2 | −6.5 | 0.8 | 294.0 | 3 |
| AT317 | [hGIP(3-30)NH2[A28K]-C16diacid/28] | −6.6 | 0.2 | 228.0 | 3 | 21.8 | 2.9 | −7.2 | 0.4 | 62.0 | 3 |
| AT318 | [hGIP(3-30)NH2[Q29K]-C16diacid/29] | −6.6 | 0.3 | 224.0 | 3 | 10.8 | 2.4 | −6.9 | 0.5 | 131.0 | 3 |
| NA | hGIP(5-30)NH2 | −7.6 | 0.1 | 28.0 | >3 | | | | | | |
| AT118 | [hGIP(5-30)NH2—C12/5] | −7.5 | −0.2 | 29 | 3 | 0 | 0 | 0.0 | 0 | 0 | 3 |
| AT119 | [hGIP(5-30)NH2—C12/16] | −7.6 | −0.2 | 26 | 3 | 0 | 0 | 0.0 | 0 | 0 | 3 |
| AT120 | [hGIP(5-30)NH2—C12/30] | 0.0 | 0.0 | 0 | 3 | 0 | 0 | 0.0 | 0 | 0 | 3 |
| AT121 | [hGIP(5-30)NH2—C14/5] | −7.3 | −0.2 | 54 | 2 | 0 | 0 | 0.0 | 0 | 0 | 3 |
| AT122 | [hGIP(5-30)NH2—C14/16] | −7.2 | −0.2 | 61 | 3 | 0 | 0 | 0.0 | 0 | 0 | 3 |
| AT123 | [hGIP(5-30)NH2—C14/30] | 0.0 | 0.0 | 0 | 3 | 64 | −11 | −7 | 0 | 78 | 3 |
| AT124 | [hGIP(5-30)NH2—C16/5] | −6.8 | −0.2 | 145 | 3 | 0 | 0 | 0 | 0 | 0 | |
| AT125 | [hGIP(5-30)NH2—C16/16] | −6.9 | −0.2 | 131 | 2 | 0 | 0 | 0 | 0 | 0 | |
| AT126 | [hGIP(5-30)NH2—C16/30] | 0.0 | 0.0 | 0 | 3 | 75 | −9 | −7 | 0 | 316 | 3 |
| AT127 | [hGIP(5-30)NH2—C18/5] | −6.5 | 0.0 | 353 | 3 | 0 | 0 | 0 | 0 | 0 | |
| AT128 | [hGIP(5-30)NH2—C18/16] | −6.9 | 0.6 | 114 | 2 | 25 | −5 | −6 | 0 | 706 | 2 |
| AT129 | [hGIP(5-30)NH2—C18/30] | 0 | 0 | 0 | 1 | 0 | 0 | 0.0 | 0 | 0 | 1 |
| AT133 | [hGIP(5-30)NH2[K16R; H18K; K30R]-C16/5] | −5.4 | 1.1 | 3811 | 3 | 0 | 0 | 0 | 0 | 0 | 3 |
| AT134 | [hGIP(5-30)NH2[K16R; H18K; K30R]-16/18] | −7.0 | 0.2 | 93 | 3 | 11 | 1 | −7 | 0 | 35 | 3 |
| AT135 | [hGIP(5-30)NH2[K16R; K30R]-C16/5] | 0 | 0.0 | 0 | 3 | 0 | 0 | 0 | 0 | 0 | 3 |
| AT136 | [hGIP(5-30)NH2—C14diacid/5] | −6.9 | 0.3 | 124 | 3 | 20 | 1 | −8 | 0 | 8 | 3 |
| AT137 | [hGIP(5-30)NH2—C16diacid/5] | −6.7 | 0.3 | 182 | 3 | 12 | 1 | −8 | 0 | 18 | 3 |
| AT138 | [hGIP(5-30)NH2—C18diacid/5] | 0 | 0.0 | 0 | 3 | 0 | 0 | 0 | 0 | 0 | 3 |
| AT139 | [hGIP(5-30)NH2—C14diacid/16] | −6.9 | 0.2 | 139 | 3 | 0 | 0 | 0 | 0 | 0 | 3 |
| AT140 | [hGIP(5-30)NH2—C16diacid/16] | −6.7 | 0.1043 | 205 | 3 | 0 | 0 | 0 | 0 | 0 | 3 |
| AT141 | [hGIP(5-30)NH2—C18diacid/16] | −6.0 | 0.2 | 1122 | 3 | 0 | 0 | 0 | 0 | 0 | 3 |
| AT145 | [hGIP(5-30)NH2[H18K]-C16/18] | −7.2 | 0.4 | 66 | 3 | 16 | 3 | −7 | 1 | 33 | 3 |
| AT157 | [hGIP(5-30)NH2[K16R; H18K; K30R]-C16diacid/18] | −8.1 | 0.1 | 7 | 3 | 12 | 1 | −8 | 0 | 3 | 3 |
| AT161 | [hGIP(5-30)NH2[H18K]-C18/18] | −6.6 | 0.2 | 252 | 3 | 7 | 3 | −6 | 0 | 1064 | 3 |
| AT293 | [hGIP(5-30)NH2[T5KK]-C16diacid/5] | −7.8 | 0.1 | 14 | 3 | 0 | 0 | 0 | 0 | 0 | 3.0 |
| AT168 | [hGIP(5-30)NH2[F6K]-C16diacid/6] | −7.0 | 0.2 | 96 | 3 | 0 | 0 | 0 | 0 | 0 | 3 |
| AT169 | [hGIP(5-30)NH2[I7K]-C16diacid/7] | −7.4 | 0.2 | 37 | 3 | 0 | 0 | 0 | 0 | 0 | 3 |
| AT170 | [hGIP(5-30)NH2[S8K]-C16diacid/8] | −6.3 | 0.3 | 507 | 3 | 0 | 0 | 0 | 0 | 0 | 3 |
| AT171 | [hGIP(5-30)NH2[D9K]-C16diacid/9] | −7.5 | 0.1 | 35 | 3 | 0 | 0 | 0 | 0 | 0 | 3 |
| AT172 | [hGIP(5-30)NH2[Y10K]-C16diacid/10] | −6.6 | 0.2 | 259 | 3 | 0 | 0 | 0 | 0 | 0 | 3 |
| AT173 | [hGIP(5-30)NH2[S11K]-C16diacid/11] | −8.0 | 0.1 | 10 | 3 | 0 | 0 | 0 | 0 | 0 | 3 |
| AT174 | [hGIP(5-30)NH2[I12K]-C16diacid/12] | −7.6 | 0.1 | 23 | 3 | 0 | 0 | 0 | 0 | 0 | 3 |
| AT175 | [hGIP(5-30)NH2[A13K]-C16diacid/13] | −7.8 | 0.2 | 17 | 3 | 0 | 0 | 0 | 0 | 0 | 3 |
| AT176 | [hGIP(5-30)NH2[M14K]-C16diacid/14] | −6.9 | 0.1 | 121 | 3 | 12 | 5 | −7 | 0 | 121 | 3 |
| AT177 | [hGIP(5-30)NH2[D15K]-C16diacid/15] | −7.2 | 0.4 | 59 | 3 | 30 | 9 | −7 | 0 | 59 | 3 |
| AT178 | [hGIP(5-30)NH2[I17K]-C16diacid/17] | −7.5 | 0.3 | 33 | 3 | 0 | 0 | 0 | 0 | 0 | 3 |
| AT156 | [hGIP(5-30)NH2[H18K]-C16diacid/18] | −7.9 | 0.1 | 12 | 3 | 12 | 1 | −9 | 0 | 2 | 4 |

TABLE 1-continued

Antagonistic and agonistic properties of human GIP(3-30)NH₂ and human GIP(3-50)NH₂ peptides, modified and lapidated as described in the table.

| ID | Formula | cAMP antagonism | | | | cAMP agonism | | | | | |
|---|---|---|---|---|---|---|---|---|---|---|---|
| | | log | SEM | nM | n | Emax | SEM | EC50 | SEM | nM | n |
| AT179 | [hGIP(5-30)NH2[Q19K]-C16diacid/19] | −7.1 | 0.4 | 89 | 3 | 32 | 9 | −7 | 0 | 89 | 3 |
| AT180 | [hGIP(5-30)NH2[Q20K]-C16diacid/20] | −7.4 | 0.2 | 37 | 3 | 0 | 0 | 0 | 0 | 0 | 3 |
| AT181 | [hGIP(5-30)NH2[D21K]-C16diacid/21] | −7.8 | 0.1 | 16 | 3 | 9 | 2 | −9 | 1 | 2 | 3 |
| AT182 | [hGIP(5-30)NH2[F22K]-C16diacid/22] | −6.2 | 0.2 | 634 | 3 | 13 | 7 | −6 | 0 | 634 | 3 |
| AT183 | [hGIP(5-30)NH2[V23K]-C16diacid/23] | −5.8 | 0.3 | 1770 | 3 | 0 | 0 | 0 | 0 | 0 | 3 |
| AT184 | [hGIP(5-30)NH2[N24K]-C16diacid/24] | −7.0 | 0.1 | 91 | 3 | 0 | 0 | 0 | 0 | 0 | 3 |
| AT185 | [hGIP(5-30)NH2[W25K]-C16diacid/25] | −7.4 | 0.2 | 44 | 3 | 18 | 5 | −7 | 0 | 44 | 3 |
| AT186 | [hGIP(5-30)NH2[L26K]-C16diacid/26] | −7.1 | 0.3 | 79 | 3 | 0 | 0 | 0 | 0 | 0 | 3 |
| AT187 | [hGIP(5-30)NH2[L27K]-C16diacid/27] | −5.6 | 0.3 | 2382 | 3 | 25 | 12 | −6 | 0 | 2382 | 3 |
| AT188 | [hGIP(5-30)NH2[A28K]-C16diacid/28] | −6.8 | 0.1 | 152 | 3 | 10 | 3 | −7 | 0 | 152 | 3 |
| AT189 | [hGIP(5-30)NH2[Q29K]-C16diacid/29] | −7.1 | 0.1 | 79 | 3 | 12 | 3 | −7 | 0 | 79 | 3 |
| AT186 | [hGIP(5-30)NH2[L26K]-C16diacid/26] | −7.1 | 0 | 79 | 3 | 0 | 0 | 0 | 0 | 0 | 3 |
| AT187 | [hGIP(5-30)NH2[L27K]-C16diacid/27] | −5.6 | 0 | 2382 | 3 | 25 | 12 | −5.6 | 0 | 2382 | 3 |
| AT188 | [hGIP(5-30)NH2[A28K]-C16diacid/28] | −6.8 | 0 | 152 | 3 | 10 | 3 | −6.8 | 0 | 152 | 3 |
| AT189 | [hGIP(5-30)NH2[Q29K]-C16diacid/29] | −7.1 | 0 | 79 | 3 | 12 | 3 | −7.1 | 0 | 79 | 3 |
| AT372 | [hGIP(5-30)NH2[Q30K]-C16diacid/30] | −6.5 | 0 | 284 | 2 | 6 | 1.0 | −10 | 1 | 0.1 | 3 |

No ag. = no agonism

TABLE 2

Heterologous competition binding in transiently transfected COS-7 cells expressing the human GIP receptor following incubation with the lipidated (fatty acyl) hGIP(3-30)NH₂ and hGIP(5-30)NH₂.

| ID | Formula | Binding log | SEM | nM | n |
|---|---|---|---|---|---|
| NA | hGIP(3-30)NH2 | | | | |
| AT101 | [hGIP(3-30)NH2-C12/3] | −8.0 | −0.3 | 9.9 | 3 |
| AT102 | [hGIP(3-30)NH2-C12/16] | −7.2 | −0.4 | 59.1 | 3 |
| AT103 | [hGIP(3-30)NH2-C12/30] | −5.3 | −0.4 | 4709.8 | 3 |
| AT104 | [hGIP(3-30)NH2-C16/3] | −7.1 | −0.3 | 75.0 | 3 |
| AT105 | [hGIP(3-30)NH2-C16/16] | −6.3 | −0.3 | 522.0 | 3 |
| AT106 | [hGIP(3-30)NH2-C16/30] | −5.9 | na | 1409.3 | 1 |
| AT107 | [hGIP(3-30)NH2[T5W; D15E; H18A]-C16/16] | −5.3 | −0.2 | 5220.0 | 3 |
| AT110 | [hGIP(3-30)NH2-C14/3] | −7.3 | −0.1 | 55.5 | 3 |
| AT111 | [hGIP(3-30)NH2-C14/16] | −6.6 | −0.2 | 261.2 | 3 |
| AT112 | [hGIP(3-30)NH2-C14/30] | −6.3 | −0.4 | 450.8 | 2 |
| AT113 | [hGIP(3-30)NH2-C18/3] | −4.4 | −1.1 | 41400.0 | 3 |
| AT114 | [hGIP(3-30)NH2-C18/16] | −6.2 | −0.1 | 622.3 | 3 |
| AT115 | [hGIP(3-30)NH2-C18/30] | −5.8 | −0.1 | 1515.3 | 2 |
| AT116 | [hGIP(3-30)NH2-C12/18] | −7.1 | −0.2 | 71.2 | 3 |
| AT117 | [hGIP(3-30)NH2[H18K]-C16/18] | −6.5 | −0.2 | 292.2 | 3 |
| AT130 | [hGIP(3-30)NH2[D15E; H18A]-C12/30] | −5.9 | −0.2 | 1213.4 | 3 |
| AT131 | [hGIP(3-30)NH2[D15E; H18A]-C16/16] | −5.2 | −0.9 | 6511.3 | 3 |
| AT143 | [hGIP(3-30)NH2[M14L; H18K]-C16/18] | | | 80.0 | |
| AT144 | [hGIP(3-30)NH2[K16R; H18K; K30R]-C16/18] | −6.528 | 0.2138 | 297.0 | 3 |
| AT148 | [hGIP(3-30)NH2-C12/3] | −8 | 0.07501 | 24.0 | 3 |
| AT149 | [hGIP(3-30)NH2[H18R; K30R]-C12diacid/3] | −7 | 0.164 | 103.0 | 3 |
| AT150 | [hGIP(3-30)NH2[H18R; K30R]-C16/3] | | | | |
| AT153 | [hGIP(3-30)NH2[H18R; K30R]-C12/16] | −7 | 0.1388 | 316.0 | 3 |
| AT154 | [hGIP(3-30)NH2-C12/16] | −8 | 0.08655 | 27.0 | 3 |
| AT158 | [hGIP(3-30)NH2[H18K]-C16diacid/18] | | | 8.2 | 3 |
| AT159 | [hGIP(3-30)NH2[K16R; H18K; K30R]-C16diacid/18] | | | 18.0 | 3 |
| AT160 | [hGIP(3-30)NH2[H18K]-C18/18] | | | 49.0 | 3 |
| AT162 | [hGIP(3-30)NH2[H18R; K30R]-C18/16] | | | 85.0 | 3 |
| AT163 | [hGIP(3-30)NH2[H18K]-C16/16] | | | 205.0 | 3 |
| AT118 | [hGIP(5-30)NH2-C12/5] | −7.0 | −0.09 | 102.0 | 3 |
| AT119 | [hGIP(5-30)NH2-C12/16] | −6.7 | −0.18 | 193.8 | 3 |
| AT120 | [hGIP(5-30)NH2-C12/30] | −6.0 | −0.05 | 1085.2 | 2 |
| AT121 | [hGIP(5-30)NH2-C14/5] | −6.8 | −0.24 | 172.8 | 3 |
| AT122 | [hGIP(5-30)NH2-C14/16] | −6.2 | −0.10 | 591.1 | 3 |
| AT123 | [hGIP(5-30)NH2-C14/30] | −6.2 | −0.12 | 673.5 | 3 |
| AT124 | [hGIP(5-30)NH2-C16/5] | −6.4 | −0.12 | 360.6 | 2 |
| AT125 | [hGIP(5-30)NH2-C16/16] | −6.1 | −0.18 | 713.9 | 3 |
| AT126 | [hGIP(5-30)NH2-C16/30] | −5.1 | −0.20 | 7786.3 | 3 |
| AT127 | [hGIP(5-30)NH2-C18/5] | −5.7 | −0.14 | 2041.7 | 2 |
| AT128 | [hGIP(5-30)NH2-C18/16] | −6.3 | −0.27 | 466.3 | 3 |
| AT129 | [hGIP(5-30)NH2-C18/30] | −3.9 | −1.02 | | 3 |

TABLE 2-continued

Heterologous competition binding in transiently transfected COS-7 cells expressing the human GIP receptor following incubation with the lipidated (fatty acyl) hGIP(3-30)NH$_2$ and hGIP(5-30)NH$_2$.

| ID | Formula | Binding log | SEM | nM | n |
|---|---|---|---|---|---|
| AT133 | [hGIP(5-30)NH2[K16R; H18K; K30R]-C16/5] | −5.8 | −0.03 | 1719.2 | 3 |
| AT134 | [hGIP(5-30)NH2[K16R; H18K; K30R]-C16/18] | −6.1 | −0.05 | 882.4 | 3 |
| AT135 | [hGIP(5-30)NH2[K16R; K30R]-C16/5] | −5.2 | −0.21 | 5938.4 | 3 |
| AT136 | [hGIP(5-30)NH2-C14diacid/5] | −7.3 | −0.11 | 45.4 | 3 |
| AT137 | [hGIP(5-30)NH2-C16diacid/5] | −6.5 | −0.14 | 285.5 | 3 |
| AT138 | [hGIP(5-30)NH2-C18diacid/5] | −5.6 | −0.17 | 2638.4 | 3 |
| AT139 | [hGIP(5-30)NH2-C14diacid/16] | −6.8 | −0.08 | 153.2 | 3 |
| AT140 | [hGIP(5-30)NH2-C16diacid/16] | −5.7 |  | 2162.7 | 3 |
| AT141 | [hGIP(5-30)NH2-C18diacid/16] | −5.7 |  | 1899.6 | 3 |
| AT145 | [hGIP(5-30)NH2[H18K]-C16/18] | −6.8 | 0.1891 | 155.3 | 3 |
| AT168 | [hGIP(5-30)NH2[F6K]-C16diacid/6] | −7.3 | 0.05 | 48 | 3 |
| AT169 | [hGIP(5-30)NH2[I7K]-C16diacid/7] | −7.5 | 0.1 | 28 | 3 |
| AT170 | [hGIP(5-30)NH2[S8K]-C16diacid/8] | −6.2 | 0.08 | 628 | 3 |
| AT171 | [hGIP(5-30)NH2[D9K]-C16diacid/9] | −7.1 | 0.1 | 86 | 3 |
| AT172 | [hGIP(5-30)NH2[Y10K]-C16diacid/10] | −6.6 | 0.05 | 252 | 3 |
| AT173 | [hGIP(5-30)NH2[S11K]-C16diacid/11] | −8.1 | 0.1 | 8 | 3 |
| AT174 | [hGIP(5-30)NH2[I12K]-C16diacid/12] | −7.1 | 0.13 | 80 | 3 |
| AT175 | [hGIP(5-30)NH2[A13K]-C16diacid/13] | −7.1 | 0.1 | 73 | 3 |
| AT176 | [hGIP(5-30)NH2[M14K]-C16diacid/14] | −6.9 | 0.10 | 114 | 3 |
| AT177 | [hGIP(5-30)NH2[D15K]-C16diacid/15] | −6.9 | 0.1 | 134 | 3 |
| AT178 | [hGIP(5-30)NH2[I17K]-C16diacid/17] | −7.2 | 0.07 | 66 | 3 |
| AT156 | [hGIP(5-30)NH2[H18K]-C16diacid/18] |  |  |  | 3 |
| AT179 | [hGIP(5-30)NH2[Q19K]-C16diacid/19] | −6.3 | 0.1 | 453 | 3 |
| AT180 | [hGIP(5-30)NH2[Q20K]-C16diacid/20] | −7.0 | 0.09 | 106 | 3 |
| AT181 | [hGIP(5-30)NH2[D21K]-C16diacid/21] | −7.3 | 0.1 | 48 | 3 |
| AT182 | [hGIP(5-30)NH2[F22K]-C16diacid/22] | −6.0 | 0.09 | 962 | 3 |
| AT183 | [hGIP(5-30)NH2[V23K]-C16diacid/23] | −5.1 | 0.3 | 7129 | 3 |
| AT184 | [hGIP(5-30)NH2[N24K]-C16diacid/24] | −6.6 | 0.12 | 247 | 3 |
| AT185 | [hGIP(5-30)NH2[W25K]-C16diacid/25] | −7.1 | 0.1 | 87 | 3 |
| AT186 | [hGIP(5-30)NH2[L26K]-C16diacid/26] | −6.8 | 0.11 | 144 | 3 |
| AT187 | [hGIP(5-30)NH2[L27K]-C16diacid/27] | −4.6 | 0.8 | 26485 | 3 |
| AT188 | [hGIP(5-30)NH2[A28K]-C16diacid/28] | −6.7 | 0.12 | 183 | 3 |
| AT189 | [hGIP(5-30)NH2[Q29K]-C16diacid/29] | −6.9 | 0.1 | 118 | 3 |
| AT186 | [hGIP(5-30)NH2[L26K]-C16diacid/26] | −6.842 | 0.11 | 144 | 3 |
| AT187 | [hGIP(5-30)NH2[L27K]-C16diacid/27] | −4.577 | 0.8 | 26485 | 3 |
| AT188 | [hGIP(5-30)NH2[A28K]-C16diacid/28] | −6.737 | 0.12 | 183 | 3 |
| AT189 | [hGIP(5-30)NH2[Q29K]-C16diacid/29] | −6.928 | 0.12 | 118 | 3 |

TABLE 3

T$_{1/2}$ and IC$_{50}$-values from binding studies in the presence and absence of 2% HSA and corresponding calculated fold change.

| ID | Formula | T½, hours | Binding HSA(2%)/Casein(0.1%) | | | | |
|---|---|---|---|---|---|---|---|
| | | | logIC50 2% HSA | logIC50 2% HSA (nM) | logIC50 0.1% casein | logIC50 2% HSA (nM) | Fold change HSA (2%)/Casein (0.1%) |
| AT111 | [hGIP(3-30)NH2—C14/16] |  | −5.7 | 2091 | −6.4 | 407 | 5.1 |
| AT114 | [hGIP(3-30)NH2—C18/16] |  | −5.3 | 5458 | −6.3 | 489 | 11.2 |
| AT115 | [hGIP(3-30)NH2—C18/30] |  |  |  |  |  |  |
| AT116 | [hGIP(3-30)NH2—C12/18] |  | −6.5 | 321 | −7.2 | 62 | 5.2 |
| AT117 | [hGIP(3-30)NH2[H18K]-C16/18] | 8 | −5.8 | 1731 | −7.0 | 110 | 15.7 |
| AT159 | [hGIP(3-30)NH2[K16R; H18K; K30R]-C16diacid/18] | 6 |  |  |  |  |  |
| AT118 | [hGIP(5-30)NH2—C12/5] |  | −6.1 | 881 | −6.9 | 115 | 7.7 |
| AT119 | [hGIP(5-30)NH2—C12/16] |  | −5.6 | 2663 | −6.4 | 369 | 7.2 |
| AT121 | [hGIP(5-30)NH2—C14/5] |  | −6.0 | 966 | −6.8 | 170 | 5.7 |
| AT122 | [hGIP(5-30)NH2—C14/16] |  | −5.2 | 6081 | −5.9 | 1234 | 4.9 |
| AT124 | [hGIP(5-30)NH2—C16/5] |  | −5.1 | 8241 | −5.8 | 1594 | 5.2 |
| AT127 | [hGIP(5-30)NH2—C18/5] |  | 0.0 |  | −5.8 | 1469 | 0.0 |
| AT133 | [hGIP(5-30)NH2[K16R; H18K; K30R]-C16/5] |  | −5.7 | 2205 | −5.8 | 1719 | 1.3 |
| AT134 | [hGIP(5-30)NH2[K16R; H18K; K30R]-C16/18] |  | −5.3 | 4887 | −6.1 | 882 | 5.5 |
| AT135 | [hGIP(5-30)NH2[K16R; K30R]-C16/5] |  | −6.0 | 977 | −5.2 | 5938 | 0.2 |
| AT136 | [hGIP(5-30)NH2—C14diacid/5] |  | −6.1 | 713 | −7.3 | 45 | 15.7 |
| AT137 | [hGIP(5-30)NH2—C16diacid/5] |  | −6.3 | 555 | −6.5 | 286 | 1.9 |
| AT138 | [hGIP(5-30)NH2—C18diacid/5] |  | −5.0 | 10093 | −5.6 | 2638 | 3.8 |

TABLE 3-continued

T$_{1/2}$ and IC$_{50}$-values from binding studies in the presence and absence of 2% HSA and corresponding calculated fold change.

| ID | Formula | T½, hours | logIC50 2% HSA | Binding HSA(2%)/Casein(0.1%) logIC50 2% HSA (nM) | logIC50 0.1% casein | logIC50 2% HSA (nM) | Fold change HSA (2%)/Casein (0.1%) |
|---|---|---|---|---|---|---|---|
| AT139 | [hGIP(5-30)NH2—C14diacid/16] | | −6.4 | 401 | −6.8 | 153 | 2.6 |
| AT140 | [hGIP(5-30)NH2—C16diacid/16] | | −5.5 | 3278 | −5.7 | 2163 | 1.5 |
| AT141 | [hGIP(5-30)NH2—C18diacid/16] | | −4.9 | 12359 | −5.7 | 1900 | 6.5 |
| AT168 | [hGIP(5-30)NH2[F6K]-C16diacid/6] | | −7.0 | 100.0 | −7.3 | 50.1 | 2.0 |
| AT169 | [hGIP(5-30)NH2[I7K]-C16diacid/7] | | −6.8 | 166.0 | −7.5 | 28.8 | 5.8 |
| AT170 | [hGIP(5-30)NH2[S8K]-C16diacid/8] | | −5.9 | 1380.4 | −6.2 | 631.0 | 2.2 |
| AT171 | [hGIP(5-30)NH2[D9K]-C16diacid/9] | | −6.2 | 660.7 | −7.1 | 79.4 | 8.3 |
| AT172 | [hGIP(5-30)NH2[Y10K]-C16diacid/10] | | −6.0 | 955.0 | −6.6 | 251.2 | 3.8 |
| AT173 | [hGIP(5-30)NH2[S11K]-C16diacid/11] | | −7.2 | 60.3 | −8.1 | 8.1 | 7.4 |
| AT174 | [hGIP(5-30)NH2[I12K]-C16diacid/12] | | −6.6 | 281.8 | −7.1 | 79.4 | 3.5 |
| AT175 | [hGIP(5-30)NH2[A13K]-C16diacid/13] | 6 | −6.3 | 562.3 | −7.1 | 72.4 | 7.8 |
| AT176 | [hGIP(5-30)NH2[M14K]-C16diacid/14] | | −6.3 | 562.3 | −6.9 | 114.8 | 4.9 |
| AT177 | [hGIP(5-30)NH2[D15K]-C16diacid/15] | | −6.29 | 512.9 | −6.87 | 134.9 | 3.8 |
| AT178 | [hGIP(5-30)NH2[I17K]-C16diacid/17] | | −6.7 | 195.0 | −7.2 | 66.1 | 3.0 |
| AT179 | [hGIP(5-30)NH2[Q19K]-C16diacid/19] | | −7.42 | 38.0 | −7.98 | 10.5 | 3.6 |
| AT180 | [hGIP(5-30)NH2[Q20K]-C16diacid/20] | | −5.8 | 1698.2 | −6.3 | 457.1 | 3.7 |
| AT181 | [hGIP(5-30)NH2[D21K]-C16diacid/21] | | −6.3 | 549.5 | −7.0 | 104.7 | 5.2 |
| AT182 | [hGIP(5-30)NH2[F22K]-C16diacid/22] | | −6.9 | 141.3 | −7.3 | 47.9 | 3.0 |
| AT183 | [hGIP(5-30)NH2[V23K]-C16diacid/23] | | −5.8 | 1698.2 | −6.0 | 955.0 | 1.8 |
| AT184 | [hGIP(5-30)NH2[N24K]-C16diacid/24] | | −5.0 | 11220.2 | −5.2 | 7079.5 | 1.6 |
| AT185 | [hGIP(5-30)NH2[W25K]-C16diacid/25] | | −5.9 | 1148.2 | −6.6 | 245.5 | 4.7 |
| AT186 | [hGIP(5-30)NH2[L26K]-C16diacid/26] | | −6.5 | 331.1 | −7.1 | 87.1 | 3.8 |
| AT187 | [hGIP(5-30)NH2[L27K]-C16diacid/27] | | −6.2 | 676.1 | −6.8 | 144.5 | 4.7 |
| AT188 | [hGIP(5-30)NH2[A28K]-C16diacid/28] | | 0.0 | 0.0 | −4.6 | 26302.7 | 0.0 |
| AT189 | [hGIP(5-30)NH2[Q29K]-C16diacid/29] | | −6.2 | 575.4 | −6.7 | 182.0 | 3.2 |

The tables below (Table 3b) summarize the initial data for fold change in affinity in the absence and presence of 2% HSA and the antagonistic potencies for each of the tested peptides:

TABLE 3b

| Acylation at position 3 | | | Binding | |
|---|---|---|---|---|
| ID | Mutation | Acylation | IC50 (nM) | fold (paired) |
| AT101 | WT | C12 | 9.9 | 0.7 |
| AT104 | WT | C16 | 75 | 4.9 |
| AT110 | WT | C14 | 55 | 5.2 |
| AT113 | WT | C18 | 41400 | 16380 |

| Acylation at position 16 | | | | Binding | | | cAMP - antagonisme | |
|---|---|---|---|---|---|---|---|---|
| ID | Mutation | Acylation | IC50 (nM) | fold (paired) | logIC50 2% HSA (nM) | logIC50 0.1% casein (nM) | Fold change | IC50 (nM) | fold (paired) |
| AT102 | WT | C12 | 59.1 | 6.1 | | | | | |
| AT105 | WT | C16 | 522.0 | 34 | | | | 23.8 | 3.4 |
| AT107 | T5W; D15E; H18A | C16 | 5220 | 186 | | | | 76.9 | 3.1 |
| AT109 | E3pGlu | C16 | 1580 | 74 | | | | 56.4 | 8.0 |
| AT111 | WT | C14 | 261.2 | 31 | 2091 | 407 | 5.1 | 21.9 | 3.3 |
| AT114 | WT | C18 | 102.0 | 6.7 | 881 | 115 | 7.7 | 29.2 | 2.3 |
| AT131 | D15E; H18A | C16 | 6511 | 49 | | | | 65.0 | 1.1 |
| AT162 | H18K; K30R | C18 | 59.8 | 2.6 | 336.5 | 59.8 | 5.6 | 26.3 | 0.5 |
| AT162 | H18K; K30R | C16 | 213.3 | 9.2 | 704.7 | 213.3 | 3.3 | 213.3 | 4.1 |

TABLE 3b-continued

| | | | Binding | | | | | cAMP - antagonisme | |
| --- | --- | --- | --- | --- | --- | --- | --- | --- | --- |
| Acylation at position 18 | | | | fold | logIC50 2% HSA | logIC50 0.1% casein | | | fold |
| ID | Mutation | Acylation | IC50 (nM) | (paired) | (nM) | (nM) | Fold change | IC50 (nM) | (paired) |
| AT116 | H18K | C12 | 71.2 | 5 | 321 | 61.5 | 5.2 | 11.9 | 1.2 |
| AT117 | H18K | C16 | 292 | 12 | 1731 | 110 | 15.7 | 19.4 | 2.3 |
| AT143 | M14L; H18K | C16 | 86.1 | 11 | 105 | 86.1 | 1.2 | 13.3 | 0.3 |
| AT158 | H18K | C16-diacid | 7.9 | 1 | 16 | 7.9 | 2.0 | 4.5 | 0.1 |
| AT159 | K16R; H18K; K30R | C16-diacid | 25.0 | 3 | 20 | 25.0 | 0.8 | 5.6 | 0.1 |
| AT160 | H18K | C18 | 48.8 | 6 | 175 | 48.8 | 3.6 | 36.1 | 0.7 |

Results:

Lipidation of the N-terminus of GIP(3-30)NH$_2$ resulted in decreased affinity, which correlated with increased lipid length (see table 1 for the fold decrease in affinity compared to GIP(3-30)NH$_2$) and a completely abolished antagonistic profile due to increased agonistic propensity (table 1). The same pattern was observed for lipidation of the C-terminus (FIG. 1 and table 1). Again, the affinities of the lipidated analogues were dramatically decreased compared to GIP(3-30)NH$_2$ and no high potent antagonistic profiles were obtained as increased tendency to agonism was observed. On the other hand, lipidation of the positions 5, 7, 9, 11 and of the midregion (position 15 to 21) of GIP(3-30)NH$_2$ resulted in surprisingly high potency GIP receptor antagonists (FIG. 1 and table 1). The antagonistic potencies for analogues lipidated at position 5, 7, 9, 11, 15, 17, 19, 20, and 21 were 14, 33, 22, 69, 53, 93, 132, 36, and 49 nM, respectively. AT105, AT111, AT114, AT162 and AT370 were lipidated at position 16 and the corresponding antagonistic potencies were 24, 22, 29, 26 and 25 nM, respectively while for position 18, all the lipidated analogues had an improved antagonistic potency compared to GIP(3-30)NH$_2$ (IC$_{50}$ values of 12, 15, 15, 5, 6 and 38 nM for AT116, AT117, AT143, AT158, AT159 and AT160, respectively) (FIG. 1). This clearly shows that position 3 and 30 are less useful for lipidation of GIP(3-30)NH$_2$ whereas lipidation of other regions and in particular position 18, results in high potent GIP receptor antagonists.

Example 2—Antagonistic Properties of Human GIP(5-30)NH$_2$ are Preserved Following Lipidation at the N-Terminus (Position 5) and Midregion but not at Position 30

As done for GIP(3-30)NH$_2$, GIP(5-30)NH$_2$ lipidated at different regions with different lengths of fatty acids (C12-C18, C14-C18 diacid) to develop a long acting GIP receptor antagonist. Like the lipidated GIP(3-30)NH$_2$ analogues, their antagonistic properties following lipidation were examined by studying their ability to inhibit a GIP-mediated cAMP response corresponding to 50-80% of maximum activation done in transiently transfected COS-7 cells expressing the human GIP receptor. In addition, we measured their affinities of selected analogues in the absence and presence of 2% human albumin as a proxy estimate for the compounds' ability to bind to human albumin (HSA) (Table 3).

Table 3b above summarize the initial data for fold change in affinity in the absence and presence of 2% HSA and the antagonistic potencies for each of the tested peptides.

Results:

In contrast to lipidation of the N-terminus of GIP(3-30)NH$_2$, the antagonistic properties were preserved for most analogues upon lipidation of the N-terminus of GIP(5-30)NH$_2$ (table 1). The antagonistic potencies for AT118, AT121, and AT293 were 29, 54, and 14 nm, respectively.

Many of the lipidated analogues had decreased affinities compared to GIP(3-30)NH$_2$ and their antagonistic potencies were likewise decreased. AT133, AT135 and AT138 failed to antagonize the GIP-mediated cAMP response. In contrast, AT118, AT121, AT136 and AT137 had affinities in the same range as GIP(3-30)NH$_2$ and were high potent antagonists with inhibitory potencies. Like GIP(3-30)NH$_2$, lipidation of the C-terminus (position 30) of GIP(5-30)NH$_2$ abolishes the antagonistic profile or greatly decreases the ability to inhibit a GIP-mediated cAMP response (table 1).

The GIP(5-30)NH$_2$ analogues lipidated in the midregion (position 16 and 18) demonstrated impressive antagonistic properties as some of the variants showed surprising improvements compared to the antagonistic profile of GIP (5-30)NH$_2$ (AT119, AT156 and AT157 with IC$_{50}$ values of 26, 12 and 7 nm compared to 25.8 nM for that of GIP(5-30)NH$_2$).

Taken together, this shows that position 30 is not optimal for lipidation of GIP(5-30)NH$_2$ where antagonism is required, however, other regions demonstrate preserved and even improved antagonistic profiles, including positions in the N-terminal region.

Example 3—Several Acylation Sites in GIP(5-30)NH$_2$ Show Great Potential

As done for GIP(3-30)NH$_2$ (see Example 1), to identify optimal acylation sites in GIP(5-30)NH$_2$ a lysine (Lys) scan was performed through the entire peptide to which a C16-diacid was coupled. Both the agonistic and antagonistic profiles of the analogues were tested in cAMP accumulation experiments done in transiently transfected COS-7 cells expressing the human GIP receptor. The agonistic properties were studied by the ability of the lipidated variants to induce a cAMP response on their own whereas the antagonistic properties were studied by the ability to inhibit a GIP-mediated cAMP response corresponding to 50-80% of maximum activation. In addition, we measured their ability to bind to human albumin (HSA) as an estimate of a possibly increase in $T_{1/2}$ in vivo.

Results:

All the tested variants were able to inhibit a GIP-mediated cAMP response and only few of the variants demonstrated low intrinsic cAMP activity with a maximum of 32% activity at 10 μM (Table 1). Compared to GIP(5-30)NH$_2$, antagonistic potencies were improved for lipidated analogues at position 5, 11, 12, 13, 18, 21 (14, 10, 23, 17, 12, and 16 nM, respectively). The highest antagonistic potencies were observed for AT173, AT174, AT175 and AT181 which all surpassed that of GIP(5-30)NH$_2$. When looking at the ability of the different analogues to bind HSA we observed that the lipidation position in the peptide plays an important role. Depending on lipidation site, the IC$_{50}$ values varied in the presence and absence of 2% HSA and resulted in fold differences ranging from 1.6 to 8.3 (table 3). Lipidation at position 7, 9, 11, 13 and 21 (AT169, AT171, AT173, AT175 and AT181, respectively) had the highest fold changes in IC$_{50}$ values between the presence and absence of 2% HSA with the values of 5.8, 8.3, 7.4, 7.8 and 5.2, respectively. Lipidation at position 7, 9, 11, 12, 13, 18, and 21 produced analogues with the best antagonistic potencies clearly indicating that these lipidation sites are highly promising lipidation sites for the development of high potent, long-acting GIP receptor antagonists.

The table below (Table 4) summarizes the initial data for antagonistic properties with the fold change from GIP(5-30)NH$_2$ (IC$_{50}$-values from binding studies in the presence and absence of 2% HSA and corresponding calculated fold change):

TABLE 4

Antagonist properties with the fold change from GIP(5-30)NH$_2$. In addition, IC$_{50}$-values from binding studies in the presence and absence of 2% HSA and corresponding calculated fold change.

| Table 4 | cAMP accumulation | | | Binding (+/−HSA) | | |
|---|---|---|---|---|---|---|
| | logIC$_{50}$ ± SEM | IC$_{50}$ (nM) | Fold | Ki (nM) + HSA | Ki (nM) − HSA | Fold |
| GIP(5-30)NH$_2$ | −7.56 ± 0.12 | 27.5 | — | 6.7 | 6.3 | 1.0 |
| AT137 [hGIP(5-30NH2—C16-diacid/5] | −6.99 ± 0.26 | 102.3 | 3.7 | 117.2 | 59.3 | 2.0 |
| AT168 [hGIP(5-30NH2[F6K]-C16-diacid/6] | −6.83 ± 0.06 | 147.9 | 5.3 | 97.7 | 41.3 | 2.3 |
| AT169 [hGIP(5-30NH2[I7K]-C16-diacid/7] | −7.09 ± 0.17 | 81.3 | 3.0 | 126.2 | 26.5 | 4.8 |
| AT170 [hGIP(5-30NH2[S8K]-C16-diacid/8] | −6.05 ± 0.16 | 891.3 | 32.4 | 1297.2 | 594.3 | 2.2 |
| AT171 [hGIP(5-30NH2[D9K]-C16-diacid/9] | −7.50 ± 0.11 | 31.6 | 1.1 | 500.0 | 79.1 | 6.3 |
| AT172 [hGIP(5-30NH2[Y10K]-C16-diacid/10] | −6.41 ± 0.23 | 389.0 | 14.1 | 807.2 | 281.2 | 2.8 |
| AT173 [hGIP(5-30NH2[S11K]-C16-diacid/11] | −8.04 ± 0.10 | 9.1 | 0.3 | 58.7 | 6.0 | 9.7 |
| AT174 [hGIP(5-30NH2[I12K]-C16-diacid/12] | −7.63 ± 0.13 | 23.4 | 0.9 | 342.0 | 56.1 | 6.1 |
| AT175 [hGIP(5-30NH2[A13K]-C16-diacid/13] | −7.85 ± 0.23 | 14.1 | 0.5 | 497.7 | 53.0 | 9.4 |
| AT176 [hGIP(5-30NH2[M14K]-C16-diacid/14] | −6.98 ± 0.17 | 104.7 | 3.8 | 419.8 | 82.6 | 5.1 |
| AT177 [hGIP(5-30NH2[D15K]-C16-diacid/15] | −7.43 ± 0.32 | 37.2 | 1.3 | 443.6 | 116.7 | 3.8 |
| AT140 [hGIP(5-30)-C16-diacid/16] | −6.69 ± 0.10 | 204.2 | 7.4 | 3278 | 2163 | 1.5 |
| AT178 [hGIP(5-30NH2[I17K]-C16-diacid/17] | −7.56 ± 0.19 | 27.5 | 1 | 242.7 | 54.3 | 4.5 |
| AT156 [hGIP(5-30NH2[H18K]-C16-diacid/18] | −7.62 ± 0.08 | 24.0 | 0.9 | 29.0 | 5.0 | 5.8 |
| AT179 [hGIP(5-30NH2[Q19K]-C16-diacid/19] | −7.24 ± 0.25 | 57.5 | 2.1 | 2376.8 | 378.4 | 6.3 |
| AT180 [hGIP(5-30NH2[Q20K]-C16-diacid/20] | −7.33 ± 0.19 | 46.8 | 1.7 | 533.3 | 82.8 | 6.4 |
| AT181 [hGIP(5-30NH2[D21K]-C16-diacid/21] | −7.90 ± 0.11 | 12.6 | 0.5 | 120.2 | 33.3 | 3.6 |
| AT182 [hGIP(5-30NH2[F22K]-C16-diacid/22] | −6.22 ± 0.23 | 602.6 | 21.9 | 1194.0 | 841.4 | 1.4 |
| AT183 [hGIP(5-30NH2[V23K]-C16-diacid/23] | −5.82 ± 0.49 | 1513.6 | 55.0 | 23281.0 | 5345.6 | 4.4 |
| AT184 [hGIP(5-30NH2[N24K]-C16-diacid/24] | −6.97 ± 0.12 | 107.2 | 3.9 | 871.0 | 224.4 | 3.9 |
| AT185 [hGIP(5-30NH2[W25K]-C16-diacid/25] | −7.18 ± 0.20 | 66.1 | 2.4 | 336.5 | 67.1 | 5.0 |
| AT186 [hGIP(5-30NH2[L26K]-C16-diacid/26] | −7.15 ± 0.21 | 70.8 | 2.6 | 829.9 | 104.7 | 7.9 |
| AT187 [hGIP(5-30NH2[L27K]-C16-diacid/27] | −5.73 ± 0.28 | 1862.1 | 67.6 | 3296097.1 | 181551.6 | 18.2 |
| AT188 [hGIP(5-30NH2[A28K]-C16-diacid/28] | −6.73 ± 0.10 | 186.2 | 6.8 | 462.4 | 143.5 | 3.2 |
| AT189 [hGIP(5-30NH2[Q29K]-C16-diacid/29] | −7.08 ± 0.12 | 83.2 | 3.0 | 276.1 | 85.5 | 3.2 |

Example 4—Addition of Linkers (Molecules Linking the Fatty Acids to the Peptides) Improves the Antagonistic Profile We added different minor molecules that link the peptides to the fatty acids to one of our promising antagonists (AT117). A linker could potentially increase the possibility of easy dissolution. The antagonistic properties were studied by the ability to inhibit a GIP-mediated cAMP response corresponding to 50-80% of maximum activation done in transiently transfected COS-7 cells expressing the human GIP receptor.

Results:

We observed that AT164 (linker γ-glutamic acid) and AT167 (linker 8-amino-3,6-dioxaoctanoic acid, γ-aminobuturic acid and β-alanine) had improved solubility as the analogues were soluble at concentrations of 200 μM whereas AT166 (linker γ-aminobuturic acid) and AT167 (linker β-alanine) could only obtain concentrations of 63.2 μM. Furthermore, it was observed that all analogues had an improved antagonistic profile compared to GIP(3-30)NH$_2$ (FIG. 3) with a 2.9 fold to 14.8 fold increase in potency (table 5). In summary, this analysis identified that the addition of specific linkers to the lipidation site results in GIP receptor antagonists with surprisingly high antagonistic potencies.

TABLE 5

Antagonist properties (FIG. 3) with the fold change from GIP(3-30)NH$_2$.

| Table 5 | cAMP accumulation | | |
|---|---|---|---|
| | logIC$_{50}$ ± SEM | IC$_{50}$ (nM) | Fold change |
| GIP(3-30)NH$_2$ | −7.19 ± 0.10 | 64.6 | — |
| AT164 [hGIP(3-30)NH$_2$[H18K]-C16/18+γ-glutamic acid] | −7.99 ± 0.15 | 10.2 | 6.3 |
| AT165 [hGIP(3-30)NH$_2$[H18K]-C16/18+γ-aminobuturic acid] | −7.65 ± 0.10 | 22.4 | 2.9 |
| AT166 [hGIP(3-30)NH$_2$[H18K]-C16/18+β-alanine] | −7.64 ± 0.09 | 22.9 | 2.9 |
| AT167 [hGIP(3-30)NH$_2$[H18K]-C16/18+γ-glutamic acid+8-amino-3,6-dioxaoctanoic acid] | −8.36 ± 0.06 | 4.4 | 14.8 |

Example 5—Lipidation Increases Albumin Binding of GIP Analogues

The point of lipidating GIP receptor antagonists is to achieve a longer T$_{1/2}$. As described previously, we have used the lipidated analogues' ability to bind to human serum albumin (HSA) to assess the potential of an increased T$_{1/2}$ in vivo. Heterologous competition binding was done in COS-7 cells transiently expressing the human GIP receptor in the absence and presence of 2% HSA.

Results:

As seen in tables 1, 2 and 3 several of the lipidated analogues have a very high albumin binding as the affinity changes up to 15.7 fold for both AT117 and AT136.

Example 6—Lipidation Increases the Elimination Half-Life of GIP Analogues

To assess how lipidation impacts T$_{1/2}$, we measured the T$_{1/2}$ of AT117, AT159, and AT175 in pigs. This was done by a subcutaneous administration of 1-10 nmol/kg in a total volume of 2-6 mL followed by collection of blood samples at time points from 15 min before administration of AT117 up to 57 h after the administration. As presented in FIG. 4, we have previously determined the T$_{1/2}$ of GIP(3-30)NH$_2$ to be 7.5 min in humans.

Results:

Lipidation increased the T$_{1/2}$ to 8 hour as seen for AT117 (FIG. 4) and 6 hours for AT159 and AT175 (table 3). Hence lipidation is an effective strategy to improve the pharmacokinetic properties of GIP peptides and thus can enable the development of long-acting GIP receptor antagonists.

Example 7—Protocol for Peptide Synthesis

All peptides were prepared by Fmoc based manual solid phase peptide synthesis using Rink amide MBHA resin with an initial loading of 0.35 mmol/g. Fmoc groups for N α-protection were cleaved by 8 min treatment with 20% piperidine in N,N-dimethylformamide (DMF) followed by second treatment with the same reagent for 10 min. After the Fmoc cleavage, the peptide-resin was washed with DMF (×6). The next residue was then incorporated with the DIPC/HOBt coupling protocol [Fmoc-amino acid (3 equiv), DIPC (3 equiv), and HOBt (3 equiv)]. After gentle agitation (1 hr) and washing with DMF (×6), part of the peptide-resin was subjected to the Kaiser test. If the Kaiser test shows positive result, re-coupling was carried out [Fmoc-amino acid (2 equiv), HATU (2 equiv), and DIEA (4 equiv)]. The steps for all the peptides were repeated until the peptide sequences were finished. Acylation of the peptides were performed after the peptide sequences were finished, but while the peptides were still bound to the resin.

Lot No: P170117-01-08:
Sequence: (1,16-Hexadecanedioic acid)-TFISDYSIAMD-KIHQQDFVNWLLAQK-NH$_2$ (SEQ ID NO:149),
Method for Conjugation of Fatty Acid:

After the last N-terminal N-Fmoc was removed, the N-terminal amino group was acylated by the treatment of 3 equiv 1,16-Hexadecanedioic acid in the presence of 3 equiv HATU and 6 equiv DIPEA.

```
Lot No: P290716-01-10B
Sequence: EGTFISDYSIAMDKI-K(Palm)-QQDFVNWLLAQK-NH2

Lot No: P280317-01-22
Sequence: TFISDYSIAMDKI-K(1,16-Hexadecanedioic
acid)-QQDFVNWLLAQK-NH2

Lot No: P290716-01-16
Sequence: TFISDYSIAMDKIHQQDFVNWLLAQK(Palm)-NH2
```

-continued

Lot No: P280317-01-30
Sequence: EGTFISDYSIAMDKI-K[(γ-Glu)-Palm]-

QQDFVNWLLAQK-NH2

Lot No: P280317-01-31
Sequence: EGTFISDYSIAMDKI-K[(4-Abu)-Palm]-

QQDFVNWLLAQK-NH2

Lot No: P280317-01-32
Sequence: EGTFISDYSIAMDKI-K[(β-Ala)-Palm]-

QQDFVNWLLAQK-NH2

Lot No: P280317-01-33
Sequence: EGTFISDYSIAMDKI-K[(γ-Glu)-AEEAc-Palm]-

QQDFVNWLLAQK-NH2

Methods for Conjugation of Fatty Acid:

Lysine with Dde protected side chain was used for the solid phase peptide synthesis in the acylation position. After the peptide chain was assembled, the N-terminal amino group was capped by 3 equiv Boc2O in the presence of 6 equiv DIPEA. Then the protection group Dde was removed by the treatment of 2% hydrazine/DMF (v/v).

For Lot no. P290716-01-10B and P290716-01-16:

3 equiv palmitoyl chloride was used for palmitoylation in the presence of 6 equiv DIPEA. For P280317-01-22, 3 equiv 1,16-Hexadecanedioic acid was activated by HATU/DIPEA and then conjugated to the side chain of Lysine.

For lot No: P280317-01-30/31/32/33:

Fmoc-γ-Glu(tBu)-OH or Fmoc-4-Abu-OH or Fmoc-β-Ala-OH or Fmoc-AEEAc-OH were conjugated to the side chain of Lys using a standard protocol of DIC/HOBT. The N-terminal amino groups of these unnatural amino acids were then palmitoylated by the treatment of 3 equiv palmitoyl chloride in the presence of 6 equiv DIPEA.

All peptides were finally released from the resin by TFA which also released the remaining protection groups. The peptides were purified using preparative HPLC and quality controlled by analytical HPLC and MALDI-TOF mass spectrometry.

The invention claimed is:

1. A glucose-dependent insulinotropic peptide (GIP) analogue selected from the group consisting of:

hGIP3-30 (SEQ ID NO:2)

| 1 | 2 | 3 | 4 | 5 | 6 | 7 | 8 | 9 | 10 | 11 | 12 |
|---|---|---|---|---|---|---|---|---|----|----|----|
| E | - G | - T | - F | - I | - S | - D | - Y | - S | - I | - A | - M |

| 13 | 14 | 15 | 16 | 17 | 18 | 19 | 20 | 21 | 22 | 23 | 24 |
|----|----|----|----|----|----|----|----|----|----|----|----|
| D | - K | - I | - H | - Q | - Q | - D | - F | - V | - N | - W | - L |

| 25 | 26 | 27 | 28 |
|----|----|----|----|
| L | - A | - Q | - K | and hGIP5-30 (SEQ ID NO:1)

| 1 | 2 | 3 | 4 | 5 | 6 | 7 | 8 | 9 | 10 | 11 | 12 |
|---|---|---|---|---|---|---|---|---|----|----|----|
| T | - F | - I | - S | - D | - Y | - S | - I | - A | - M | - D | - K |

| 13 | 14 | 15 | 16 | 17 | 18 | 19 | 20 | 21 | 22 | 23 | 24 |
|----|----|----|----|----|----|----|----|----|----|----|----|
| I | - H | - Q | - Q | - D | - F | - V | - N | - W | - L | - L | - A |

| 25 | 26 |
|----|----|
| Q | - K | or a functional variant of any one of SEQ ID NO:2 and SEQ ID NO:1 having 1 to 6 individual amino acid substitutions, wherein said peptide comprises at least one fatty acid molecule at one or more amino acid residues at positions 2 to 19 of SEQ ID NO:2, or at positions 1 to 17 of SEQ ID NO:1, or said functional variant thereof, and wherein said peptide is an antagonist of the hGIP receptor.

2. The GIP peptide analogue according to claim 1, wherein E (Glu) at position 1 of SEQ ID NO:2 is substituted with pGlu (pyroglutamic acid).

3. The GIP peptide analogue according to claim 1, wherein one or more of: K at position 28, and/or K at position 14, and/or M at position 12, and/or D at position 13, and/or the H at position 16 of SEQ ID NO:2, or one or more of: K at position 26, and/or K at position 12, and/or M at position 10, and/or D at position 11, and/or the H at position 14 of SEQ ID NO:1, or said functional variant thereof, are individually substituted with any amino acid.

4. The GIP peptide analogue according to claim 1, wherein K at position 28 of SEQ ID NO:2, or K at position 26 of SEQ ID NO:1, or said functional variant thereof, is substituted with an amino acid selected from the group consisting of: R, A and E.

5. The GIP peptide analogue according to claim 1, wherein K at position 14 of SEQ ID NO:2, or K at position 12 of SEQ ID NO:1, or said functional variant thereof, is substituted with an amino acid selected from the group consisting of: R, A and E.

6. The GIP peptide analogue according to claim 1, wherein M at position 12 of SEQ ID NO:2, or M at position 10 of SEQ ID NO:1, or said functional variant thereof, is substituted with L, S, K, norleucine (Nle) or methoxinine (Mox).

7. The GIP peptide analogue according to claim 1, wherein D at position 13 of SEQ ID NO:2, or D at position 11 of SEQ ID NO:1, or said functional variant thereof, is substituted with an amino acid selected from the group consisting of: E, A, K and Orn.

8. The GIP peptide analogue according to claim 1, wherein H at position 16 of SEQ ID NO:2, or H at position 14 of SEQ ID NO:1, or said functional variant thereof, is substituted with an amino acid selected from the group consisting of: A, R, K and Orn.

9. The GIP peptide analogue according to claim 1, wherein said at least one fatty acid molecule is attached to one or more amino acid residues at any one of positions 9 to 19 of SEQ ID NO:2, or at any one of positions 7 to 17 of SEQ ID NO:1, or said functional variant thereof; and/or
wherein said at least one fatty acid molecule is attached to an amino acid residue at position 3 of SEQ ID NO:2, or at position 1 of SEQ ID NO:1, or said functional variant thereof.

10. The GIP peptide analogue according to claim 9, wherein a fatty acid molecule is attached to
i) an amino acid residue at position 16 of SEQ ID NO:2, or at position 16 of SEQ ID NO:1, or said functional variant thereof, and/or
ii) an amino acid residue at position 9 of SEQ ID NO:2, or at position 7 of SEQ ID NO:1, or said functional variant thereof, and/or
iii) an amino acid residue at position 14 of SEQ ID NO:2, or at position 12 of SEQ ID NO:1, or said functional variant thereof, and/or
iv) an amino acid residue at position 13 of SEQ ID NO:2, or at position 11 of SEQ ID NO:1, or said functional variant thereof, and/or
v) an amino acid residue at position 10 of SEQ ID NO:2, or at position 8 of SEQ ID NO:1, or said functional variant thereof, and/or vi) an amino acid residue at position 11 of SEQ ID NO:2, or at position 9 of SEQ ID NO:1, or said functional variant thereof, and/or vii) an amino acid residue at position 19 of SEQ ID NO:2, or at position 17 of SEQ ID NO:1, or said functional variant thereof, and/or viii) an amino acid residue at position 3 of SEQ ID NO:2, or at position 1 of SEQ ID NO:1, or said functional variant thereof, and/or ix) an amino acid residue at position 12 of any one of SEQ ID NO:2, or at position 10 of SEQ ID NO:1, or said functional variant thereof, and/or x) an amino acid residue at position 18 of SEQ ID NO:2, or at position 16 of SEQ ID NO:1, or said functional variant thereof, and/or xi) an amino acid residue at position 5 of SEQ ID NO:2, or at position 3 of SEQ ID NO:1, or said functional variant thereof, and/or xii) an amino acid residue at position 7 of SEQ ID NO:2, or at position 5 of SEQ ID NO:1, or said functional variant thereof, and/or xiii) an amino acid residue at position 15 of SEQ ID NO:2, or at position 13 of SEQ ID NO:1, or said functional variant thereof.

11. The GIP peptide analogue according to claim 9, wherein a fatty acid molecule is attached to an amino acid residue at position 16 of SEQ ID NO:2 or at position 14 of SEQ ID NO:1, or said functional variant thereof.

12. The GIP peptide analogue according to claim 1, wherein said at least one fatty acid molecule is attached to an epsilon-amino group of a K residue, or to a delta-amino group of a Orn residue, of any one of amino acid residues at positions 2 to 19 of SEQ ID NO:2 or at positions 1 to 17 of SEQ ID NO:1, or said functional variant thereof.

13. The GIP peptide analogue according to claim 1, wherein said fatty acid molecule comprises one or more acyl groups selected from the group consisting of: $CH_3(CH_2)_6CO-$, $CH_3(CH_2)_8CO-$, $CH_3(CH_2)_{10}CO-$, $CH_3(CH_2)_{12}CO-$, $CH_3(CH_2)_{14}CO-$, $CH_3(CH_2)_{16}CO-$, $CH_3(CH_2)_{18}CO-$, $CH_3(CH_2)_{20}CO-$ and $CH_3(CH_2)_{22}CO-$.

14. The GIP peptide analogue according to claim 1, wherein said fatty acid molecule comprises one or more acyl groups selected from the group consisting of: $COOH(CH_2)_{14}CO-$, $COOH(CH_2)_{16}CO-$, $COOH(CH_2)_{18}CO-$ and $COOH(CH_2)_{20}CO-$.

15. The GIP peptide analogue according to claim 1, wherein said fatty acid molecule is attached to an amino acid residue directly.

16. The GIP peptide analogue according to claim 1, wherein said fatty acid molecule is attached to an amino acid residue via a spacer, wherein said spacer optionally comprises one or more moieties individually selected from the group consisting of: one or more α,ω-amino acids; one or more amino acids selected from the group consisting of: succinic acid, Lys, Glu, and Asp; 4-Abu; γ-aminobuturic acid; a dipeptide; one or more of: γ-aminobutanoyl (γ-aminobutyric acid), γ-glutamyl (γ-glutamic acid), β-asparagyl, β-alanyl and glycyl; and [γ-glutamic acid-8-amino-3,6-dioxaoctanoic acid]$_n$ (γGlu-AEEAc$_n$), wherein n is an integer between 1 and 50.

17. The GIP peptide analogue according to claim 1, wherein said peptide is selected from the group consisting of:

(hGIP3-30, SEQ ID NO: 2)
EGTFISDYSIAMDKIHQQDFVNWLLAQK, (hGIP(3-30)K16R H18K K30R; SEQ ID NO: 72)
EGTFISDYSIAMDRIKQQDFVNWLLAQR, (hGIP(3-30)K16R K30R; SEQ ID NO: 73)
EGTFISDYSIAMDRIHQQDFVNWLLAQR, (hGIP(3-30)H18A; SEQ ID NO: 74)
EGTFISDYSIAMDKIAQQDFVNWLLAQK, (hGIP(3-30)H18K; SEQ ID NO: 75)
EGTFISDYSIAMDKIKQQDFVNWLLAQK, (hGIP(3-30)D15E H18A; SEQ ID NO: 76)
EGTFISDYSIAMEKIAQQDFVNWLLAQK, (hGIP(3-30)K16A H18A; SEQ ID NO: 77)
EGTFISDYSIAMDAIAQQDFVNWLLAQK, (hGIP(3-30)D15E; SEQ ID NO: 78)
EGTFISDYSIAMEKIHQQDFVNWLLAQK, (hGIP(3-30)D15N; SEQ ID NO: 79)
EGTFISDYSIAMNKIHQQDFVNWLLAQK, (hGIP(3-30)K16A; SEQ ID NO: 80)
EGTFISDYSIAMDAIHQQDFVNWLLAQK, (hGIP(3-30)K16H; SEQ ID NO: 81)
EGTFISDYSIAMDHIHQQDFVNWLLAQK, (hGIP(3-30)K16R; SEQ ID NO: 82)
EGTFISDYSIAMDRIHQQDFVNWLLAQK, (hGIP(3-30)H18F; SEQ ID NO: 83)
EGTFISDYSIAMDKIFQQDFVNWLLAQK, (hGIP(3-30)H18W; SEQ ID NO: 84)
EGTFISDYSIAMDKIWQQDFVNWLLAQK, (hGIP(3-30)K30R; SEQ ID NO: 85)
EGTFISDYSIAMDKIHQQDFVNWLLAQR, (hGIP(3-30)K30H; SEQ ID NO: 86)
EGTFISDYSIAMDKIHQQDFVNWLLAQH.

(hGIP(3-30)G4K, SEQ ID NO: 87)
EKTFISDYSIAMDKIHQQDFVNWLLAQK, (hGIP(3-30)T5K, SEQ ID NO: 88)
EGKFISDYSIAMDKIHQQDFVNWLLAQK, (hGIP(3-30)F6K, SEQ ID NO: 89)
EGTKISDYSIAMDKIHQQDFVNWLLAQK, (hGIP(3-30)I7K, SEQ ID NO: 90)
EGTFKSDYSIAMDKIHQQDFVNWLLAQK, (hGIP(3-30)S8K, SEQ ID NO: 91)
EGTFIKDYSIAMDKIHQQDFVNWLLAQK, (hGIP(3-30)D9K, SEQ ID NO: 92)
EGTFISKYSIAMDKIHQQDFVNWLLAQK, (hGIP(3-30)Y10K, SEQ ID NO: 93)
EGTFISDKSIAMDKIHQQDFVNWLLAQK, (hGIP(3-30)S11K, SEQ ID NO: 94)
EGTFISDYKIAMDKIHQQDFVNWLLAQK, (hGIP(3-30)I12K, SEQ ID NO: 95)
EGTFISDYSKAMDKIHQQDFVNWLLAQK, (hGIP(3-30)A13K, SEQ ID NO: 96)
EGTFISDYSIKMDKIHQQDFVNWLLAQK, (hGIP(3-30)M14K, SEQ ID NO: 97)
EGTFISDYSIAKDKIHQQDFVNWLLAQK, (hGIP(3-30)D15K, SEQ ID NO: 98)
EGTFISDYSIAMKKIHQQDFVNWLLAQK, (hGIP(3-30)I17K, SEQ ID NO: 99)
EGTFISDYSIAMDKKHQQDFVNWLLAQK, (hGIP(3-30)Q19K, SEQ ID NO: 100)
EGTFISDYSIAMDKIHKQDFVNWLLAQK, (hGIP(3-30)Q20K, SEQ ID NO: 101)
EGTFISDYSIAMDKIHQKDFVNWLLAQK, (hGIP(3-30)D21K, SEQ ID NO: 102)
EGTFISDYSIAMDKIHQQKFVNWLLAQK, (hGIP(3-30)F22K, SEQ ID NO: 103)
EGTFISDYSIAMDKIHQQDKVNWLLAQK, (hGIP(3-30)V23K, SEQ ID NO: 104)
EGTFISDYSIAMDKIHQQDFKNWLLAQK, (hGIP(3-30)N24K, SEQ ID NO: 105)
EGTFISDYSIAMDKIHQQDFVKWLLAQK, (hGIP(3-30)W25K, SEQ ID NO: 106)
EGTFISDYSIAMDKIHQQDFVNKLLAQK, (hGIP(3-30)L26K, SEQ ID NO: 107)
EGTFISDYSIAMDKIHQQDFVNWKLAQK, (hGIP(3-30)L27K, SEQ ID NO: 108)
EGTFISDYSIAMDKIHQQDFVNWLKAQK, (hGIP(3-30)A28K, SEQ ID NO: 109)
EGTFISDYSIAMDKIHQQDFVNWLLKQK, (hGIP(3-30)Q29K, SEQ ID NO: 110)
EGTFISDYSIAMDKIHQQDFVNWLLAKK, (hGIP(3-30)S11K H18A, SEQ ID NO: 111)
EGTFISDYKIAMDKIAQQDFVNWLLAQK, (hGIP(3-30)S11K H18R, SEQ ID NO: 112)
EGTFISDYKIAMDKIRQQDFVNWLLAQK, (hGIP(3-30)S11K D15E, SEQ ID NO: 113)
EGTFISDYKIAMEKIHQQDFVNWLLAQK, (hGIP(3-30)S11K M14Nle, SEQ ID NO: 114)
EGTFISDYKIANleDKIHQQDFVNWLLAQK, (hGIP(3-30)S11K M14L, SEQ ID NO: 115)
EGTFISDYKIALDKIHQQDFVNWLLAQK, (hGIP(3-30)I12K H18A, SEQ ID NO: 116)
EGTFISDYSKAMDKIAQQDFVNWLLAQK, (hGIP(3-30)I12K H18R, SEQ ID NO: 117)
EGTFISDYSKAMDKIRQQDFVNWLLAQK, (hGIP(3-30)I12K D15E, SEQ ID NO: 118)
EGTFISDYSKAMEKIHQQDFVNWLLAQK, (hGIP(3-30)I12K M14Nle, SEQ ID NO: 119)
EGTFISDYSKAN1eDKIHQQDFVNWLLAQK, (hGIP(3-30)I12K M14L, SEQ ID NO: 120)
EGTFISDYSKALDKIHQQDFVNWLLAQK, (hGIP(3-30)A13K H18A, SEQ ID NO: 121)
EGTFISDYSIKMDKIAQQDFVNWLLAQK, (hGIP(3-30)A13K H18R, SEQ ID NO: 122)
EGTFISDYSIKMDKIRQQDFVNWLLAQK,

```
                (hGIP(3-30)A13K D15E, SEQ ID NO: 123)
EGTFISDYSIKMEKIHQQDFVNWLLAQK, (hGIP(3-30)A13K M14Nle, SEQ ID NO: 124)
EGTFISDYSIKNleDKIHQQDFVNWLLAQK, (hGIP(3-30)A13K M14L, SEQ ID NO: 125)
EGTFISDYSIKLDKIHQQDFVNWLLAQK, (hGIP(3-30)D15E H18K; SEQ ID NO: 126)
EGTFISDYSIAMEKIKQQDFVNWLLAQK, (hGIP(3-30)M14Nle H18K; SEQ ID NO: 127)
EGTFISDYSIANleDKIKQQDFVNWLLAQK, (hGIP(3-30)M14L H18K; SEQ ID NO: 128)
EGTFISDYSIALDKIKQQDFVNWLLAQK, (hGIP(3-30)T5K K16R K30R, SEQ ID NO: 129)
EGKFISDYSIAMDRIHQQDFVNWLLAQR, (hGIP(3-30)D15Orn, SEQ ID NO: 130)
EGTFISDYSIAMOrnKIHQQDFVNWLLAQK, (hGIP(3-30)H18Orn; SEQ ID NO: 131)
EGTFISDYSIAMDKIOrnQQDFVNWLLAQK, (hGIP(3-30)M14L K16R H18K K30R; (SEQ ID NO: 132)
EGTFISDYSIALDRIKQQDFVNWLLAQR, (SEQ ID NO: 144)
EGWFISDYSIAMEKIAQQDFVNWLLAQK,
and (SEQ ID NO: 146)
EGTFISDYSIAMDKIKQQDFVNWLLAQR,
``` wherein said peptide comprises at least one fatty acid molecule at one or more amino acid residues at position 2 to 19.

18. The GIP peptide analogue according to claim 1, wherein said peptide is selected from the group consisting of:

```
                        (hGIP5-30, SEQ ID NO: 1)
TFISDYSIAMDKIHQQDFVNWLLAQK, (hGIP(5-30)K16R H18K K30R; SEQ ID NO: 5)
TFISDYSIAMDRIKQQDFVNWLLAQR, (hGIP(5-30)K16R K30R; SEQ ID NO: 6)
TFISDYSIAMDRIHQQDFVNWLLAQR, (hGIP(5-30)H18A; SEQ ID NO: 7)
TFISDYSIAMDKIAQQDFVNWLLAQK, (hGIP(5-30)H18K; SEQ ID NO: 8)
TFISDYSIAMDKIKQQDFVNWLLAQK, (hGIP(5-30)D15E H18A; SEQ ID NO: 9)
TFISDYSIAMEKIAQQDFVNWLLAQK, (hGIP(5-30)K16A H18A; SEQ ID NO: 10)
TFISDYSIAMDAIAQQDFVNWLLAQK, (hGIP(5-30)D15E; SEQ ID NO: 11)
TFISDYSIAMEKIHQQDFVNWLLAQK, (hGIP(5-30)D15N; SEQ ID NO: 12)
TFISDYSIAMNKIHQQDFVNWLLAQK, (hGIP(5-30)K16A; SEQ ID NO: 13)
TFISDYSIAMDAIHQQDFVNWLLAQK, (hGIP(5-30)K16H; SEQ ID NO: 14)
TFISDYSIAMDHIHQQDFVNWLLAQK, (hGIP(5-30)K16R; SEQ ID NO: 15)
TFISDYSIAMDRIHQQDFVNWLLAQK, (hGIP(5-30)H18F; SEQ ID NO: 16)
TFISDYSIAMDKIFQQDFVNWLLAQK, (hGIP(5-30)H18W; SEQ ID NO: 17)
TFISDYSIAMDKIWQQDFVNWLLAQK, (hGIP(5-30)K30R; SEQ ID NO: 18)
TFISDYSIAMDKIHQQDFVNWLLAQR, (hGIP(5-30)K30H; SEQ ID NO: 19)
TFISDYSIAMDKIHQQDFVNWLLAQH.

(hGIP(5-30)T5K, SEQ ID NO: 20)
KFISDYSIAMDKIHQQDFVNWLLAQK, (hGIP(5-30)F6K, SEQ ID NO: 21)
TKISDYSIAMDKIHQQDFVNWLLAQK, (hGIP(5-30)I7K, SEQ ID NO: 22)
TFKSDYSIAMDKIHQQDFVNWLLAQK, (hGIP(5-30)S8K, SEQ ID NO: 23)
TFIKDYSIAMDKIHQQDFVNWLLAQK, (hGIP(5-30)D9K, SEQ ID NO: 24)
TFISKYSIAMDKIHQQDFVNWLLAQK, (hGIP(5-30)Y10K, SEQ ID NO: 25)
TFISDKSIAMDKIHQQDFVNWLLAQK, (hGIP(5-30)S11K, SEQ ID NO: 26)
TFISDYKIAMDKIHQQDFVNWLLAQK, (hGIP(5-30)I12K, SEQ ID NO: 27)
TFISDYSKAMDKIHQQDFVNWLLAQK, (hGIP(5-30)A13K, SEQ ID NO: 28)
TFISDYSIKMDKIHQQDFVNWLLAQK, (hGIP(5-30)M14K, SEQ ID NO: 29)
TFISDYSIAKDKIHQQDFVNWLLAQK, (hGIP(5-30)D15K, SEQ ID NO: 30)
TFISDYSIAMKKIHQQDFVNWLLAQK, (hGIP(5-30)I17K, SEQ ID NO: 31)
TFISDYSIAMDKKHQQDFVNWLLAQK, (hGIP(5-30)Q19K, SEQ ID NO: 32)
TFISDYSIAMDKIHKQDFVNWLLAQK, (hGIP(5-30)Q20K, SEQ ID NO: 33)
TFISDYSIAMDKIHQKDFVNWLLAQK, (hGIP(5-30)D21K, SEQ ID NO: 34)
TFISDYSIAMDKIHQQKFVNWLLAQK, (hGIP(5-30)F22K, SEQ ID NO: 35)
TFISDYSIAMDKIHQQDKVNWLLAQK, (hGIP(5-30)V23K, SEQ ID NO: 36)
TFISDYSIAMDKIHQQDFKNWLLAQK, (hGIP(5-30)N24K, SEQ ID NO: 37)
TFISDYSIAMDKIHQQDFVKWLLAQK, (hGIP(5-30)W25K, SEQ ID NO: 38)
TFISDYSIAMDKIHQQDFVNKLLAQK, (hGIP(5-30)L26K, SEQ ID NO: 39)
TFISDYSIAMDKIHQQDFVNWKLAQK, (hGIP(5-30)L27K, SEQ ID NO: 40)
TFISDYSIAMDKIHQQDFVNWLKAQK, (hGIP(5-30)A28K, SEQ ID NO: 41)
TFISDYSIAMDKIHQQDFVNWLLKQK,
```

-continued (hGIP(5-30)Q29K, SEQ ID NO: 42)
TFISDYSIAMDKIHQQDFVNWLLAKK, (hGIP(5-30)S11K H18A, SEQ ID NO: 43)
TFISDYKIAMDKIAQQDFVNWLLAQK, (hGIP(5-30)S11K H18R, SEQ ID NO: 44)
TFISDYKIAMDKIRQQDFVNWLLAQK, (hGIP(5-30)S11K D15E, SEQ ID NO: 45)
TFISDYKIAMEKIHQQDFVNWLLAQK, (hGIP(5-30)S11K M14Nle, SEQ ID NO: 46)
TFISDYKIANleDKIHQQDFVNWLLAQK, (hGIP(5-30)S11K M14L, SEQ ID NO: 47)
TFISDYKIALDKIHQQDFVNWLLAQK, (hGIP(5-30)I12K H18A, SEQ ID NO: 48)
TFISDYSKAMDKIAQQDFVNWLLAQK, (hGIP(5-30)I12K H18R, SEQ ID NO: 49)
TFISDYSKAMDKIRQQDFVNWLLAQK, (hGIP(5-30)I12K D15E, SEQ ID NO: 50)
TFISDYSKAMEKIHQQDFVNWLLAQK, (hGIP(5-30)I12K M14Nle, SEQ ID NO: 51)
TFISDYSKANleDKIHQQDFVNWLLAQK, (hGIP(5-30)I12K M14L, SEQ ID NO: 52)
TFISDYSKALDKIHQQDFVNWLLAQK, (hGIP(5-30)A13K H18A, SEQ ID NO: 53)
TFISDYSIKMDKIAQQDFVNWLLAQK, (hGIP(5-30)A13K H18R, SEQ ID NO: 54)
TFISDYSIKMDKIRQQDFVNWLLAQK, (hGIP(5-30)A13K D15E, SEQ ID NO: 55)
TFISDYSIKMEKIHQQDFVNWLLAQK, (hGIP(5-30)A13K M14Nle, SEQ ID NO: 56)
TFISDYSIKNleDKIHQQDFVNWLLAQK, (hGIP(5-30)A13K M14L, SEQ ID NO: 57)
TFISDYSIKLDKIHQQDFVNWLLAQK, (hGIP(5-30)D15E H18K; SEQ ID NO: 58)
TFISDYSIAMEKIKQQDFVNWLLAQK, (hGIP(5-30)M14Nle H18K; SEQ ID NO: 59)
TFISDYSIANleDKIKQQDFVNWLLAQK, (hGIP(5-30)M14L H18K; SEQ ID NO: 60)
TFISDYSIALDKIKQQDFVNWLLAQK, (hGIP(5-30)D15Orn, SEQ ID NO: 61)
TFISDYSIAMOrnKIHQQDFVNWLLAQK, (hGIP(5-30)H18Orn; SEQ ID NO: 62)
TFISDYSIAMDKIOrnQQDFVNWLLAQK, (hGIP(5-30)M14L K16R H18K K30R; SEQ ID NO: 63)
TFISDYSIALDRIKQQDFVNWLLAQR, (hGIP(5-30)T5K K16R K30R, SEQ ID NO: 64)
KFISDYSIAMDRIHQQDFVNWLLAQR

(hGIP(5-30)T5K M14L K16R K30R, SEQ ID NO: 65)
KFISDYSIAMDKIHQQDFVNWLLAQK, (hGIP(5-30)S11K K16R K30R, SEQ ID NO: 66)
TFISDYKIAMDRIHQQDFVNWLLAQR, (hGIP(5-30)S11K M14L K16R K30R, SEQ ID NO: 67)
TFISDYKIALDRIHQQDFVNWLLAQR, (hGIP(5-30)I12K K16R K30R, SEQ ID NO: 68)
TFISDYSKAMDRIHQQDFVNWLLAQR,

-continued (hGIP(5-30)I12K M14L K16R K30R, SEQ ID NO: 69)
TFISDYSKALDRIHQQDFVNWLLAQR, (hGIP(5-30)A13K K16R K30R, SEQ ID NO: 70)
TFISDYSIKMDRIHQQDFVNWLLAQR, (hGIP(5-30)A13K M14L K16R K30R, SEQ ID NO: 71)
TFISDYSIKLDRIHQQDFVNWLLAQR,
and (SEQ ID NO: 145)
TFISDYSIAMDRIHQQKFVNWLLAQR, wherein said peptide comprises at least one fatty acid molecule at one or more amino acid residues at position 1 to 17.

19. The GIP peptide analogue according to claim 1 which is selected from the group consisting of:

(SEQ ID NO: 1)
TFISDYSIAMDKIHQQDFVNWLLAQK-C12/T1, (SEQ ID NO: 1)
TFISDYSIAMDKIHQQDFVNWLLAQK-C12/K12, (SEQ ID NO: 1)
TFISDYSIAMDKIHQQDFVNWLLAQK-C14/T1, (SEQ ID NO: 1)
TFISDYSIAMDKIHQQDFVNWLLAQK-C14/K12, (SEQ ID NO: 1)
TFISDYSIAMDKIHQQDFVNWLLAQK-C16/T1, (SEQ ID NO: 1)
TFISDYSIAMDKIHQQDFVNWLLAQK-C16/K12, (SEQ ID NO: 1)
TFISDYSIAMDKIHQQDFVNWLLAQK-C18/T1, (SEQ ID NO: 1)
TFISDYSIAMDKIHQQDFVNWLLAQK-C18/K12, (SEQ ID NO: 5)
TFISDYSIAMDRIKQQDFVNWLLAQR-C16/T1, (SEQ ID NO: 5)
TFISDYSIAMDRIKQQDFVNWLLAQR-C16/K14, (SEQ ID NO: 6)
TFISDYSIAMDRIHQQDFVNWLLAQR-C16/T1, (SEQ ID NO: 1)
TFISDYSIAMDKIHQQDFVNWLLAQK-C14-diacid/T1, (SEQ ID NO: 1)
TFISDYSIAMDKIHQQDFVNWLLAQK-C16-diacid/T1, (SEQ ID NO: 1)
TFISDYSIAMDKIHQQDFVNWLLAQK-C18-diacid/T1, (SEQ ID NO: 1)
TFISDYSIAMDKIHQQDFVNWLLAQK-C14-diacid/K12, (SEQ ID NO: 1)
TFISDYSIAMDKIHQQDFVNWLLAQK-C16-diacid/K12, (SEQ ID NO: 1)
TFISDYSIAMDKIHQQDFVNWLLAQK-C18-diacid/K12, (SEQ ID NO: 8)
TFISDYSIAMDKIKQQDFVNWLLAQK-C16-diacid/K14, (SEQ ID NO: 8)
TFISDYSIAMDKIKQQDFVNWLLAQK-C18-diacid/K14, (SEQ ID NO: 5)
TFISDYSIAMDRIKQQDFVNWLLAQR-C16-diacid/K14,

```
                                              (SEQ ID NO: 20)
KFISDYSIAMDKIHQQDFVNWLLAQK-C14-diacid/K1, (SEQ ID NO: 20)
KFISDYSIAMDKIHQQDFVNWLLAQK-C16-diacid/K1, (SEQ ID NO: 20)
KFISDYSIAMDKIHQQDFVNWLLAQK-C18-diacid/K1, (SEQ ID NO: 64)
KFISDYSIAMDRIHQQDFVNWLLAQR-C16-diacid/K1, (SEQ ID NO: 64)
KFISDYSIAMDRIHQQDFVNWLLAQR-C18-diacid/K1, (SEQ ID NO: 26)
TFISDYKIAMDKIHQQDFVNWLLAQK-C16-diacid/K7, (SEQ ID NO: 66)
TFISDYKIAMDRIHQQDFVNWLLAQR-C16-diacid/K7, (SEQ ID NO: 26)
TFISDYKIAMDKIHQQDFVNWLLAQK-C18-diacid/K7, (SEQ ID NO: 66)
TFISDYKIAMDRIHQQDFVNWLLAQR-C18-diacid/K7, (SEQ ID NO: 27)
TFISDYSKAMDKIHQQDFVNWLLAQK-C16-diacid/K8, (SEQ ID NO: 68)
TFISDYSKAMDRIHQQDFVNWLLAQR-C16-diacid/K8, (SEQ ID NO: 27)
TFISDYSKAMDKIHQQDFVNWLLAQK-C18-diacid/K8, (SEQ ID NO: 68)
TFISDYSKAMDRIHQQDFVNWLLAQR-C18-diacid/K8, (SEQ ID NO: 28)
TFISDYSIKMDKIHQQDFVNWLLAQK-C16-diacid/K9, (SEQ ID NO: 70)
TFISDYSIKMDRIHQQDFVNWLLAQR-C16-diacid/K9, (SEQ ID NO: 28)
TFISDYSIKMDKIHQQDFVNWLLAQK-C18-diacid/K9, (SEQ ID NO: 70)
TFISDYSIKMDRIHQQDFVNWLLAQR-C18-diacid/K9, (SEQ ID NO: 6)
TFISDYSIAMDRIHQQDFVNWLLAQR-C16-diacid/K12, (SEQ ID NO: 6)
TFISDYSIAMDRIHQQDFVNWLLAQR-C18-diacid/K12, (SEQ ID NO: 5)
TFISDYSIAMDRIKQQDFVNWLLAQR-C18-diacid/K14, (SEQ ID NO: 34)
TFISDYSIAMDKIHQQKFVNWLLAQK-C16-diacid/K17, (SEQ ID NO: 145)
TFISDYSIAMDRIHQQKFVNWLLAQR-C16-diacid/K17, (SEQ ID NO: 34)
TFISDYSIAMDKIHQQKFVNWLLAQK-C18-diacid/K17, (SEQ ID NO: 145)
TFISDYSIAMDRIHQQKFVNWLLAQR-C18-diacid/K17, (SEQ ID NO: 2)
EGTFISDYSIAMDKIHQQDFVNWLLAQK-C12/K14, (SEQ ID NO: 2)
EGTFISDYSIAMDKIHQQDFVNWLLAQK-C16/K14, (SEQ ID NO: 144)
EGWFISDYSIAMEKIAQQDFVNWLLAQK-C16/K14, (SEQ ID NO: 2)
EGTFISDYSIAMDKIHQQDFVNWLLAQK-C14/K14, (SEQ ID NO: 2)
EGTFISDYSIAMDKIHQQDFVNWLLAQK-C18/K14, (SEQ ID NO: 75)
EGTFISDYSIAMDKIKQQDFVNWLLAQK-C12/K16, (SEQ ID NO: 75)
EGTFISDYSIAMDKIKQQDFVNWLLAQK-C16/K16, (SEQ ID NO: 76)
EGTFISDYSIAMEKIAQQDFVNWLLAQK-C16/K14, (SEQ ID NO: 75)
EGTFISDYSIAMDKIKQQDFVNWLLAQK-C16-diacid/K16, (SEQ ID NO: 75)
EGTFISDYSIAMDKIKQQDFVNWLLAQK-C18-diacid/K16, (SEQ ID NO: 72)
EGTFISDYSIAMDRIKQQDFVNWLLAQR-C16-diacid/K16, (SEQ ID NO: 146)
EGTFISDYSIAMDKIKQQDFVNWLLAQR-C18-diacid/K16, (SEQ ID NO: 146)
EGTFISDYSIAMDKIKQQDFVNWLLAQR-C16/K16, (SEQ ID NO: 128)
EGTFISDYSIALDKIKQQDFVNWLLAQK-C16/K16, (SEQ ID NO: 75)
EGTFISDYSIAMDKIKQQDFVNWLLAQK-C16-diacid/K16, (SEQ ID NO: 72)
EGTFISDYSIAMDRIKQQDFVNWLLAQR-C16-diacid/K16, (SEQ ID NO: 75)
EGTFISDYSIAMDKIKQQDFVNWLLAQK-C18/K16, (SEQ ID NO: 88)
EGKFISDYSIAMDKIHQQDFVNWLLAQK-C16-diacid/K3, (SEQ ID NO: 129)
EGKFISDYSIAMDRIHQQDFVNWLLAQR-C16-diacid/K3, (SEQ ID NO: 88)
EGKFISDYSIAMDKIHQQDFVNWLLAQK-C18-diacid/K3, (SEQ ID NO: 129)
EGKFISDYSIAMDRIHQQDFVNWLLAQR-C18-diacid/K3,
and
                                              (SEQ ID NO: 72)
EGTFISDYSIAMDRIKQQDFVNWLLAQR-C18-diacid/K16,
``` or a functional variant thereof, wherein said fatty acid is attached directly or via a spacer.

20. The GIP peptide analogue according claim 1, wherein said peptide is C-terminally amidated (—NH$_2$).

21. A method of treating a condition, the condition selected from the group consisting of: metabolic syndrome, obesity, over-weight, pre-diabetes, diabetes mellitus type 1, diabetes mellitus type 2, insulin resistance, elevated fasting glucose, elevated fasting serum triglyceride level, low high-density lipoprotein (HDL) levels, a fatty acid metabolism disorder, a cardiovascular disease, elevated blood pressure, and atherosclerosis, said method comprising one or more steps of administering to an individual in need thereof a therapeutically effective amount of a GIP peptide analogue according to claim 1.

22. The GIP peptide analogue of claim 1, wherein said peptide comprises at least one fatty acid molecule at one or more amino acid residues at positions 3, 5, 7, 9, 10, 11, 13, 15, 16, 18, and 19 of any one of SEQ ID NO:2, or at positions 1, 3, 5, 7, 8, 9, 11, 13, 14, 16, and 17 of SEQ ID NO:1, or said functional variant thereof.

23. The GIP peptide analogue of claim 1, wherein said peptide comprises at least one fatty acid molecule at one or more amino acid residues at positions 9-19 of any one of SEQ ID NO:2, or at positions 1 to 17 of SEQ ID NO:1, or said functional variant thereof.

* * * * *